(12) United States Patent
Bright et al.

(10) Patent No.: US 7,345,038 B2
(45) Date of Patent: Mar. 18, 2008

(54) PYRIDYLOXYMETHYL AND BENZISOXAZOLE AZABICYCLIC DERIVATIVES

(75) Inventors: Gene Michael Bright, Groton, CT (US); Michael A. Brodney, Old Lyme, CT (US); Bishop Wlodecki, Preston, CT (US)

(73) Assignee: Pfizer, Inc, New York, NY (US)

( * ) Notice: Subject to any disclaimer, the term of this patent is extended or adjusted under 35 U.S.C. 154(b) by 264 days.

(21) Appl. No.: 10/800,328

(22) Filed: Mar. 12, 2004

(65) Prior Publication Data

US 2005/0026922 A1   Feb. 3, 2005

Related U.S. Application Data

(60) Provisional application No. 60/453,925, filed on Mar. 12, 2003.

(51) Int. Cl.
  *A01N 43/00* (2006.01)
  *A01N 43/58* (2006.01)
  *A01N 43/60* (2006.01)
  *A61K 31/55* (2006.01)
  *A61K 31/50* (2006.01)

(52) U.S. Cl. .................. 514/217.07; 514/249; 544/349; 540/599

(58) Field of Classification Search .................. None
See application file for complete search history.

(56) References Cited

U.S. PATENT DOCUMENTS

| | | | |
|---|---|---|---|
| 5,122,525 A | 6/1992 | Bright et al. | 514/249 |
| 5,157,034 A | 10/1992 | Bright et al. | 514/249 |
| 5,565,453 A | 10/1996 | Bright et al. | 514/249 |
| 5,719,286 A | 2/1998 | Urban | 544/349 |
| 5,731,307 A | 3/1998 | Desai | 514/217 |
| 6,525,048 B1 | 2/2003 | Bright | 514/233.2 |

FOREIGN PATENT DOCUMENTS

| | | | |
|---|---|---|---|
| EP | 1 177 792 | * | 2/2002 |
| WO | 9215580 | | 9/1992 |
| WO | WO 98/54181 | | 12/1998 |
| WO | 9952907 | | 10/1999 |
| WO | WO 00/15612 | | 3/2000 |
| WO | WO 00/17202 | | 3/2000 |
| WO | WO 00/17203 | | 3/2000 |
| WO | 0039128 | | 7/2000 |
| WO | WO 00/55139 | | 9/2000 |

OTHER PUBLICATIONS

Wermuth, C., "Molecular Variations Based on Isosteric Replacements" Chapter 13, pp. 203-237, from The Practice of Medicinal Chemistry © 1996 Academic Press Limited.*
Vippagunta et al, "Crystalline Solids" Advanced Drug Delivery Reviews, vol. 48, pp. 3-26 (2001).*
Gavezzotti, "Are Crystal Structures Predictable?" Accounts of Chemical Research, vol. 27, pp. 309-314 (1994).*
Janssen et al, "Pharmacology of Risperidone (R 64 766), a New Antipsychotic with Serotonin-S2 and Dopamine-D2 Antagonist Properties" The Journal of Pharmacology and Experimental Therapeutics vol. 244(2), pp. 685-693 (1988).*
Keks and Culhane "Risperidone (Risperdal): clinical experience with a new antipsychotic drug" Expert Opinion on Investigational Drugs, vol. 8(4), pp. 443-452 (1999).*
Hirota et al, "Neuropharmacological Profile of an Atypical Antipsychotic, NRA0562" CNS Drug Reviews, vol. 9(4), pp. 375-388 (2003).*

* cited by examiner

*Primary Examiner*—Zachary C Tucker
(74) *Attorney, Agent, or Firm*—Steve Zelson; Garth Butterfield; Mary J. Hosley

(57) ABSTRACT

An aminomethylpyridyloxymethyl/benzisoxazole substituted azabicyclic compound of formula I, pharmaceutical composition comprising same, and a method of treating one or more CNS or other disorders, including concurrent treatment of disorders such as schizophrenia and depression, wherein formula I is

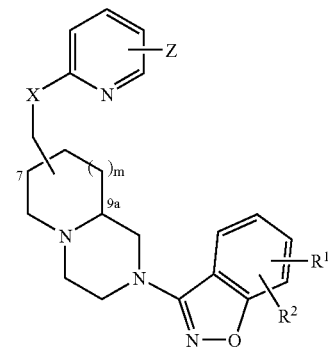

or a pharmaceutically acceptable salt or thereof, wherein Z is

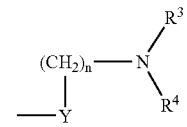

wherein Y is methylene; X is oxygen; n is 0; $R^1$ and $R^2$ are each hydrogen or halogen; and $R^3$ and $R^4$ together with the nitrogen atom to which they are attached form i) a saturated non-aromatic 3 to 7 membered monocyclic ring, said ring i) being unsubstituted or substituted or substituted with one or more $(C_1$–$C_4)$alkyl, $(C_1$–$C_4)$alkoxy$(C_1$–$C_4)$alkyl, or hydroxy groups.

14 Claims, No Drawings

PYRIDYLOXYMETHYL AND BENZISOXAZOLE AZABICYCLIC DERIVATIVES

This application claims priority under 35 USC 119(e) of U.S. Provisional 60/453,925, filed Mar. 12, 2003.

FIELD OF THE INVENTION

The invention pertains to aminomethylpyridyloxymethyl/ benzisoxazole substituted azabicyclic compounds that, among other things, can singly serve as an effective 5-HT1B, 5-HT2A and D2 receptor inhibitor, e.g. antagonist, inverse agonist and/or partial agonist. The invention also relates to an intermediate for preparation of said compounds; a pharmaceutical composition comprising said compounds; and the use of said compounds or other compounds having said effective 5-HT1B, 5-HT2A and D2 receptor binding or inhibition in a method for treating certain CNS or other disorders.

BACKGROUND OF THE INVENTION

Disorders of the Central Nervous System (CNS) can be medically treated in various ways. Of increasing importance in this regard are psychotropic drugs. But while such drugs have therapeutic effect, they also may cause unwanted and serious side effects. For example, schizophrenia can be treated with so-called typical drugs, which have been theorized to block certain dopamine (D2) receptors in the brain thought responsible for the positive symptoms of delusions, disordered thinking and the like. However, while these drugs can ameliorate some of the positive symptoms, they can also adversely affect the motor system, causing muscle problems such as spasms, cramps, tremors and Parkinsonism. Inasmuch as these types of side effects—generally characterized as Extrapyramidal Symptoms (EPS)—can be severe enough to disrupt daily activities, resort has been made to so-called atypical drugs.

Atypical antipsychotics have reduced incidents of EPS and can alleviate not only some of the positive symptoms of schizophrenia, but some of the negative symptoms as well, such as emotional unresponsiveness, social withdrawal and the like. Although antipsychotic drugs are believed to be more selective in their chemical effect on the brain, thereby reducing EPS, they too may have side effects. While these are not often as disruptive as those presented by typical drug therapy, they may nonetheless be of consequence to the patient. For example, atypical drugs can be sedating and can cause weight gain.

The situation is further complicated when several CNS disorders are present in a patient. For example, psychosis, such as schizophrenia, can often co-exist with depression, anxiety, obsessive-compulsive disorder (OCD) and other such illnesses. In such cases, treatment often entails the administration of a combination of drugs, e.g., one to treat schizophrenia and one to treat depression or other co-morbid CNS ailment. Because each such drug has its own side effects, the combined administration can lead to a multiplication or enhancement of same, all to the detriment of the patient. Moreover, it is theorized that a different brain receptor, or combination or permutation of receptors, are somehow implicated in each of the various CNS disorders; for example, schizophrenia has been thought to involve D2 and 5HT-2A receptors whereas depression has been associated with 5HT-1B receptors. A class of aminomethylphenoxymethyl/benzisoxazole substituted azabicyclic compounds, useful as selective agonists and antagonists of serotonin 1 (5-HT1) receptors, is described in WO 99/52907 to Bright.

It has hitherto proven difficult to find a single drug that can treat a patient suffering from diverse CNS disorders where a plurality of different receptors are in play. Accordingly, there is an on-going need for a psychotropic drug that has a pronounced reduction in side effects, and that can efficaciously and by itself treat multiple CNS disorders in which an antagonist or agonist to different receptors is indicated. Specifically, it would be desirable to find a drug that can concurrently treat schizophrenia and depression in which D2, 5HT-2A and 5HT-1B receptors are involved.

SUMMARY OF THE INVENTION

The present invention addresses the aforesaid needs. In one aspect, the invention relates to a compound having the following formula, denoted herein as Formula I:

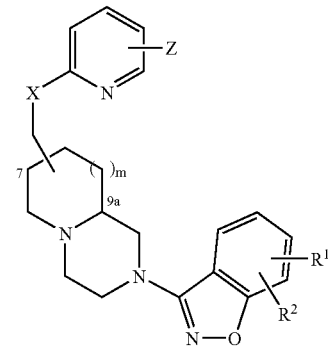

I or the (R) or (S) enantiomer thereof, or the cis or trans isomer thereof, or a pharmaceutically acceptable salt, solvate or prodrug thereof or of any of the foregoing, wherein m is 0 or 1; Z is

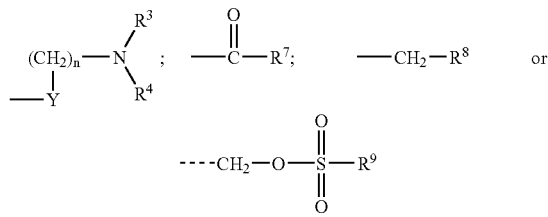

wherein $R^7$ is hydrogen or $(C_1-C_3)$alkoxy; $R^8$ is hydrogen, hydroxy, or $(C_1-C_3)$alkoxy; and $R^9$ is $(C_1-C_3)$alkoxy;

X is oxygen or NR, wherein R is hydrogen or $(C_1-C_6)$ alkyl;

Y is methylene, wherein n is 0, 1 or 2; or oxygen, nitrogen or sulfur, wherein n is 2, 3 or 4;

$R^1$ and $R^2$ are each independently hydrogen, halogen, or a $(C_1-C_6)$alkyl, $(C_1-C_6)$alkoxy or a $(C_1-C_6)$alkoxy$(C_1-C_6)$ alkyl group, any one of which groups may be unsubstituted or substituted with one or more halogens;

$R^3$ and $R^4$ are each independently hydrogen, a $(C_1-C_6)$ alkyl, a $(C_3-C_7)$cycloalkyl, or a 5 to 6 membered heterocyclic group, any one of which groups may be unsubstituted or substituted with one or more of any of the following:

$(C_1–C_4)$alkyl, $(C_3–C_7)$cycloalkyl, $(C_1–C_4)$alkoxy, $(C_6–C_{10})$aryl, a 5 to 6 member heterocyclic, amino, halogen or hydroxy groups; or $R^3$ and $R^4$ together with the nitrogen atom to which they are attached form:

(i) a 3 to 7 membered optionally unsaturated monocyclic ring; or (ii) a 4 to 10 membered optionally unsaturated polycyclic ring, wherein said monocyclic or polycyclic ring optionally has one or two additional heteroatoms selected from nitrogen, oxygen and sulfur, wherein any of said rings (i) or (ii) may be unsubstituted or substituted with one or more $(C_1–C_4)$alkyl, $(C_1–C_4)$alkoxy, $(C_1–C_4)$alkoxy$(C_1–C_4)$alkyl, $(C_3–C_7)$cycloalkyl, $(C_6–C_{10})$aryl, $(C_7$ to $C_{13})$aralkyl, a 5 to 10 membered heteroaryl, hydroxy, amino, cyano, or halogen groups.

In a particular embodiment, the compound of the invention has the formula:

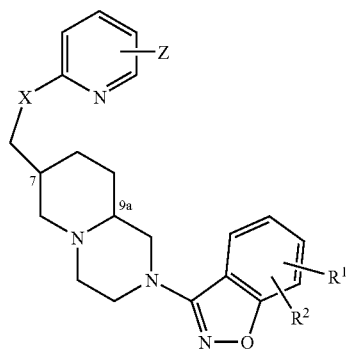

or the (R) or (S) enantiomer thereof, or the cis or trans isomer thereof, or a pharmaceutically acceptable salt, solvate or prodrug thereof or of any of the foregoing, wherein Z is

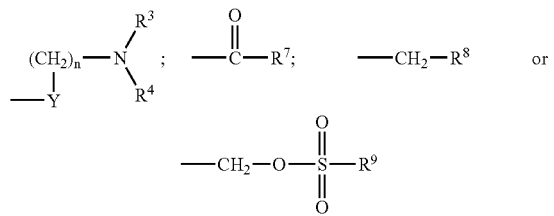

wherein $R^7$ is hydrogen or $(C_1–C_3)$alkoxy; $R^8$ is hydrogen, hydroxy, or $(C_1–C_3)$alkoxy; and $R^9$ is $(C_1–C_3)$alkoxy;

X is oxygen or NR, wherein R is hydrogen or $(C_1–C_6)$alkyl;

Y is methylene, wherein n is 0, 1 or 2; or oxygen, nitrogen or sulfur, wherein n is 2, 3 or 4;

$R^1$ and $R^2$ are each independently hydrogen, halogen, or a $(C_1–C_6)$alkyl, $(C_1–C_6)$alkoxy or a $(C_1–C_6)$alkoxy$(C_1–C_6)$alkyl group, any one of which groups may be unsubstituted or substituted with one or more halogens;

$R^3$ and $R^4$ are each independently hydrogen, a $(C_1–C_6)$alkyl, a $(C_3–C_7)$cycloalkyl, or a 5 to 6 membered heterocyclic group, any one of which groups may be unsubstituted or substitituted with one or more of any of the following: $(C_1–C_4)$alkyl, $(C_3–C_7)$cycloalkyl, $(C_1–C_4)$alkoxy, $(C_6–C_{10})$aryl, a 5 to 6 member heterocyclic, amino, halogen or hydroxy groups; or $R^3$ and $R^4$ together with the nitrogen atom to which they are attached form:

(i) a 3 to 7 membered optionally unsaturated monocyclic ring; or (ii) a 4 to 10 membered optionally unsaturated polycyclic ring, wherein said monocyclic or polycyclic ring optionally has one or two additional heteroatoms selected from nitrogen, oxygen and sulfur, wherein any of said rings (i) or (ii) may be unsubstituted or substituted with one or more $(C_1–C_4)$alkyl, $(C_1–C_4)$alkoxy, $(C_1–C_4)$alkoxy$(C_1–C_4)$alkyl, $(C_3–C_7)$cycloalkyl, $(C_6–C_{10})$aryl, $(C_7$ to $C_{13})$aralkyl, a 5 to 10 membered heteroaryl, hydroxy, amino, cyano, or halogen groups.

In other aspects, the invention relates to a pharmaceutical composition comprising said compound; and to a method of treating one or more CNS disorders wherein a ligand, for example, an antagonist, partial agonist (with 80% or more antagonism), or inverse agonist, to D2, 5HT-2A and 5HT-1B receptors, individually or any combination thereof, is indicated. The invention also pertains in part to a compound manifesting a ratio of D2:5HT1B receptor binding of about 20 or less; and/or inhibitory activity to each of said D2, 5HT1B and 5HT2A receptors.

Compounds of the invention have receptor binding activity to at least two and preferably all three of the D2, 5HT1B and 5HT2A receptors. The level of inhibition in this regard is such that the compound of the invention is therapeutically effective to treat CNS disorder(s) in a mammal wherein activity against all of these receptors, is indicated. This means that the compound has an effective Ki of less than or equal to 20 nM at all three receptors.

Furthermore, the invention preferably comprises any compounds with an intrinsic efficacy of an antagonist and/or inverse agonist at human D2, human 5HT1B and human 5HT2A receptors. The intrinsic efficacy as measured by adenylate cyclase activity, phosoinositol turnover, or other methods known in the art. No prior art compound displays antagonist or inverse agonist activity at all three receptors. More specifically, the invention preferably comprises compounds with an intrinsic efficacy of an antagonist and/or inverse agonist at human D2 and human 5HT2A receptors and an intrinsic efficacy of an antagonist >–80% at human 5HT1B receptors. As above, the intrinsic efficacy may be measured by adenylate cyclase activity or phosoinositol turnover.

The invention preferably comprises compounds with a functional Ki value at 5HT1B of less than or equal to 5 nM in combination with a functional Ki value of less than or equal to 20 nM at human D2 and human 5HT2A receptors Furthermore, the invention preferably comprises compounds that can singly show in vivo efficacy in animal models of 5HT1B, D2, and 5HT2A antagonism or inverse agonism. Representative animal models include the following examples but are not limited to such models. Compounds are tested for their ability to antagonize the hypothermia response produced by a 5-HT1B agonist as a measure of in vivo 5-HT1B antagonist activity. Compounds or vehicle are administered to guinea pigs, 0 to 60 minutes subcutaneous (sc) prior to the 5-HT1B agonist and body temperatures are monitored over a four hour period after agonist administration. The present invention preferably comprises compounds with an $ID_{50}$ of less than or equal to 1 mg/kg, sc in hypothermia.

In another animal model, compounds are tested for their ability to antagonize DOI (drug interaction)-induced head twitches as a measure of in vivo 5-HT2A antagonist activity. Administration of the 5-HT2A agonist, DOI, elicits a characteristic head shaking behavior (head twitch) that has been attributed to activation of 5-HT2A receptors. Compounds or vehicle are administered to habituated rats, 30 to 60 min sc prior to 3.2 mg/kg DOI, and head twitches are counted over a 30 min test period. The invention preferably comprises compounds with an $ID_{50}$ of less than or equal to 10 mg/kg, sc in 5HT2A head twitch.

In addition, compounds are tested for their ability to antagonize d-amphetamine-induced hyperactivity as a measure of in vivo dopamine D2 receptor antagonist activity. Administration of low doses of the indirect dopamine agonist, d-amphetamine, produces a dramatic increase in horizontal locomotor activity in rats, a phenomenon which has been attributed to activation of the mesolimbic dopamine system, and which therefore provides a rodent model of the hyperdopaminergic activity implicated in schizophrenia. Compounds or vehicle are administered to habituated rats, 30–60 min s.c. prior to 1.0 mg/kg of d-amphetamine $SO_4$, and locomotor activity data are recorded in computer-monitored activity chambers for the 3 hour duration of the hyperactivity response. The invention includes compounds with an $ID_{50}$ of less than or equal to 10 mg/kg, sc in d-amphetamine locomotor activity.

DETAILED DESCRIPTION OF THE INVENTION

In one embodiment, the invention is directed to a compound having inter alia binding activity to one or multiple receptors, including D2, 5HT1B and 5HT2A receptors, individually or any combination thereof. In preferred embodiment, the compound has binding activity (based on e.g. $IC_{50}$ or Ki) to D2 and 5HT1B receptors in a ratio of D2:5HT1B of about 20 or less; in more preferred practices, this ratio is about 10 or less; about 5 or less; most preferably about 1.

Unless otherwise indicated, the term "inhibitory activity" and related variations of same as used herein means that the compound serves, without limitation, as an antagonist, inverse agonist and/or partial agonist (80% antagonism or more) and the like to any of the receptors indicated herein; for example, the compound exhibits a binding affinity with a Ki of about 1 micromolar or less, with preferred practices having a Ki of about 100 nanomolar (nM) or less, about 50 nM or less, about 20 nM or less, and most preferably about 10 nM or less, for any of the receptors aforesaid.

In an exemplifying embodiment, the compound of the invention has Formula I, above, including pharmaceutically acceptable salts thereof, e.g. acid addition salts, base addition salts, and prodrugs and solvates thereof. Without limitation, examples of pharmaceutically acceptable acid addition salts of the compounds of Formula I are the salts of hydrochloric acid, p-toluenesulfonic acid, fumaric acid, citric acid, succinic acid, salicylic acid, oxalic acid, hydrobromic acid, phosphoric acid, methanesulfonic acid, tartaric acid, malate, di-p-toluoyl tartaric acid, and mandelic acid. Other possible acid addition salts are, e.g., salts containing pharmaceutically acceptable anions, such as the hydroiodide, nitrate, sulfate or bisulfate, phosphate or acid phosphate, acetate, lactate, gluconate, saccharate, benzoate, methanesulfonate, ethanesulfonate, benzenesulfonate, and pamoate (i.e., 1,1'-methylene-bis-(2-hydroxy-3-naphthoate) salts).

The compound of Formula I may have optical centers (e.g., at the 7 and 9a positions indicated) and thus may occur in different enantiomeric configurations. The invention includes all enantiomers, diastereomers, and other stereoisomers and optical isomers of such compound of Formula I, as well as racemic and other mixtures thereof. For example, the compound of Formula I includes (R) and (S) enantiomers and cis and trans isomers. The present invention further includes all radiolabelled forms of the compound of the Formula I. Preferred radiolabelled compounds are those wherein the radiolabels are selected from as $^3H$, $^{11}C$, $^{14}C$, $^{18}F$, $^{123}I$ and $^{125}I$. Such radiolabelled compounds are useful as research and diagnostic tools in metabolism pharmacokinetics studies and in binding assays in animals and man. In another embodiment, the invention is directed to a compound of Formula I wherein in an assay of D2, 5HT1B or 5HT2A binding said compound exhibits a Ki with intrinsic efficacy of about 1 micromolar or less; preferably exhibiting Ki's of about 100 nanomolar (nM) or less, about 50 nM or less, about 20 nM or less, and most preferably about 10 nM or less. The assays in this regard are those known in or adaptable from the art.

In a preferred embodiment, Z is

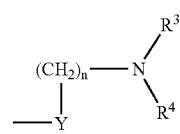

wherein X is oxygen; Y is methylene; n is 0; $R^1$ is hydrogen; $R^2$ is hydrogen or halogen; and $R^3$ is hydrogen or a $(C_1-C_3)$ alkyl. In another preferred embodiment, $R^2$ is hydrogen; $R^3$ is hydrogen; and $R^4$ is a) a $(C_1-C_6)$alkyl group; b) a $(C_3-C_7)$cycloalkyl group; or c) a 5 to 6 member heterocyclic group, any one of which groups a), b) or c) may be unsubstituted or substitituted with one or more of any of the following: $(C_1-C_4)$alkyl, $(C_3-C_7)$cycloalkyl, $(C_1-C_4)$ alkoxy, $(C_6-C_{10})$aryl, a 5 to 6 member heterocyclic, amino, halogen or hydroxy groups. More preferably, $R^4$ is a) a $(C_1-C_4)$alkyl which may be unsubstituted or substituted with one of the following: phenyl, cyclopropyl, methoxy, or substituted with a 5 to 6 membered heterocyclic, said heterocyclic having at least one nitrogen or oxygen atom; b) an unsubstituted $(C_3-C_7)$cycloalkyl; or c) a 5 to 6 membered heterocyclic which can be unsubstituted or substituted with a $(C_1-C_3)$alkyl or a $(C_1-C_3)$alkoxy, said 5 to 6 member heterocyclic c) having at least one nitrogen atom and up to one other heteroatom selected from nitrogen, oxygen and sulfur. Still more preferably, $R^4$ is a) an unsubstituted $C_4$ alkyl; a $C_3$ alkyl substituted with methoxy; a $(C_1-C_2)$alkyl substituted with phenyl or cyclopropyl; a $(C_1-C_2)$alkyl substituted with a 5 membered heterocyclic having a nitrogen or oxygen atom; or a $(C_1-C_2)$alkyl substituted with a 6 membered heterocyclic having at least one nitrogen; b) unsubstituted cyclopropyl; or c) a 5 to 6 membered heterocyclic which can be unsubstituted or substituted with a methyl or methoxy, said 5 to 6 membered heterocyclic c) having at least one nitrogen atom and up to one other heteroatom selected from nitrogen, oxygen and sulfur, said $(C_1-C_3)$alkyl is methyl and said $(C_1-C_3)$alkoxy is methoxy.

In another preferred embodiment, Z is

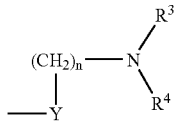

wherein X is oxygen; Y is methylene; n is 0; $R^3$ is $(C_1-C_3)$ alkyl; and $R^4$ is a) a $(C_1-C_4)$ alkyl group; or b) a $(C_5-C_6)$ cycloalkyl group, either of which groups a) or b) may be unsubstituted or substituted with one or more $(C_1-C_3)$ alkoxy or amino groups. Preferably, the amino group has the formula —$NR^5R^6$ wherein $R^5$ and $R^6$ are each independently hydrogen or $(C_1-C_4)$alkyl; more preferably, $R^4$ is a) a $(C_1-C_4)$alkyl group unsubstituted or substituted with one or more methoxy or amino groups wherein $R^5$ is hydrogen and $R^6$ is methyl; or b) an unsubstituted $(C_5-C_6)$cycloalkyl group.

In yet another preferred embodiment, Z is

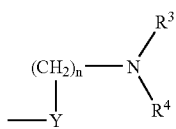

wherein X is oxygen; Y is methylene; n is 0; both $R^1$ and $R^2$ are each hydrogen or halogen; and $R^3$ and $R^4$ together with the nitrogen atom to which they are attached form i) a saturated 3 to 7 membered monocyclic ring, said ring i) being unsubstituted or substituted with one or more $(C_1-C_4)$ alkyl, $(C_1-C_4)$alkoxy$(C_1-C_4)$alkyl, or hydroxy groups. Alternatively, $R^3$ and $R^4$, together with the nitrogen atom to which they are attached, form an unsubstituted 5 to 6 membered ring which has one additional nitrogen, sulfur or oxygen atom. Alternatively, $R^1$ is hydrogen, $R^2$ is halogen; and $R^4$ is a) a $(C_1-C_5)$alkyl; b) a $(C_3-C_6)$ cycloalkyl group, any of which groups a) or b) can be unsubstituted or substituted with one or more of any of the following: cyclopropyl; halogen; hydroxy; a 5 to 6 membered heterocyclic group wherein said 5 to 6 membered heterocyclic group may be unsubstituted or substituted with one or more methyl groups; or phenyl wherein said phenyl may be unsubstituted or substituted with one or more halogens; or $R^4$ is c) a 5 member heterocyclic group. Preferably, $R^2$ is fluorine; and $R^3$ is hydrogen or methyl.

In another preferrred embodiment, Z is

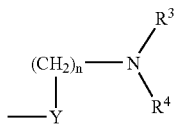

wherein X is oxygen; Y is methylene; n is 0; $R^1$ is hydrogen, $R^2$ is halogen; and $R^3$ and $R^4$ together with the nitrogen atom to which they are attached form i) a saturated 3 to 7 membered monocyclic ring, which monocylcic ring may be unsubstituted or substituted with one or more phenyl, $(C_1-C_3)$alkyl, or $(C_{1-4})$alkoxy$(C_{1-4})$alkyl groups; or ii) a 5 to 6 membered ring which may be unsubstituted or substituted with one or more $(C_1-C_3)$alkyl groups, and which has an additional nitrogen atom or oxygen atom.

In the compound of Formula I, in any ring formed by $NR^3R^4$: (a) there is not more than one ring oxygen atom; (b) no hydroxy, alkoxy, alkoxyalkyl, cyano, amino or alkylamino moiety bonded directly to any ring nitrogen atom; and (c) no ring carbon that is double bonded to another ring carbon and no part of an aromatic ring system can be bonded to a ring oxygen atom or ring nitrogen atom.

The present invention is also directed to a pharmaceutical composition comprising the compound of the invention; and a pharmaceutically acceptable carrier.

Unless otherwise indicated, the following terms and related variations of same as used herein representatively have the meanings ascribed:

"Halogen" and "halo" and the like includes fluoro, chloro, bromo and iodo.

"Alkyl" including as appears in the terms "alkoxy," "alkyoxyalkyl," and "aralkyl," includes saturated monovalent hydrocarbon radicals having straight or branched moieties. Examples of alkyl groups include, but are not limited to, methyl, ethyl, n-propyl, isopropyl, and t-butyl.

"Methylene" refers to the divalent radical —$(CH_2)_p$— where p is 1 (methylene), 2 (dimethylene) or 3 (trimethylene).

"Cycloalkyl" includes non-aromatic saturated cyclic alkyl moieties wherein alkyl is as defined above. Examples of cycloalkyl include, but are not limited to, cyclopropyl, cyclobutyl, cyclopentyl, cyclohexyl, and cycloheptyl; and bicycloalkyl and tricycloalkyl groups that are non-aromatic saturated carbocyclic groups consisting of two or three rings respectively, wherein said rings share at least one carbon atom. For purposes of the present invention, and unless otherwise indicated, bicycloalkyl groups include spiro groups and fused ring groups. Examples of bicycloalkyl groups include, but are not limited to, bicyclo-[3.1.0]-hexyl, bicyclo-2.2.1]-hept-1-yl, norbornyl, spiro[4.5]decyl, spiro [4.4]nonyl, spiro[4.3]octyl, and spiro[4.2]heptyl. An example of a tricycloalkyl group is adamantanyl. Cycloalkyl groups also include groups that are substituted with one or more oxo moieties. Examples of such groups with oxo moieties are oxocyclopentyl and oxocyclobutyl.

"Aryl" includes an organic radical derived from an aromatic hydrocarbon by removal of one hydrogen, such as phenyl, naphthyl, indenyl, indanyl, and fluorenyl; and fused ring groups wherein at least one ring is aromatic.

"Heterocyclic" refers to a cyclic group containing one or more heteroatoms, preferably from one to four heteroatoms, each selected from O, S and N. Heterocyclic groups also include ring systems substituted with one or more oxo moieties. Examples of heterocyclic groups are aziridinyl, azetidinyl, pyrrolidinyl, piperidinyl, azepinyl, piperazinyl, 1,2,3,6-tetrahydropyridinyl, oxiranyl, oxetanyl, tetrahydrofuranyl, tetrahydrothienyl, tetrahydropyranyl, tetrahydrothiopyranyl, morpholino, thiomorpholino, thioxanyl, pyrrolinyl, indolinyl, 2H-pyranyl, 4H-pyranyl, dioxanyl, 1,3-dioxolanyl, pyrazolinyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, quinolizinyl, quinuclidinyl, 1,4-dioxaspiro[4.5]decyl, 1,4-dioxaspiro[4.4]nonyl, 1,4-dioxa-spiro[4.3]octyl, and 1,4-dioxaspiro[4.2]heptyl.

"Heteroaryl" refers to aromatic groups containing one or more heteroatoms (O, S, or N), preferably from one to four heteroatoms. A multicyclic group containing one or more heteroatoms wherein at least one ring of the group is aromatic is a "heteroaryl" group. The heteroaryl groups of this invention can also include ring systems substituted with one or more oxo moieties. Examples of heteroaryl groups are pyridinyl, pyridazinyl, imidazolyl, pyrimidinyl, pyrazolyl, triazolyl, pyrazinyl, quinolyl, isoquinolyl, 1,2,3,4-tetrahydroquinolyl, tetrazolyl, furyl, thienyl, isoxazolyl, thiazolyl, oxazolyl, isothiazolyl, pyrrolyl, indolyl, benzimidazolyl, benzofuranyl, cinnolinyl, indazolyl, indolizinyl, phthalazinyl, triazinyl, 1,2,4-trizainyl, 1,3,5-triazinyl, isoindolyl, 1-oxoisoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl.

The foregoing groups, as derived from the compounds listed above, may be bonded via a C atom or N atom where such is possible. For instance, a group derived from pyrrole may be pyrrol-1-yl (bonded via N) or pyrrol-3-yl (bonded via C). The terms referring to the groups also encompass all possible tautomers.

"Amino" includes moieties of the formula —$NR^5R^6$ wherein $R^5$ and $R^6$ are each independently hydrogen or ($C_1$–$C_4$)alkyl.

"Treatment" and "treating" refers to reversing, alleviating, inhibiting the progress of, or preventing the disorder or condition to which such term applies, or one or more symptoms of such condition or disorder. As used herein, the term also encompasses, depending on the condition of the patient, preventing the disorder, including preventing onset of the disorder or of any symptoms associated therewith, as well as reducing the severity of the disorder or any of its symptoms prior to onset. "Treating" as used herein refers also to preventing a recurrence of a disorder. The term "treatment", as used herein, refers to the act of treating, as "treating" is defined immediately above.

For example, "treating schizophrenia, or schizophreniform or schizoaffective disorder" as used herein also encompasses treating one or more symptoms (positive, negative, and other associated features) of said disorders, for example treating, delusions and/or hallucination associated therewith. Other examples of symptoms of schizophrenia and schizophreniform and schizoaffecctive disorders include disorganized speech, affective flattening, alogia, anhedonia, inappropriate affect, dysphoric mood (in the form of, for example, depression, anxiety or anger), and some indications of cognitive dysfunction.

"Mammal" refers to any member of the class "Mammalia", including, but not limited to, humans, dogs, and cats.

"Modulating serotonergic neurotransmission" refers to increasing or improving, or decreasing or retarding the neuronal process whereby serotonin is released by a pre-synaptic cell upon excitation and crosses the synapse to stimulate or inhibit the post-synaptic cell.

"Chemical dependency" means an abnormal craving or desire for, or an addiction to a drug. Such drugs are generally taken by the affected individual by any of a variety of means, including oral, parenteral, nasal or by inhalation. Examples of chemical dependencies treatable by the methods of the present invention are dependencies on alcohol, nicotine, cocaine, heroin, phenolbarbitol, and benzodiazepines (e.g. Valium®). "Treating a chemical dependency" as used herein, means reducing or alleviating such dependency and/or the craving therefor.

The invention provides a method of treating one or more CNS disorders in a mammal, including a human, in need of such treatment. Without limitation, CNS disorders in this regard are those wherein a ligand to D2, 5HT1B and 5HT2A receptors, individually or in any combination, is indicated. In one aspect, the method comprises administering a therapeutically effective amount of a compound that is an inhibitor to at least two of the following receptors: D2, 5HT-1B and 5HT2A. In another aspect of the invention, the method comprises administering a therapeutically effective amount of a D2/5HT1-B/5HT-2A inhibitor. In yet another aspect, the method comprises administering a therapeutically effective amount of a D2/5HT1B inhibitor having a ratio of D2:5HT1B inhibitory activity of about 20 or less, it being preferred that said ratio is about 10 or less; about 5 or less; and most preferably about 1. In a preferred practice, the inhibitor administered for treatment pursuant to the method of the invention has the structure of Formula I.

CNS disorders subject of the invention are those known in the art; and include without limitation those wherein a ligand, e.g. an antagonist, an inverse agonist and/or a partial agonist and the like, to D2, 5HT1B, and 5HT2A receptors, either individually or any combinations thereof, are indicated. Thus in a preferred practice, the invention can treat one or more CNS disorders with a single compound; for example, the invention can treat schizophrenia, wherein inhibition of D2 and 5HT2A receptors is commonly indicated, and depression wherein inhibition of 5HT1B receptors is commonly indicated.

The compound of the invention can also be used in combination with other drugs, e.g. those conventionally used to treat any of the CNS disorders herein described. For example, the compound of the invention can be used in combination with ziprasidone and like compounds to treat schizophrenia; or with a 5HT re-uptake inhibitor and like compounds to treat depression.

CNS disorders contemplated for treatment by the present invention include, without limitation:

Anxiety or psychotic disorders such as: schizophrenia, for example of the paranoid, disorganized, catatonic, undifferentiated, or residual type; schizophreniform disorder; schizoaffective disorder, for example of the delusional type or the depressive type; delusional disorder; substance-induced psychotic disorder, for example psychosis induced by alcohol, amphetamine, cannabis, cocaine, hallucinogens, inhalants, opioids, or phencyclidine; personality disorder of the paranoid type; and personality disorder of the schizoid type. Examples of anxiety disorders include, but are not limited to, panic disorder; agoraphobia; a specific phobia; social phobia; obsessive-compulsive disorder; post-traumatic stress disorder; acute stress disorder; and generalized anxiety disorder.

Movement disorders involving: Huntington's disease and dyskinesia associated with dopamine agonist therapy; Parkinson's disease and restless leg syndrome.

Chemical dependencies: for example alcohol, amphetamine, cocaine, opiate, nicotine addiction.

Disorders comprising, as a symptom thereof, a deficiency in cognition: for example, a subnormal functioning in one or more cognitive aspects such as memory, intellect, or learning and logic ability, in a particular individual relative to other individuals within the same general age population. Also, any reduction in any particular individual's functioning in one or more cognitive aspects, for example as occurs in age-related cognitive decline. Examples of disorders that comprise as a symptom a deficiency in cognition that can be treated according to the present invention are dementia, for example Alzheimer's disease, multi-infarct dementia, alcoholic dementia or other drug-related dementia, dementia associated with intracranial tumors or cerebral trauma, dementia associated with Huntington's disease or Parkinson's disease, or AIDS-related dementia; Alzheimer's related dementia; delirium; amnestic disorder; post-traumatic stress disorder; mental retardation; a learning disorder, for example reading disorder, mathematics disorder, post operative cognitive decline, or a disorder of written expression; attention-deficit/hyperactivity disorder; and age-related cognitive decline.

Mood disorders or mood episodes such as: major depressive episode of the mild, moderate or severe type, a manic or mixed mood episode, a hypomanic mood episode; a depressive episode with atypical features; a depressive episode with melancholic features; a depressive episode with catatonic features; a mood episode with postpartum onset; post-stroke depression; major depressive disorder; dysthymic disorder; minor depressive disorder; treatment resistant depression, SSRI-resistant depression, premenstrual dysphoric disorder; post-psychotic depressive disorder of schizophrenia; a major depressive disorder superimposed on a psychotic disorder such as delusional disorder or schizophrenia; a bipolar disorder, for example bipolar I disorder, bipolar II disorder, and cyclothymic disorder. Other CNS disorders involved treatment resistant depression, SSR1 failures, autism and post operative decline.

Other disorders subject to treatment by the invention and which are affected by inhibition of any or all of the D2, 5HT1B, and 5HT2A receptors include those selected from: hypertension, autism, depression (e.g. depression in cancer patients, depression in Parkinson's patients, postmyocardial infarction depression, subsyndromal symptomatic depression, depression in infertile women, pediatric depression, major depression, single episode depression, recurrent depression, child abuse induced depression, and post partum depression), generalized anxiety disorder, phobias (e.g. agoraphobia, social phobia and simple phobias), posttraumatic stress syndrome, avoidant personality disorder, premature ejaculation, eating disorders (e.g. anorexia nervosa and bulimia nervosa), obesity, chemical dependencies (e.g. addictions to alcohol, cocaine, heroin, phenobarbital, nicotine and benzodiazepines), cluster headache, migraine, pain, Alzheimer's disease, obsessive-compulsive disorder, panic disorder, memory disorders (e.g. dementia, amnestic disorders, and age-related cognitive decline (ARCD), Parkinson's diseases (e.g. dementia in Parkinson's disease, neuroleptic-induced parkinsonism and tardive dyskinesias), endocrine disorders (e.g. hyperprolactinaemia), vasospasm (particularly in the cerebral vasculature), cerebellar ataxia, gastrointestinal tract disorders (involving changes in motility and secretion), negative symptoms of schizophrenia, schizoaffective disorder, obsessive compulsive disorder, mania, premenstrual syndrome, fibromyalgia syndrome, stress incontinence, Tourette's syndrome, trichotillomania, kleptomania, male impotence, cancer (e.g. small cell lung carcinoma), chronic paroxysmal hemicrania and headache (associated with vascular disorders).

The present invention also relates to a method for treating a disorder or condition treatable by modulating serotonergic neurotransmission in a mammal, preferably a human, comprising administering to a mammal in need of such treatment a therapeutically effective amount of a compound of the invention, including preferably the compound of Formula I.

Other disorders and conditions subject to treatment by the present invention are delineated in WO 99/52907 to Bright, the disclosure of which is incorporated herein by reference thereto.

The present invention also relates to a pharmaceutical composition for treating the aforesaid disorders/conditions, among others, comprising a therapeutically effective amount of a compound of the invention, including preferably the compound defined by Formula I and a pharmaceutically acceptable carrier.

Examples of preferred compounds of the Formula I are those having the absolute stereochemical configuration defined as (7R,9aS)-trans or as (7S,9aS)-cis.

Examples of specific embodiments of compounds of the Formula I are those set forth in Examples 1–110.

In another more specific embodiment, the invention relates to a compound of Formula I' as follows:

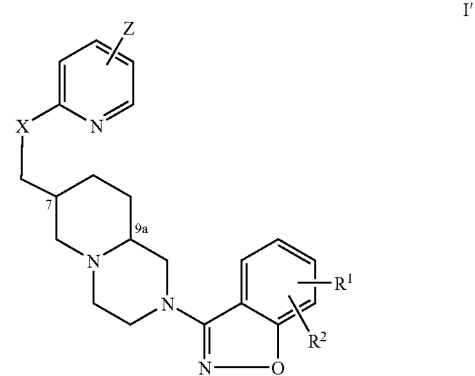

as a racemate, or the (R) and (S) enantiomers thereof, or the cis and trans isomers thereof, wherein X is oxygen or NR, wherein R is hydrogen or $(C_1-C_6)$alkyl;

$R^1$ and $R^2$ are each independently as hereinbefore defined and

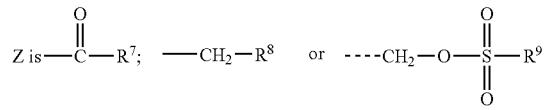

wherein $R^7$ is hydrogen or $(C_1-C_3)$alkoxy; $R^8$ is hydrogen, hydroxy, or $(C_1-C_3)$alkoxy; and $R^9$ is $(C_1-C_3)$alkyl.

Compounds of Formula I' are particularly useful in the synthesis of compounds of the Formula I. Examples of specific compounds of the Formula I' are the following and apply to all enantiomers and stereoisomers of the compounds:

(7R,9aS)-trans-6-(2-Benzo[d]isoxazol-3-yl-octahydro-pyrido[1,2-a]pyrazin-7-ylmethoxy)-nicotinic acid methyl ester;

(7R,9aS)-trans-[6-(2-Benzo[d]isoxazol-3-yl-octahydro-pyrido[1,2-a]pyrazin-7-ylmethoxy)-pyridin-3-yl]-methanol;

(7R,9aS)-trans-Methanesulfonic acid 6-(2-benzo[d]isoxazol-3-yl-octahydro-pyrido[1,2-a]pyrazin-7-ylmethoxy)-pyridin-2-ylmethyl ester;

(7R,9aS)-trans-Methanesulfonic acid 6-[2-(5-fluoro-benzo[d]isoxazol-3-yl)-octahydro-pyrido[1,2-a]pyrazin-7-ylmethoxy]-pyridin-2-ylmethyl ester;

(7R,9aS)-trans-6-(2-Benzo[d]isoxazol-3-yl-octahydro-pyrido[1,2-a]pyrazin-7-ylmethoxy)-pyridine-2-carboxylic acid methyl ester;

(7R,9aS)-trans-[6-(2-Benzo[d]isoxazol-3-yl-octahydro-pyrido[1,2-a]pyrazin-7-ylmethoxy)-pyridin-2-yl]-methanol;

(7R,9aS)-trans-{6-[2-(5-Fluoro-benzo[d]isoxazol-3-yl)-octahydro-pyrido[1,2-a]pyrazin-7-ylmethoxy]-pyridin-2-yl}-methanol;

(7R,9aS)-trans-6-[2-(5-Fluoro-benzo[d]isoxazol-3-yl)-octahydro-pyrido[1,2-a]pyrazin-7-ylmethoxy]-pyridine-2-carboxylic acid methyl ester;

(7S,9aS)-cis-6-(2-Benzo[d]isoxazol-3-yl-octahydro-pyrido[1,2-a]pyrazin-7-ylmethoxy)-pyridine-2-carboxylic acid methyl ester;

(7S,9aS)-cis-[6-(2-Benzo[d]isoxazol-3-yl-octahydro-pyrido[1,2-a]pyrazin-7-ylmethoxy)-pyridin-2-yl]-methanol;

(7S,9aS)-cis-Methanesulfonic acid 6-(2-benzo[d]isoxazol-3-yl-octahydro-pyrido[1,2-a]pyrazin-7-ylmethoxy)-pyridin-2-ylmethyl ester;

(7R,9aS)-trans-5-(2-Benzo[d]isoxazol-3-yl-octahydro-pyrido[1,2-a]pyrazin-7-ylmethoxy)-pyridine-2-carboxylic acid methyl ester;

(7R,9aS)-trans-[5-(2-Benzo[d]isoxazol-3-yl-octahydro-pyrido[1,2-a]pyrazin-7-ylmethoxy)-pyridin-2-yl]-methanol; and (7R,9aS)-trans-Methanesulfonic acid 5-(2-benzo[d]isoxazol-3-yl-octahydro-pyrido[1,2-a]pyrazin-7-ylmethoxy)-pyridin-2-ylmethyl ester.

The following Schemes 1–5 illustrate, without limitation, representative ways to prepare compounds of Formula I. It will be appreciated that other methodology or variations may be employed and are contemplated.

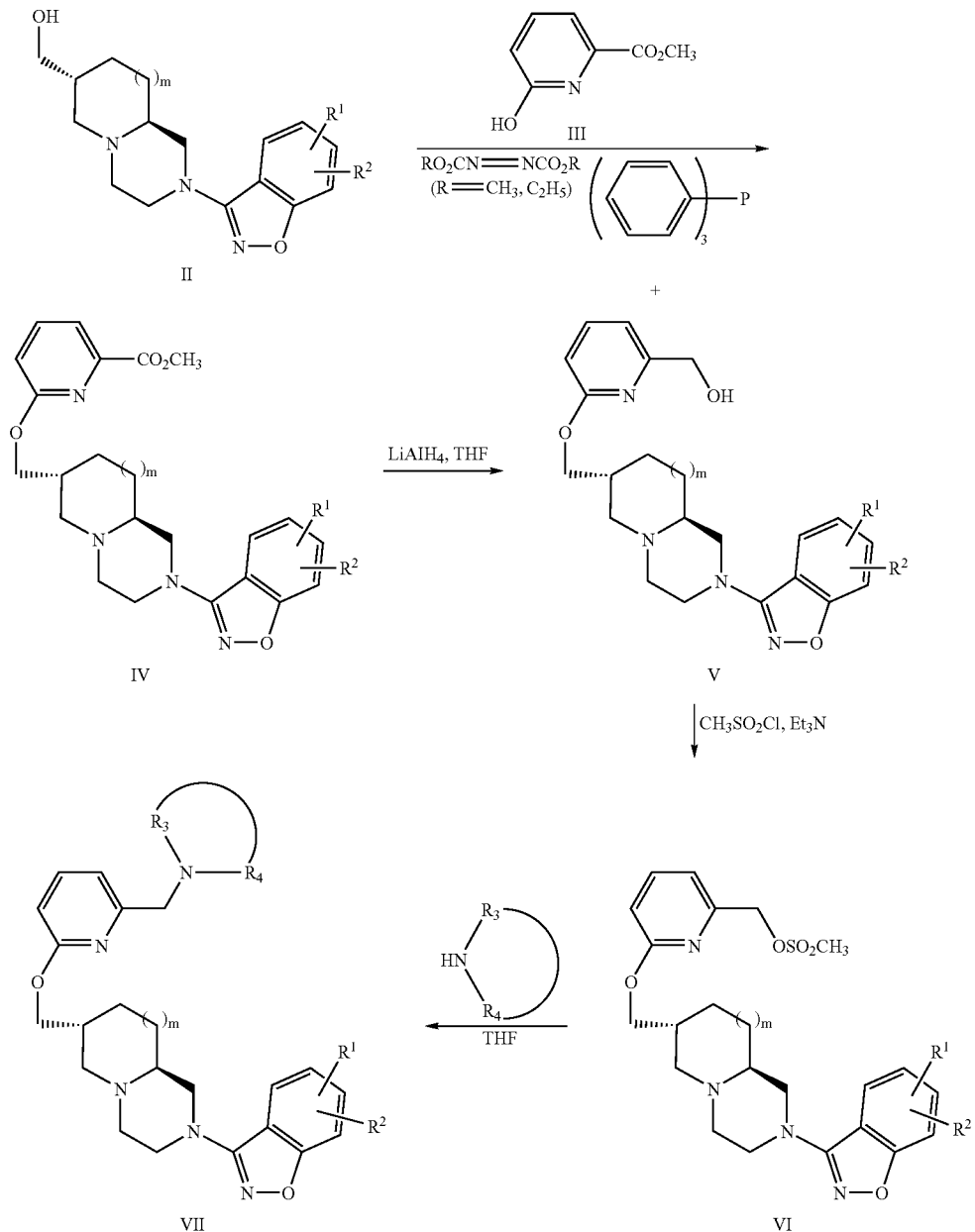

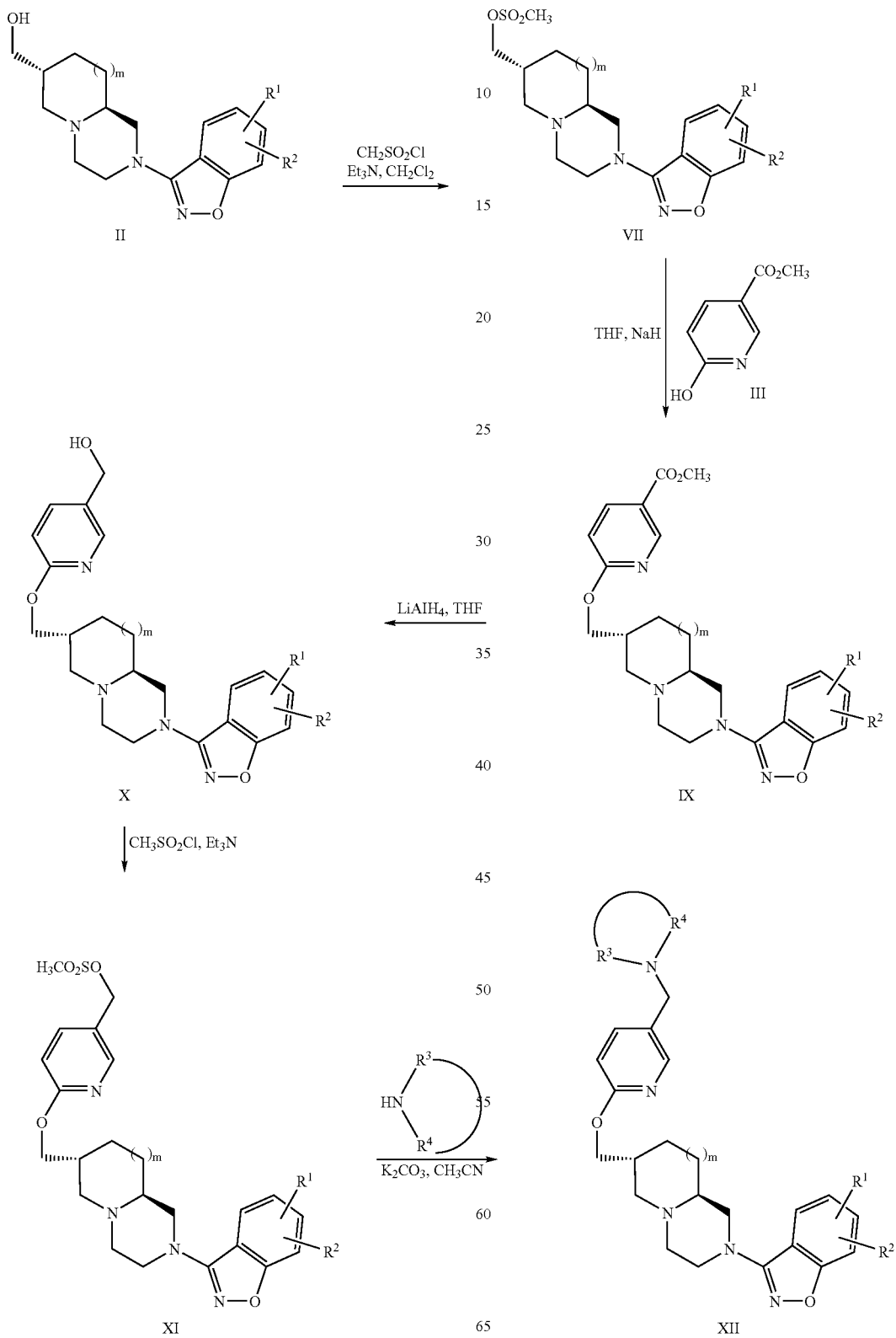

SCHEME 3
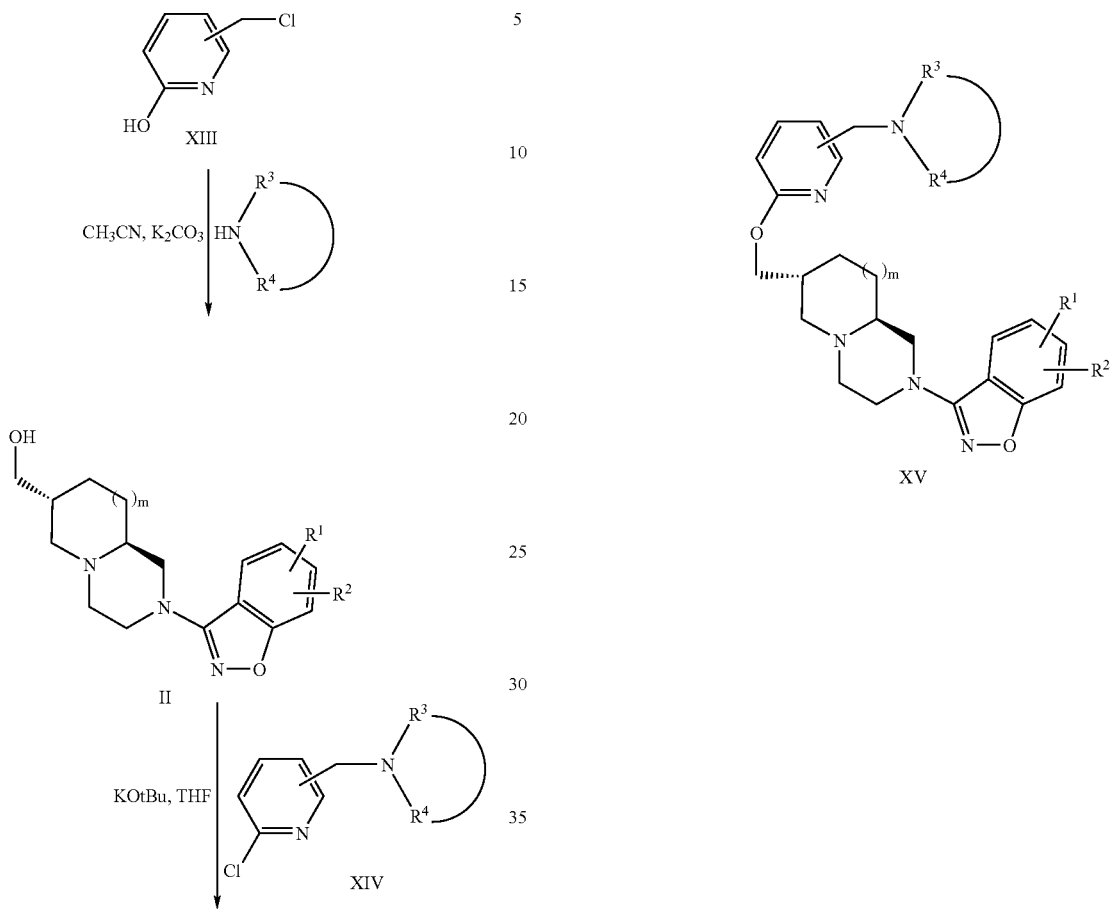
SCHEME 4
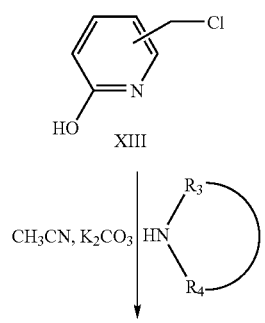

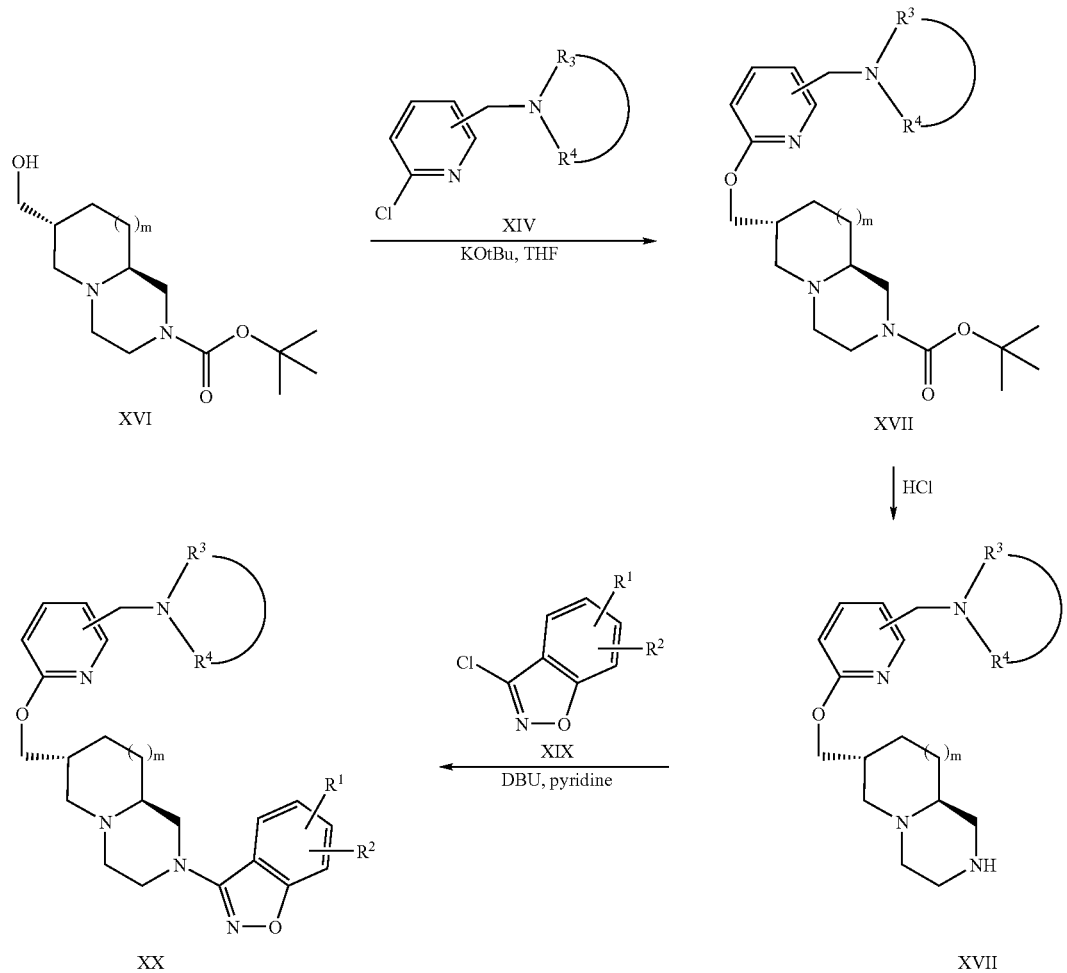
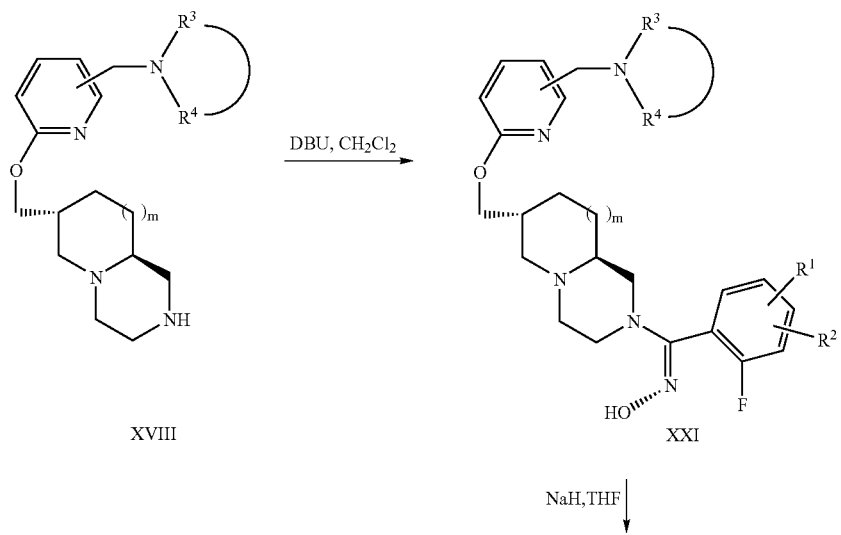
SCHEME 5

-continued

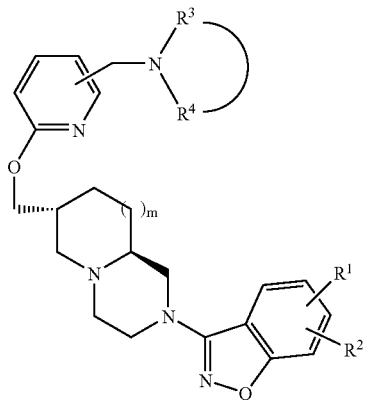

XX

Scheme 1 illustrates a method of preparing compounds of Formula I having the (7R, 9aS)-trans or (7S,9aS)-cis stereochemistry. Compounds with a (7S,9aR) stereochemistry may also be prepared using analogs of said method or the other methods illustrated. Referring to Scheme 1, the known compound Formula II (e.g. Bright WO 99/52907) is combined with the compound of Formula III, under Mitsunobu coupling conditions, in the presence of triphenylphosphine and a compound of the formula $RO_2CN=NCO_2R$ wherein R is methyl or ethyl, to form the compound of Formula IV. (See O. Mitsunobu, *Synthesis*, 1 (1981)). Suitable solvents for this reaction include tetrahydrofuran (THF), other ethers and halocarbon solvents, with THF being preferred. This reaction is generally conducted at a temperature from about room temperature to about 65° C., for about 1 to about 24 hours. It is preferably conducted at about 50° C. for about 4 to 18 hours.

Reduction of the compound of Formula IV yields the compound of Formula V. This reduction can be accomplished using lithium aluminum hydride or other aluminum hydrides as the reducing agent, in a solvent selected from, diethyl ether and other dialkyl ethers, preferably diethyl ether, at a temperature from about −5° C. to about room temperature, for about 0.5 to about 18 hours.

The compound of Formula V can then be converted into the compound of Formula VI by reacting it with methanesulfonyl chloride, in the presence of a tertiary amine base such as triethylamine (TEA), in methylene chloride or another halocarbon solvent, at a temperature from about −5° C. to about room temperature, for a period of about 10 minutes to about 2 hours.

Reaction of the resulting compound of Formula VI with a compound of the formula $HNR^3R^4$, wherein $R^3$ and $R^4$, together with the nitrogen to which they are attached, form a ring as depicted in Scheme 1, yields the corresponding compound having Formula VII. Typically, this last reaction is carried out in THF, N,N-dimethylformamide (DMF) or acetonitrile, or a mixture of two or more or the foregoing solvents, at a temperature from about room temperature to about 100° C., for a period from 1 to about 18 hours.

Scheme 2 illustrates a method of preparing compounds of Formula I having the (7R, 9aS)-trans or (7S,9aS)-cis stereochemistry. Referring to Scheme 2, the compound of Formula II can be converted into the compound of Formula VIII by reacting it with methanesulfonyl chloride, in the presence of a tertiary amine base such as triethylamine (TEA), in methylene chloride or another halocarbon solvent, at a temperature from about −5° C. to about room temperature, for a period of about 10 minutes to about 2 hours. The compound Formula VIII is combined with the compound of Formula III, under basic coupling conditions to form the compound of Formula IX. Suitable bases include sodium hydride, potassium hydride, alkyl lithiums, sodium bistrimethylsilylamides. Suitable solvents for this reaction include tetrahydrofuran (THF), other ethers, dimethylformamide, and N-methylpyrrolidinone (NMP), with NMP being preferred. This reaction is generally conducted at a temperature from about room temperature to about 100° C., for about 1 to about 24 hours. It is preferably conducted between about 70° C. and about 100° C. Generally, the reaction is run for a period for about 1 to 24 hours.

Reduction of the compound of Formula IX yields the compound of Formula X. This reduction can be accomplished using lithium aluminum hydride as the reducing agent, in a solvent selected from, diethyl ether and other dialkyl ethers, preferably diethyl ether, at a temperature from about −5° C. to about room temperature, for about 0.5 to about 18 hours.

The compound of Formula X can then be converted into the compound of Formula XI by reacting it with methanesulfonyl chloride, in the presence of a tertiary amine base such as triethylamine (TEA), in methylene chloride or another halocarbon solvent, at a temperature from about −5° C. to about room temperature, for a period of about 10 minutes to about 2 hours.

Reaction of the compound of Formula XI with a compound of the formula $HNR^3R^4$ wherein $R^3$ and $R^4$, together with the nitrogen to which they are attached, form a ring, as depicted in Scheme 2, yields the corresponding compound having Formula XII. Typically, this reaction is carried out in THF, N,N-dimethylformamide (DMF) or acetonitrile, or a mixture of two or more or the foregoing solvents, at a temperature from about room temperature to about 100° C., for a period from 1 to about 18 hours.

Scheme 3 illustrates a method of preparing compounds of the Formula I having the (7R,9aS)-trans or (7S,9aS)-cis stereochemistry. Referring to Scheme 3, the compound of Formula II can be converted into the compound of Formula XV by reacting it with a compound of Formula XIV with a suitable base such as potassium t-butoxide in tetrahydrofuran, other ethers, or dimethylformamide, or halocarbon solvents. Suitable bases include sodium hydride, potassium hydride, alkyl lithiums, sodium bistrimethylsilylamides. This reaction is generally conducted at a temperature from about room temperature to about 80° C., for about 1 to about 24 hours. It is preferably conducted at about 60° C. for about 1 to 12 hours. Compound of the Formula XIV can be prepared from compound of Formula XIII using a compound of the formula HNR³R⁴ wherein R³ and R⁴, together with the nitrogen to which they are attached, form a ring, as depicted in Scheme 3, and a base such as potassium carbonate in a solvent such as acetonitrile. Suitable solvents for this reaction include tetrahydrofuran (THF), other ethers, dimethylformamide, and halocarbon solvents, with acetonitrile being preferred. Suitable bases include sodium hydride, potassium carbonate, sodium carbonate, alkyl lithiums, sodium or lithium bistrimethylsilylamides, LDA. This reaction is generally conducted at a temperature from about room temperature to about 80° C., for about 1 to about 24 hours. It is preferably conducted at about 60° C. for about 1 to 12 hours.

Scheme 4 illustrates a method of preparing compounds of the Formula I having the (7R,9aS)-trans or (7S,9aS)-cis stereochemistry. Referring to Scheme 4, the compound of Formula XVI can be converted into the compound of Formula XVII by reacting it with compound of Formula XIV with a suitable base such as potassium t-butoxide in tetrahydrofuran, other ethers, or dimethylformamide, or halocarbon solvents. Suitable bases include sodium hydride, potassium hydride, alkyl lithiums, sodium bistrimethylsilylamides. This reaction is generally conducted at a temperature from about room temperature to about 80° C., for about 1 to about 24 hours. It is preferably conducted at about 60° C. for about 1 to 12 hours. Compound of the Formula XIV can be prepared from compound of Formula XIII using a compound of the formula HNR³R⁴ wherein R³ and R⁴, together with the nitrogen to which they are attached, form a ring, as depicted in Scheme 4, and a base such as potassium carbonate in a solvent such as acetonitrile. Suitable solvents for this reaction include tetrahydrofuran (THF), other ethers, dimethylformamide, and halocarbon solvents, with acetonitrile being preferred. This reaction is generally conducted at a temperature from about room temperature to about 80° C., for about 1 to about 24 hours. It is preferably conducted at about 60° C. for about 1 to 12 hours.

The compound of Formula XVII is then deprotected to form the hydrochloric acid addition salt of the corresponding compound of Formula XVIII. This can be accomplished using anhydrous hydrochloric acid (HCl) in diethyl ether, another dialkyl ether or a halocarbon solvent at about room temperature. This reaction can also be carried out without a solvent using trifluoroacetic acid, in which case the bitrifluoroacetic acid addition salt is formed. This reaction is generally run from about 2 to about 18 hours.

The desired corresponding compound of Formula XX can be formed by reacting the compound of Formula XVIII from the foregoing reaction with the appropriate compound of Formula XIX wherein R¹ and R² are as defined above for Formula I, and 1,8-diazabicyclo[5.4.0]-undec-7-ene (DBU). This reaction is typically conducted in pyridine, at a temperature from about 50° C. to about 110° C., for a period of about 1 to about 48 hours.

Scheme 5 is an alternate method of preparing compounds of a Formula I having the same stereochemistry at positions 7 and 9a as compounds of the Formula XX and wherein the aminomethyl sidechain on the phenoxy group can be attached at any position (i.e. ortha, meta or para) of that group. Referring to Scheme 5, the dihydrochloride salt of the appropriate compound of the Formula XVIII is reacted with syn, anti, or a mixture of the syn and anti isomers of a compound of the formula

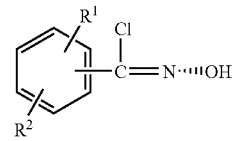

(i.e. the appropriately substituted benzohydroximinoyl chloride), in the presence of a base such as DBU, to form the corresponding compound of Formula XXI. Suitable solvents for this reaction include chlorohydrocarbons such as chloroform and methylene chloride. Suitable reaction temperatures range from about −78° C. to about 50° C. This reaction is preferably conducted at a temperature from about 20° C. to about 40° C., for a period of about 0.5 to about 24 hours.

The resulting compound of Formula XXI can then be converted into the desired final product of Formula XX by reacting it with a strong nucleophilic organic base (e.g. n-butyl lithium) or sodium hydride. This reaction is typically conducted in a solvent such as toluene, DMF or THF, at a temperature from about room temperature to about 110° C. for about 1 to 48 hours. Preferably, the solvent is a mixture of toluene and THF and the reaction is carried out at a temperature from about 80° C. to about 100° C.

Unless indicated otherwise, the pressure conditions of each of the above reactions is not critical. Generally, the reactions will be conducted at a pressure of about one to about three atmospheres, preferably at about ambient pressure (about one atmosphere).

The compounds of Formula I which are basic in nature are capable of forming a wide variety of different salts with various inorganic and organic acids. Although such salts must be pharmaceutically acceptable for administration to animals, it is often desirable in practice to initially isolate a compound of the Formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, e.g. salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate, i.e., 1,1'-methylene-bis-(2-hydroxy-3-naphthoate), salts.

The compound of Formula I may advantageously be used in conjunction with one or more other therapeutic agents, for instance, different antidepressant agents such as tricyclic antidepressants (e.g. amitriptyline, dothiepin, doxepin, trimipramine, butripyline, clomipramine, desipramine, imipramine, iprindole, lofepramine, nortriptyline or protriptyline), monoamine oxidase inhibitors (e.g. isocarboxazid, pheneizine or tranylcyclopramine) or 5-HT re-uptake inhibitors (e.g. fluvoxamine, sertraline, fluoxetine or paroxetine), and/or with antiparkinsonian agents such as dopaminergic antiparkinsonian agents (e.g. levodopa, preferably in combination with a peripheral decarboxylase inhibitor e.g., benserazide or carbidopa, or with a dopamine agonist e.g., bromocriptine, lysuride or pergolide). It may also be used with acetocholinesterases such as donepezil. It is to be understood that the present invention covers the use of a compound of Formula I or a physiologically acceptable salt or solvate thereof in combination with one or more other therapeutic agents.

The compound of Formula I and the pharmaceutically acceptable salts thereof, in combination with a 5-HT re-uptake inhibitor (e.g. fluvoxamine, sertraline, fluoxetine or paroxetine), preferably sertraline, or a pharmaceutically acceptable salt or polymorph thereof (the combination of a compound of Formula I with a 5-HT re-uptake inhibitor is referred herein to as "the active combination"), are useful psychotherapeutics and may be used in the treatment or prevention of disorders the treatment or prevention of which is facilitated by modulating serotonergic neurotransmission such as hypertension, depression (e.g. depression in cancer patients, depression in Parkinson's patients, postmyocardial infarction depression, subsyndromal symptomatic depression, depression in infertile women, pediatric depression, major depression, single episode depression, recurrent depression, child abuse induced depression, and post partum depression), generalized anxiety disorder, phobias (e.g. agoraphobia, social phobia and simple phobias), posttraumatic stress syndrome, avoidant personality disorder, premature ejaculation, eating disorders (e.g. anorexia nervosa and bulimia nervosa), obesity, chemical dependencies (e.g. addictions to alcohol, cocaine, heroin, phenobarbital, nicotine and benzodiazepines), cluster headache, migraine, pain, Alzheimer's disease, obsessive-compulsive disorder, panic disorder, memory disorders (e.g. dementia, amnestic disorders, and age-related cognitive decline (ARCD)), Parkinson's diseases (e.g. dementia in Parkinson's disease, neuroleptic-induced parkinsonism and tardive dyskinesias), endocrine disorders (e.g. hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, fibromyalgia syndrome, stress incontinence, Tourette's syndrome, trichotillomania, kleptomania, male impotence, cancer (e.g. small cell lung carcinoma), chronic paroxysmal hemicrania and headache (associated with vascular disorders).

Serotonin (5-HT) re-uptake inhibitors, preferably sertraline, exhibit positive activity against depression; chemical dependencies; anxiety disorders including panic disorder, generalized anxiety disorder, agoraphobia, simple phobias, social phobia, and post-traumatic stress disorder; obsessive-compulsive disorder; avoidant personality disorder and premature ejaculation in mammals, including humans, due in part to their ability to block the synaptosomal uptake of serotonin.

Sertraline, (1S-cis)-4-(3,4-dichlorophenyl)-1,2,3,4-tetrahydro-N-methyl-1-naphthalenamine, has the chemical formula $C_{17}H_{17}NC_{12}$; its synthesis is described in U.S. Pat. No. 4,536,518 incorporated herein by reference. Sertraline hydrochloride is useful as an antidepressant and anorectic agent, and is also useful in the treatment of depression, chemical dependencies, anxiety obsessive compulsive disorders, phobias, panic disorder, post traumatic stress disorder, and premature ejaculation.

Activity of the active combination as antidepressants and related pharmacological properties can be determined by methods (1)–(4) below, which are described in Koe, B. et al., *Journal of Pharmacology and Experimental Therapeutics*, 226 (3), 686–700 (1983). Specifically, activity can be determined by studying (1) their ability to affect the efforts of mice in escaping a swim-tank (Porsolt mouse "behavior despair" test), (2) their ability to potentiate 5-hydroxytryptophan-induced behavioral symptoms in mice in vivo, (3) their ability to antagonize the serotonin-depleting activity of p-chloroamphetamine hydrochloride in rat brain in vivo, and (4) their ability to block the uptake of serotonin, norepinephrine and dopamine by synaptosomal rat brain cells in vitro. The ability of the active combination to counteract reserpine hypothermia in mice in vivo can be determined according to the methods described in U.S. Pat. No. 4,029,731.

The compound of the invention may be administered either alone or in combination with pharmaceutically acceptable carriers, in either single or multiple doses. Suitable pharmaceutical carriers include inert solid diluents or fillers, sterile aqueous solutions and various organic solvents. The pharmaceutical compositions formed thereby can then be readily administered in a variety of dosage forms such as tablets, powders, lozenges, liquid preparations, syrups, injectable solutions and the like. These pharmaceutical compositions can optionally contain additional ingredients such as flavorings, binders, excipients and the like. Thus, the compound of the invention may be formulated for oral, buccal, intranasal, parenteral (e.g. intravenous, intramuscular or subcutaneous), transdermal (e.g. patch) or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g. pregelatinized maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycolate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

For buccal administration, the composition may take the form of tablets or lozenges formulated in conventional manner.

The compound of the invention may be formulated for parenteral administration by injection, including using conventional catheterization techniques or infusion. Formulations for injection may be presented in unit dosage form, e.g. in ampules or in multi-dose containers, with an added preservative. They may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g. sterile pyrogen-free water, before use.

In a further aspect, this invention provides compositions of matter suitable for administration to a human patient as a solution (e.g., as an injectable or intranasally), comprising an inclusion complex of a salt of the compounds of the invention in a material such as cyclodextrin. Advantageously, in a preferred embodiment said inclusion complex provides an amount of compound of at least 2.5 mgA/ml when the amount of compound provided by said complex is measured at a cyclodextrin concentration of 40% w/v in water. The inclusion complex of compound in cyclodextrin can first be isolated by drying, usually by lyophilization. The isolated dry inclusion complex can be stored at room temperature for periods up to two years and longer, and reconstituted into a product solution as needed. When a product solution is required, it can be made by dissolving the isolated inclusion complex in water (or other aqueous medium) in an amount sufficient to generate a solution of the required strength for oral or parenteral administration to patients. If parenteral administration is the chosen route of administration, intramuscular injection is preferred. The compounds may be formulated for fast dispersing dosage forms (fddf), which are designed to release the active ingredient in the oral cavity. These have often been formulated using rapidly soluble gelatin-based matrices. These dosage forms are well known and can be used to deliver a wide range of drugs. Most fast dispersing dosage forms utilize gelatin as a carrier or structure-forming agent. Typically, gelatin is used to give sufficient strength to the dosage form to prevent breakage during removal from packaging, but once placed in the mouth, the gelatin allows immediate dissolution of the dosage form. Alternatively, various starches are used to the same effect.

The compound of the invention may also be formulated in rectal compositions such as suppositories or retention enemas, e.g. containing conventional suppository bases such as cocoa butter or other glycerides.

For intranasal administration or administration by inhalation, the compound of the invention is conveniently delivered in the form of a solution or suspension from a pump spray container that is squeezed or pumped by the patient or as an aerosol spray presentation from a pressurized container or a nebulizer, with the use of a suitable propellant, e.g. dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made e.g. from gelatin) for use in an inhaler or insulator may be formulated containing a powder mix of a compound of the invention and a suitable powder base such as lactose or starch. (Other formulations that need to added are: IM and Fast Dissolve FDDF A proposed dose of the active compounds of the invention for oral, parenteral or buccal administration to the average adult human for the treatment of the conditions referred to above (e.g. depression) is about 0.1 to about 200 mg of the active ingredient per unit dose which could be administered, for example, 1 to 4 times per day.

Aerosol formulations for treatment of the conditions referred to above (e.g. migraine) in the average adult human are preferably arranged so that each metered dose or "puff" of aerosol contains about 20 mg to about 1000 mg of the compound of the invention. The overall daily dose with an aerosol will be within the range of about 100 mg to about 10 mg. Administration may be several times daily, e.g. 2, 3, 4 or 8 times, giving for example, 1, 2 or 3 doses each time.

In connection with the use of the compound of the invention with a 5-HT re-uptake inhibitor, preferably sertraline, for the treatment of subjects possessing any of the above conditions, it is to be noted that these may be administered either alone or in combination with pharmaceutically acceptable carriers by either of the routes previously indicated, and that such administration can be carried out in both single and multiple dosages. More particularly, the active combination can be administered in a wide variety of different dosage forms, i.e. they may be combined with various pharmaceutically-acceptable inert carriers in the form of tablets, capsules, lozenges, troches, hard candies, powders, sprays, aqueous suspension, injectable solutions, elixirs, syrups, and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for such purposes. In general, the compounds of formula I are present in such dosage forms at concentration levels ranging from about 0.5% to about 90% by weight of the total composition, i.e., in amounts which are sufficient to provide the desired unit dosage and a 5-HT re-uptake inhibitor, preferably sertraline, is present in such dosage forms at concentration levels ranging from about 0.5% to about 90% by weight of the total composition, i.e. in amounts which are sufficient to provide the desired unit dosage.

A proposed daily dose of the compound of the invention in the combination formulation (a formulation containing the compound of the invention and a 5-HT re-uptake inhibitor) for oral, parenteral, rectal or buccal administration to the average adult human for the treatment of the conditions referred to above is from about 0.01 mg to about 2000 mg, preferably from about 0.1 mg to about 200 mg of the active ingredient of Formula I per unit dose which could be administered, for example, 1 to 4 times per day.

A proposed daily dose of a 5-HT re-uptake inhibitor, preferably sertraline, in the combination formulation for oral, parenteral or buccal administration to the average adult human for the treatment of the conditions referred to above is from about 0.1 mg to about 2000 mg, preferably from about 1 mg to about 200 mg of the 5-HT re-uptake inhibitor per unit dose which could be administered, for example, 1 to 4 times per day.

A preferred dose ratio of sertraline to an active compound of this invention in the combination formulation for oral, parenteral or buccal administration to the average adult human for the treatment of the conditions referred to above is from about 0.00005 to about 20000; preferably from about 0.25 to about 2000.

Aerosol combination formulations for treatment of the conditions referred to above in the average adult human are preferably arranged so that each metered dose or "puff" of aerosol contains from about 0.01 mg to about 100 mg of the active compound of this invention, preferably from about 1 mg to about 10 mg of such compound. Administration may be several times daily, e.g. 2, 3, 4 or 8 times, giving for example, 1, 2 or 3 doses each time.

Aerosol formulations for treatment of the conditions referred to above in the average adult human are preferably arranged so that each metered dose or "puff" of aerosol contains from about 0.01 mg to about 2000 mg of a 5-HT re-uptake inhibitor, preferably sertraline, preferably from about 1 mg to about 200 mg of sertraline. Administration may be several times daily, for example 2, 3, 4 or 8 times, giving for example, 1, 2 or 3 doses each time.

As previously indicated, a 5-HT re-uptake inhibitor, preferably sertraline, in combination with compounds of Formula I are readily adapted to therapeutic use as antidepressant agents. In general, these antidepressant compositions containing a 5-HT re-uptake inhibitor, preferably sertraline, and a compound of Formula I are normally administered in dosages ranging from about 0.01 mg to about 100 mg per kg of body weight per day of a 5-HT re-uptake inhibitor, preferably sertraline, preferably from about 0.1 mg to about 10 mg per kg of body weight per day of sertraline; with from about 0.001 mg. to about 100 mg per kg of body weight per day of a compound of Formula I, preferably from about 0.01 mg to about 10 mg per kg of body weight per day of a compound of Formula I, although variations will necessarily occur depending upon the conditions of the subject being treated and the particular route of administration chosen.

The following Examples illustrate the preparation of various compounds of the present invention. Melting points are uncorrected. NMR data are reported in parts per million and are referenced to the deuterium lock signal from the sample solvent (deuteriochloroform unless otherwise specified). Specific rotations were measured at room temperature using the sodium D line (589 nm). Commercial reagents were utilized without further purification. THF refers to tetrahydrofuran. DMF refers to N,N-dimethylformamide. Chromatography refers to column chromatography performed using 47–61 mesh silica gel and executed under nitrogen pressure (flash chromatography) conditions. Room or ambient temperature refers to 20–25° C. All non-aqueous reactions were run under a nitrogen atmosphere for convenience and to maximize yields. Concentration at reduced pressure means that a rotary evaporator was used. The Examples are illustrative only; they are not to be construed as limiting the scope, spirit and variations of the invention.

EXAMPLE 1

(7R,9aS)-trans-Cyclohexyl-{6-[2-(5-fluoro-benzo[d]isoxazol-3-yl)-octahydro-pyrido[1,2-a]pyrazin-7-ylmethoxy]-pyridin-2-ylmethyl}-amine Step 1

(7R,9aS)-trans-[2-(5-fluoro-benzo[d]isoxazol-3-yl)-octahydro-pyrido-1,2-a]pyrazin-7-yl]-methanol (Octahydro-quinazolin-3-yl)-methanol (5.42 g, 26.2 mmol), 1,8-diazobicyclo[5.4.0]-undec-7-ene (12.9 ml, 85 mmol), and 3-chloro-5-fluoro-benzo[d]isoxazole (5.54 g, 32.3 mmol) were dissolved in pyridine (16 ml), and then heated (110° C.) with stirring for 18 hours. 10% aqueous sodium bicarbonate and methylene chloride (250 ml of each) were added, and the mixture was vigorously stirred. The aqueous phase was then re-extracted with three 100 ml portions of fresh methylene chloride. The combined organic extracts were dried (anhydrous sodium sulfate) and concentrated in vacuo to an amorphous solid (4.88 g). Flash chromatography of the entire sample (silica gel, 47–61 micron mesh; elution with methanol/methylene chloride=6.94 in volume) afforded the title compound (3.46 g, 43% yield) as an amorphous solid. MS m/z 306 (M+1).

Step 2

(7R,9aS)-trans-6-[2-(5-Fluoro-benzo[d]isoxazol-3-yl)-octahydro-pyrido[1,2-a]pyrazin-7-ylmethoxy]-pyridine-2-carboxylic acid methyl ester To a solution of the title compound of the previous step (3.05 g, 10.0 mmol), 6-methyl-2-hydroxypicolinate (1.91 g, 12.5 mmol), diethylazodicarboxylate (1.1 ml, 12.0 mmol), and triphenylphosphine (3.14 g, 12.0) were combined in tetrahydrofuran (35 ml). The solution was heated (50° C.) and stirred for 18 hours. 10% aqueous sodium bicarbonate and methylene chloride (100 ml of each) were added, and the mixture was vigorously stirred. The aqueous phase was then re-extracted with three 50 ml portions of fresh methylene chloride. The combined organic extracts were, in turn, sequentially extracted with 1N aqueous sodium hydroxide and 10% aqueous sodium bicarbonate. The separated organic phase was dried (anhydrous sodium sulfate) and the solvent was removed in vacuo, yielding a tacky solid. Flash chromatography of the sample afforded the title compound (2.14 g, 48% yield) as white solid. Diagnostic $^1$H NMR (400 MHz, CDCl$_3$) 1.18–1.78 (m, 3H), 1.90–2.15 (m, 4H), 2.41–2.58 (m, 1H), 2.81–2.95 (m, 2H), 3.01–3.08 (m, 1H), 3.20–3.40 (m, 1H), 3.74–3.88 (m, 2H), 3.93 (s, 3H), 4.17 (dd, 1H, J=10.8 and 7.1 Hz), 4.28 (dd, 1H, J=10.8 and 5.4 hz), 6.87–6.92 (m, 1H), 7.18–7.21 (m, 1H), 7.29 (dd, 1H, J=9.3 and 2.5 hz), 7.36 (dd, 1H, J=9.1 and 3.8 Hz), 7.63–7.69 (m, 2H); MS m/z 441.3 (M+H).

Step 3

(7R,9aS)-trans-{6-[2-(5-Fluoro-benzo[d]isoxazol-3-yl)-octahydro-pyrido[1,2-a]pyrazin-7-ylmethoxy]-pyridin-2-yl}-methanol To a well stirred, ice bath-chilled partial solution of the title compound of the previous step (440 mg, 1.0 mmol) in tetrahydrofuran (10 ml), a 1.0M tetrahydrofuran solution of lithium aluminum hydride (1.2 ml, 1.20 mmol mmol) was added dropwise. The reaction mixture was then vigorously stirred at 0° C. for 1 hour before quenching by cautious dropwise addition of a total of 1 ml 1N aqueous sodium hydroxide. After stirring at ambient temperature for 30 minutes, the mixture was dried with anhydrous sodium sulfate and then filtered through celite. Solvent removal in vacuo afforded an oil. Flash chromatography of the sample afforded the title compound as white solid (162 mg; 39% yield). Diagnostic C$^{13}$ NMR (100 MHz, CDCl$_3$) 3.78 (d, 1H, J=12.9 Hz), 3.87 (d, 1H, J=12.6 Hz), 4.08–4.23 (m, 2H), 4.63 (s, 2H), 6.59 (d, 1H, J=8.2 Hz), 6.76 (d, 1H, J=7.5 Hz), 7.19–7.39 (m, 3H), 7.53 (t, 1H, J=7.4 Hz); MS m/z 413.3 (M+H).

Step 4

(7R,9aS)-trans-Methanesulfonic acid 6-[2-(5-fluoro-benzo[d]isoxazol-3-yl)-octahydro-pyrido[1,2-a]pyrazin-7-ylmethoxy]-pyridin-2-ylmethyl ester To a well-stirred mixture of the title compound (162 mg, 0.39 mmol) of the previous step (partially dissolved) and triethylamine (0.11 mL, 0.79 mmol) in methylene chloride (10 ml), at ambient temperature, methanesulfonyl chloride (34 μl, 0.43 mmol) was added. The reaction was stirred for 12 h before quenching with 10% aqueous sodium bicarbonate. The reaction mixture was extracted with three 10 ml fresh portions of methylene chloride. The combined organic extracts were dried (anhydrous sodium sulfate) and concentrated in vacuo. The oil was purified by flash chromatography to afford the title compound as a white solid (58 mg, 30%). The product was used in the next step without further purification. Diagnostic $^1$H NMR (400 MHz, CDCl$_3$) 5.16 (s, 3H); MS m/z 491.4 (M+H).

Step 5

The general procedure: A reaction mixture consisting of the mesylate title compound from the previous step (0.035 mmol, 17.2 mg) and an appropriate amine (0.15 mmol) in acetonitrile (1 ml) was stirred in a 2-dram vial at 90° C. for 12 hours. After cooling, 0.75 mL of sodium hydroxide and 2.2 mL of ethyl acetate was added to each vial. After agitation, the organic layer was separated and passed through Na2SO4 (6 mL SPE column, 2 g). The extraction procedure was repeated 2 more times with methylene chloride. The solvent is removed and the residue dissolved in 1.0 mL of DMSO and filitered through 0.45 MM Nylon Acrodisc into 12×32 mm HPLC vials for purification the amine (0.15 mmol) in 2-dram vials is added the mesylate and 0.9 mL of dry acetonitrile. The reaction is shaked and heated at 80° C. for 12 h in a sealed vial.

(7R,9aS)-trans-Cyclohexyl-{6-[2-(5-fluoro-benzo[d]
isoxazol-3-yl)-octahydro-pyrido[1,2-a]pyrazin-7-
ylmethoxy]-pyridin-2-ylmethyl}-amine.

The title mesylate prepared above, (7R,9aS)-trans-Methanesulfonic acid 6-[2-(5-fluoro-benzo[d]isoxazol-3-yl)-octahydro-pyrido[1,2-a]pyrazin-7-ylmethoxy]-pyridin-2-ylmethyl ester and cyclohexylamine were combined following Step 5 above. Purification using an HPLC prepartory column provided the title compound: Waters Symmetry (C18, 5 uM, 30×150 mm, Flow 20 mL/min, 0.1% TFA/CH$_3$CN), RT=6.66 min. MS m/z 493.6.

In Examples 2–18 the title compounds were prepared using the general procedure of Example 1, Step 5, with purification using an HPLC prepartory column and all with Waters Symmetry (C18, 5 uM, 30×150 mm, Flow 20 mL/min, 0.1% TFA/CH$_3$CN). The starting material is indicated for each example:

EXAMPLE 2

(7R,9aS)-trans-2-(Ethyl-{6-[2-(5-fluoro-benzo[d]
isoxazol-3-yl)-octahydro-pyrido[1,2-a]pyrazin-7-
ylmethoxy]-pyridin-2-ylmethyl}-amino)-ethanol.

Starting material: 2-ethyl-aminoalcohol. RT=7.60 min. MS m/z 483.6

EXAMPLE 3

(7R,9aS)-trans-7-[6-(2,6-Dimethyl-piperidin-1-ylm-
ethyl)-pyridin-2-yloxymethyl]-2-(5-fluoro-benzo[d]
isoxazol-3-yl)-octahydro-pyrido[1,2-a]pyrazine.

Starting material: 2,6 dimethylpiperidine. RT=7.76 min. MS m/z 507.7

EXAMPLE 4

(7R,9aS)-trans-1-(1-{6-[2-(5-Fluoro-benzo[d]isox-
azol-3-yl)-octahydro-pyrido[1,2-a]pyrazin-7-yl-
methoxy]-pyridin-2-ylmethyl}-4-phenyl-piperidin-4-
yl)ethanone.

Starting material: 4-acetyl-4-phenylpiperdine. RT=7.78 min. MS m/z 597.1.

EXAMPLE 5

(7R,9aS)-trans-(1,2-Dimethyl-propyl)-{6-[2-(5-
fluoro-benzo[d]isoxazol-3-yl)-octahydro-pyridol
[1,2-a]pyrazin-7-ylmethoxyl-pyridin-2-ylmethyl}-
amine.

Starting material: 1,2-dimethyl-propylamine. RT=7.89 min. MS m/z 481.6.

EXAMPLE 6

(7R,9aS)-trans-Cyclopropyl-{6-[2-(5-fluoro-benzo
[d]isoxazol-3-yl)-octahydro-pyrido[1,2-a]pyrazin-7-
ylmethoxy]-pyridin-2-ylmethyl}-amine.

Starting material: cyclopropylamine. RT=3.87 min. MS m/z 451.2.

EXAMPLE 7

(7R,9aS)-trans-Cyclopropylmethyl-{6-[2-(5-fluoro-
benzo[d]isoxazol-3-yl)-octahydro-pyrido[1,2-a]
pyrazin-7-ylmethoxy]-pyridin-2-ylmethyl}-amine.

Starting material: cyclopropylmethyl-amine. RT=3.91 min. MS m/z 465.3.

EXAMPLE 8

(7R,9aS)-trans-(4-Chloro-benzyl)-{6-[2-(5-fluoro-
benzo[d]isoxazol-3-yl)-octahydro-pyrido[1,2-a]
pyrazin-7-ylmethoxy]-pyridin-2-ylmethyl}-amine.

Starting material: 4-chloro-benzylamine. RT=4.11 min. MS m/z 535.2.

EXAMPLE 9

(7R,9aS)-trans-{6-[2-(5-Fluoro-benzo[d]isoxazol-3-
yl)-octahydro-pyrido[1,2-a]pyrazin-7-ylmethoxy]-
pyridin-2-ylmethyl}-[2-(1-methyl-pyrrolidin-2-yl)-
ethyl]-amine.

Starting material: 2-(1-methyl-pyrrolidin-2-yl)ethylamine. RT=3.77 min. MS m/z 522.3.

EXAMPLE 10

(7R,9aS)-trans-2-(5-Fluoro-benzo[d]isoxazol-3-yl)-
7-[6-(4-methyl-piperazin-1-ylmethyl)-pyridin-2-
yloxymethyl]-octahydro-pyrido[1,2-a]pyrazine.

Starting material: N-methylpiperazine MS m/z 494.3.

EXAMPLE 11

(7R,9aS)-trans-2-(5-Fluoro-benzo[d]isoxazol-3-yl)-7-(6-piperidin-1-ylmethyl-pyridin-2-yloxymethyl)-octahydro-pyrido[1,2-a]pyrazine.

Starting material: piperdine. RT=3.88 min. MS m/z 479.3.

EXAMPLE 12

(7R,9aS)-trans-{6-[2-(5-Fluoro-benzo[d]isoxazol-3-yl)-octahydro-pyrido[1,2-a]pyrazin-7-ylmethoxy]-pyridin-2-ylmethyl}-dimethyl-amine.

Starting material: dimethylamine. RT=3.82 min. MS m/z 439.2.

EXAMPLE 13

(7R,9aS)-trans-{6-[2-(5-Fluoro-benzo[d]isoxazol-3-yl)-octahydro-pyrido[1,2-a]pyrazin-7-ylmethoxy]-pyridin-2-ylmethyl}-(tetrahydro-furan-2-ylmethyl)-amine.

Starting material: tetrahydro-furan-2-ylmethylamine. RT=3.89 min. MS m/z 495.3.

EXAMPLE 14

(7R,9aS)-trans-7-[6-(2,5-Dimethyl-pyrrolidin-1-ylmethyl)-pyridin-2-yloxymethyl]-2-(5-fluoro-benzo[d]isoxazol-3-yl)-octahydro-pyrido[1,2-a]pyrazine.

Starting material: 2,5-dimethyl-pyrrolidine RT=3.92 min. MS m/z 493.3.

EXAMPLE 15

(7R,9aS)-trans-{6-[2-(5-Fluoro-benzo[d]isoxazol-3-yl)-octahydro-pyrido[1,2-a]pyrazin-7-ylmethoxy]-pyridin-2-ylmethyl}-(2,2,2-trifluoro-ethyl)-amine.

Starting material: 2,2,2-trifluoro-ethylamine. RT=3.91 min. MS m/z 493.2.

EXAMPLE 16

(7R,9aS)-trans-{6-[2-(5-Fluoro-benzo[d]isoxazol-3-yl)-octahydro-pyrido[1,2-a]pyrazin-7-ylmethoxy]-pyridin-2-ylmethyl}-[3-(4-methyl-piperazin-1-yl)-propyl]-amine.

Starting material: 3-(4-methyl-piperazin-1-yl)-propylamine. RT=3.74 min. MS m/z 551.3.

EXAMPLE 17

(7R,9aS)-trans-{6-[2-(5-Fluoro-benzo[d]isoxazol-3-yl)-octahydro-pyrido[1,2-a]pyrazin-7-ylmethoxy]-pyridin-2-ylmethyl}-pyrrolidin-1-yl-amine.

Starting material: 1-amino-pyrrolidine. RT=3.84 min. MS m/z 480.3

EXAMPLE 18

(7R,9aS)-trans-7-(6-Azepan-1-ylmethyl-pyridin-2-yloxymethyl)-2-(5-fluoro-benzo[d]isoxazol-3-yl)-octahydro-pyrido[1,2-a]pyrazine.

Starting material: cycloheptylamine. RT=3.93 min. MS m/z 493.3.

EXAMPLE 19

Step 1

(7R,9aS)-trans-[2-benzo[d]isoxazol-3-yl)-octahydro-pyrido-1,2-a]pyrazin-7-yl]-methanol (Octahydro-quinazolin-3-yl)-methanol (5.42 g, 26.2 mmol), 1,8-diazobicyclo[5.4.0]-undec-7-ene (12.9 ml, 85 mmol), and 3-chloro-benzo[d]isoxazole (5.54 g, 32.3 mmol) were dissolved in pyridine (16 ml), and then heated (110° C.) with stirring for 18 hours. 10% aqueous sodium bicarbonate and methylene chloride (250 ml of each) were added, and the mixture was vigorously stirred. The aqueous phase was then re-extracted with three 100 ml portions of fresh methylene chloride. The combined organic extracts were dried (anhydrous sodium sulfate) and concentrated in vacuo to an amorphous solid (4.88 g). Flash chromatography of the entire sample (silica gel, 47–61 micron mesh; elution with methanol/methylene chloride=6.94 in volume) afforded the title compound (3.46 g, 43% yield) as an amorphous solid. MS m/z 306 (M+1).

Step 2

(7R,9aS)-trans-5-(2-Benzo[d]isoxazol-3-yl-octahydro-pyrido[1,2-a]pyrazin-7-ylmethoxy)-pyridine-2-carboxylic acid methyl ester To a well-stirred mixture of the title compound (1.49 g, 5.0 mmol) of the previous step (partially dissolved) and triethylamine (1.4 mL, 10.0 mmol) in methylene chloride (40 ml), at ambient temperature, methanesulfonyl chloride (0.86 mL, 5.5 mmol) was added. The reaction was stirred for 12 h before quenching with 10% aqueous sodium bicarbonate. The reaction mixture was extracted with three 10 ml fresh portions of methylene chloride. The combined organic extracts were dried (anhydrous sodium sulfate) and concentrated in vacuo. The oil was purified by flash chromatography to afford the corresponding mesylate. The product was used in the next step without further purification.

To 5-methyl-2-hydroxynicotinate (0.92 g, 17 mmol) in tetrahydrofuran (50 ml) is added 0.18 g (6.0 mmol) of sodium hydride (60% in mineral oil). The reaction is heated to 100° C. for 1 h. The mesylate prepared above is dissolved in 10 mL of tetrahydrofuran and added to the reaction mixture. The solution was heated (100° C.) and stirred for 18 hours. The reaction was concentrated and filtered with ethyl ether. The separated organic phase was dried (anhydrous sodium sulfate) and the solvent was removed in vacuo. Flash chromatography of the sample afforded the title compound (440 mg, 21% yield) as a off-white solid. Diagnostic $^1$H NMR (400 MHz, CDCl$_3$) 1.17–1.25 (m, 1H), 1.29–1.39 (m, 1H), 1.75–1.80 (m, 1H), 1.85–1.98 (m, 2H), 2.09–2.15 (m, 2H), 2.51–2.59 (m, 1H), 2.80–2.90 (m, 2H), 3.08 (d, 1H, J=8.8 Hz), 3.20–3.35 (m, 1H), 3.84 (s, 3H), 3.78 (d, 1H, J=13.3 Hz), 4.12 (dd, 1H, J=10.4 and 7.4 Hz), 4.27 (dd, 1H, J=10.4 and 5.4 Hz), 6.72 (dd, 1H, J=9.7 and 0.8 Hz), 7.17–7.21 (m, 1H), 7.41–7.48 (m, 2H), 7.66 (d, 1H, J=7.9 Hz), 8.11 (dd, 1H, J=8.7 and 2.4 Hz), and 8.76–8.78 (m, 1H).

Step 3

(7R,9aS)-trans-[5-(2-Benzo[d]isoxazol-3-yl-octahydro-pyrido[1,2-a]pyrazin-7-ylmethoxy)-pyridin-2-yl]-methanol To a well stirred, ice bath-chilled partial solution of the title compound of the previous step (991 mg, 2.35 mmol) in tetrahydrofuran (30 ml), a 1.0M tetrahydrofuran solution of lithium aluminum hydride (4.7 ml, 4.70 mmol) was added dropwise at 0° C. The reaction mixture was then vigorously stirred for 1 hour before quenching by cautious dropwise addition (at 0° C.) of a total of 1 ml 1N aqueous sodium hydroxide. After stirring at ambient temperature for 30 minutes, the mixture was dried with anhydrous sodium sulfate and then filtered through celite. Solvent removal in vacuo followed by flash chromatography of the sample afforded the title compound as a white solid (447 mg; 48% yield). Diagnostic $^1$H NMR (400 MHz, CDCl$_3$) 3.87 (d, 1H, J=12.9 Hz), 3.96 (d, 1H, J=12.4 Hz), 4.06 (dd, 1H, J=10.8 and 5.4 Hz), 4.59 (d, 2H, J=5.4 Hz), 6.70 (d, 1H, J=8.8 Hz), 7.17–7.21 (m, 1H), 7.42–7.49 (m, 2H), 7.59 (dd, 1H, J=8.7 and 2.5 Hz), 7.65 (d, 1H, J=7.9 Hz), 8.06 (d, 1H, J=2.5 Hz); MS m/z 395.2 (M+H).

Step 4

(7R,9aS)-trans-Methanesulfonic acid 5-(2-benzo[d]isoxazol-3-yl-octahydro-pyrido[1,2-a]pyrazin-7-ylmethoxy)-pyridin-2-ylmethyl ester To a well-stirred mixture of the title compound (148 mg, 0.38 mmol) of the previous step (partially dissolved) and triethylamine (0.1 mL, 0.75 mmol) in methylene chloride (5 ml), at ambient temperature, methanesulfonyl chloride (40 μl, 0.05 mmol) was added. The reaction was then stirred for 1 h before quenching with 10% aqueous sodium bicarbonate (with 20 ml of methylene chloride added). The reaction mixture was extracted with three 10 ml fresh portions of methylene chloride. The combined organic extracts were dried (anhydrous sodium sulfate) and concentrated in vacuo to afford the title compound as a viscous oil. The product was used in the next step without further purification.

Step 5

The general procedure is as follows: A reaction mixture consisting of (7R,9aS)-trans-Methanesulfonic acid 5-(2-benzo[d]isoxazol-3-yl-octahydro-pyrido[1,2-a]pyrazin-7-ylmethoxy)-pyridin-2-ylmethyl ester from the previous step (0.03 mmol, 14.2 mg) and an appropriate amine (0.12 mmol) in acetonitrile (1 ml) was stirred in a 2-dram vial at 90° C. for 12 hours. After cooling, the solvent is removed and the residue dissolved in 1.8 mL of DMSO and filitered through 0.45 MM Nylon Acrodisc into 12×32 mm HPLC vials for purification.

In Examples 20–39 the title compounds were prepared using the general procedure of Example 19, Step 5, with purification using an HPLC prepartory column and all with Waters Symmetry (C18, 5 uM, 30×150 mm, Flow 20 mL/min, 0.1% TFA/CH$_3$CN). The starting material is indicated for each example:

EXAMPLE 20

(7R,9aS)-trans-[6-(2-Benzo[d]isoxazol-3-yl-octahydro-pyrido[1,2-a]pyrazin-7-ylmethoxy)-pyridin-3-ylmethyl]-(3-methyl-isoxazol-4-yl)-amine.

Starting material: 3-methyl-4-amino-isoxazole RT=3.92 min. MS m/z 474.2.

EXAMPLE 21

(7R,9aS)-trans-[6-(2-Benzo[d]isoxazol-3-yl-octahydro-pyrido[1,2-a]pyrazin-7-ylmethoxy)-pyridin-3-ylmethyl]-thiazol-2-yl-amine.

Starting material: 2-amino-thiazole. RT=4.15 min. MS m/z 476.2

EXAMPLE 22

(7R,9aS)-trans-[6-(2-Benzo[d]isoxazol-3-yl-octahydro-pyrido[1,2-a]pyrazin-7-ylmethoxy)-pyridin-3-ylmethyl]-(3-methyl-isoxazol-5-yl)-amine.

Starting material: 3-methyl-5-amino-isoxazole. RT=4.16 min. MS m/z 474.2

EXAMPLE 23

(7R,9aS)-trans-[6-(2-Benzo[d]isoxazol-3-yl-octahydro-pyrido[1,2-a]pyrazin-7-ylmethoxy)-pyridin-3-ylmethyl]-(3-methyl-pyridin-4-yl)-amine.

Starting material: 3-methyl-4-amino-pyridine. RT=3.90 min. MS m/z 484.3

EXAMPLE 24

(7R,9aS)-trans-[6-(2-Benzo[d]isoxazol-3-yl-octahydro-pyrido[1,2-a]pyrazin-7-ylmethoxy)-pyridin-3-ylmethyl]-(5-methyl-2H-pyrazol-3-yl)-amine.

Starting material: 5-methyl-3-amino-pyrazole. RT=3.85 min. MS m/z 473.3

EXAMPLE 25

(7R,9aS)-trans-[6-(2-Benzo[d]isoxazol-3-yl-octahydro-pyrido[1,2-a]pyrazin-7-ylmethoxy)-pyridin-3-ylmethyl]-(5-methyl-pyridin-2-yl)-amine.

Starting material: 5-methyl-2-amino-pyridine. RT=4.18 min. MS m/z 484.3

EXAMPLE 26

(7R,9aS)-trans-[6-(2-Benzo[d]isoxazol-3-yl-octahydro-pyrido[1,2-a]pyrazin-7-ylmethoxy)-pyridin-3-ylmethyl]-(1H-pyrazol-3-yl)-amine.

Starting material: 3-amino-pyrazole. RT=3.35 min. MS m/z 459.2.

EXAMPLE 27

(7R,9aS)-trans-[6-(2-Benzo[d]isoxazol-3-yl-octahydro-pyrido[1,2-a]pyrazin-7-ylmethoxy)-pyridin-3-ylmethyl]-(6-methyl-pyridin-2-yl)-amine.

Starting material: 6-methyl-2-amino-pyridine. RT=3.86 min. MS m/z 484.3

EXAMPLE 28

(7R,9aS)-trans-[6-(2-Benzo[d]isoxazol-3-yl-octahydro-pyrido[1,2-a]pyrazin-7-ylmethoxy)-pyridin-3-ylmethyl]-pyridin-2-yl-amine. Starting material: 2-amino-pyridine. RT=3.84 min. MS m/z 470.2

EXAMPLE 29

(7R,9aS)-trans-[6-(2-Benzo[d]isoxazol-3-yl-octahydro-pyrido[1,2-a]pyrazin-7-ylmethoxy)-pyridin-3-ylmethyl]-cyclopropylmethyl-amine.

Starting material: cyclopropyl-ethylamine. RT=3.86 min. MS m/z 447.3

EXAMPLE 30

(7R,9aS)-trans-[6-(2-Benzo[d]isoxazol-3-yl-octahydro-pyrido[1,2-a]pyrazin-7-ylmethoxy)-pyridin-3-ylmethyl]-(2-morpholin-4-yl-ethyl)-amine.

Starting material: 2-(4-morphoino)-ethylamine. RT=3.98 min. MS m/z 506.3.

EXAMPLE 31

(7R,9aS)-trans-[6-(2-Benzo[d]isoxazol-3-yl-octahydro-pyrido[1,2-a]pyrazin-7-ylmethoxy)-pyridin-3-ylmethyl]-pyrimidin-4-yl-amine.

Starting material: 4-aminopyrimidine. RT=3.66 min. MS m/z 471.2.

EXAMPLE 32

(7R,9aS)-trans-[6-(2-Benzo[d]isoxazol-3-yl-octahydro-pyrido[1,2-a]pyrazin-7-ylmethoxy)-pyridin-3-ylmethyl]-cyclopropyl-amine.

Starting material: cyclpropylamine. RT=3.88 min. MS m/z 433.2

EXAMPLE 33

(7R,9aS)-trans-[6-(2-Benzo[d]isoxazol-3-yl-octahydro-pyrido[1,2-a]pyrazin-7-ylmethoxy)-pyridin-3-ylmethyl]-(6-methoxy-pyridin-3-yl)-amine.

Starting material: 6-methoxy-2-amino-pyridine. RT=3.99 min. MS m/z 500.3

EXAMPLE 34

(7R,9aS)-trans-[6-(2-Benzo[d]isoxazol-3-yl-octahydro-pyrido[1,2-a]pyrazin-7-ylmethoxy)-pyridin-3-ylmethyl]-(2-pyrrolidin-1-yl-ethyl)-amine.

Starting material: 1-(2-pyrrolidino)-ethylamine RT=3.89 min. MS m/z 490.3.

EXAMPLE 35

(7R,9aS)-trans-2-Benzo[d]isoxazol-3-yl-7-[5-(4-methyl-[1.4]diazepan-1-ylmethyl)-pyridin-2-yloxymethyl]-octahydro-pyrido[1,2-a]pyrazine.

Starting material: 1-methylhomopiperazine. RT=3.88 min. MS m/z 490.3.

EXAMPLE 36

(7R,9aS)-trans-[6-(2-Benzo[d]isoxazol-3-yl-octahydro-pyrido[1,2-a]pyrazin-7-ylmethoxy)-pyridin-3-ylmethyl]-(tetrahydro-furan-2-ylmethyl)-amine.

Starting material: 2-(aminomethyl)-tetrahydrofuran. RT=3.89 min. MS m/z 477.2.

EXAMPLE 37

(7R,9aS)-trans-[6-(2-Benzo[d]isoxazol-3-yl-octahydro-pyrido[1,2-a]pyrazin-7-ylmethoxy)-pyridin-3-ylmethyl]-(1-phenyl-ethyl)-amine Starting material: 1-phenyl-ethyl-amine. MS m/z 498.1 (M+1).

EXAMPLE 38

(7R,9aS)-trans-[6-(2-Benzo[d]isoxazol-3-yl-octahydro-pyrido[1,2-a]pyrazin-7-ylmethoxy)-pyridin-3-ylmethyl]-pyridin-3-ylmethyl-amine Starting material: 3-pyridyl-methylamine. MS m/z 485.1 (M+1).

EXAMPLE 39

(7R,9aS)-trans-[6-(2-Benzo[d]isoxazol-3-yl-octahydro-pyrido[1,2-a]pyrazin-7-ylmethoxy)-pyridin-3-ylmethyl]-pyridin-3-yl-amine Starting material: 3-pyridyl-methylamine: HPLC prep column. MS m/z 471.1 (M+1).

EXAMPLE 40

(7R,9aS)-trans-[6-(2-Benzo[d]isoxazol-3-yl-octahydro-pyrido[1,2-a]pyrazin-7-ylmethoxy)-pyridin-2-ylmethyl]-thiazol-2-yl-amine.

Step 1

(7R,9aS)-trans-[2-benzo[d]isoxazol-3-yl)-octahydro-pyrido-1,2-a]pyrazin-7-yl]-methanol (Octahydro-quinazolin-3-yl)-methanol (5.42 g, 26.2 mmol), 1,8-diazobicyclo[5.4.0]-undec-7-ene (12.9 ml, 85 mmol), and 3-chloro-benzo[d]isoxazole (5.54 g, 32.3 mmol) were dissolved in pyridine (16 ml), and then heated (110° C.) with stirring for 18 hours. 10% aqueous sodium bicarbonate and methylene chloride (250 ml of each) were added, and the mixture was vigorously stirred. The aqueous phase was then re-extracted with three 100 ml portions of fresh methylene chloride. The combined organic extracts were dried (anhydrous sodium sulfate) and concentrated in vacuo to an amorphous solid (4.88 g). Flash chromatography of the entire sample (silica gel, 47–61 micron mesh; elution with methanol/methylene chloride=6.94 in volume) afforded the title compound (3.46 g, 43% yield) as an amorphous solid. MS m/z 306 (M+1).

Step 2

(7R,9aS)-trans-6-(2-Benzo[d]isoxazol-3-yl-octahydro-pyrido[1,2-a]pyrazin-7-ylmethoxy)-pyridine-2-carboxylic acid methyl ester To a solution of the title compound of the previous step (4.07 g, 14.18 mmol), 6-methyl-2-hydroxypiccolinate (3.25 g, 21.3 mmol), diethylazodicarboxylate (2.7 ml, 17.0 mmol), and triphenylphosphine (4.46 g, 17.0 mmol) were combined in tetrahydrofuran (50 ml). The solution was heated (50° C.) and stirred for 18 hours. 10% aqueous sodium bicarbonate and methylene chloride (100 ml of each) were added, and the mixture was vigorously stirred. The aqueous phase was then re-extracted with three 50 ml portions of fresh methylene chloride. The combined organic extracts were, in turn, sequentially extracted with 1N aqueous sodium hydroxide and 10% aqueous sodium bicarbonate. The separated organic phase was dried (anhydrous sodium sulfate) and the solvent was removed in vacuo. Flash chromatography of the sample afforded the title compound (3.39 g, 56% yield) as white solid. Diagnostic $^1$H NMR (400 MHz, CDCl$_3$) 1.21–1.29 (m, 1H), 1.40–1.79 (m, 2H), 1.95–1.99 (m, 1H), 2.01–2.09 (m, 1H), 2.20–2.40 (m, 2H), 2.50–2.60 (m, 1H), 2.80–3.02 (m, 2H), 3.20–3.45 (m, 1H), 3.87 (d, 1H, J=12.5 Hz), 3.92 (s, 3H), 3.97 (d, 1H, J=11.7 Hz), 4.16–4.29 (m, 1H), 4.20–4.31 (m, 1H), 6.89 (dd, 1H, J=7.1 and 2.5 Hz), 7.17–7.21 (m, 1H), 7.40–7.52 (m, 2H), 7.61–7.68 (m, 3H); C13 NMR 52.9, 60.9, 110.8, 115.5, 119.2, 121.9, 122.9, 130.1, 139.4, 145.5, 164.3.

Step 3

(7R,9aS)-trans-[6-(2-Benzo[d]isoxazol-3-yl-octahydro-pyrido[1,2-a]pyrazin-7-ylmethoxy)-pyridin-2-yl]-methanol To a well stirred, ice bath-chilled partial solution of the title compound of the previous step (2.76 g, 6.54 mmol) in tetrahydrofuran (30 ml), a 1.0M tetrahydrofuran solution of lithium aluminum hydride (7.0 ml, 7.0 mmol) was added dropwise. The reaction mixture was stirred at 0° C. for 1 hour before quenching by cautious dropwise addition (at 0° C.) of a total of 1 ml 1N aqueous sodium hydroxide. After stirring at ambient temperature for 30 minutes, the mixture was dried with anhydrous sodium sulfate and then filtered through celite. Solvent removal in vacuo afforded an oil. Flash chromatography of the sample afforded the title compound as a white solid (2.05 g; 50% yield). Diagnostic $^1$H NMR (400 MHz, CDCl$_3$) 1.15–1.25 (m, 1H), 1.40–1.60 (m, 1H), 1.80–2.05 (m, 3H), 2.20–2.40 (m, 2H), 2.51–2.60 (m, 1H), 2.93–3.05 (m, 2H), 3.13–3.15 (m, 1H), 3.39–3.42 (m, 2H), 3.87 (d, 1H, J=12.9 Hz), 3.98 (d, 1H, J=12.1 Hz), 4.06–4.11 (m, 1H), 4.20–4.24 (m, 1H), 4.62 (d, 2H, J=5.4 Hz), 6.59 (d, 1H, J=7.9 Hz), 6.76 (d, 1H, J=7.0 Hz), 7.17–7.23 (m, 1H), 7.42–7.55 (m, 3H), 7.65 (d, 1H, J=8.3 Hz); C13 NMR 26.6, 58.5, 60.6, 64.1, 109.5, 110.8, 113.1, 122.1, 122.7, 129.9, 139.6, 164.2.

Step 4

(7R,9aS)-trans-Methanesulfonic acid 6-(2-benzo[d]isoxazol-3-yl-octahydro-pyrido[1,2-a]pyrazin-7-ylmethoxy)-pyridin-2-ylmethyl ester To a well-stirred mixture of the title compound (2.05 g, 5.2 mmol) of the previous step (partially dissolved) and triethylamine (1.09 mL, 7.90 mmol) in methylene chloride (20 ml), at ambient temperature, methanesulfonyl chloride (0.45 mL, 5.7 mmol) was added. The reaction was stirred for 3 h at rt before quenching with 10% aqueous sodium bicarbonate (with 20 ml of methylene chloride added). The reaction mixture was extracted with three 10 ml fresh portions of methylene chloride. The combined organic extracts were dried (anhydrous sodium sulfate) and concentrated in vacuo to afford the title compound as a viscous oil (2.21 g, 90%). The product was used in the next step without further purification. Diagnostic $^1$H NMR (400 MHz, CDCl$_3$) 5.15 ppm.

Step 5

General Procedure

A reaction mixture consisting of the mesylate title compound from the previous step (0.03 mmol, 14.2 mg) and an appropriate amine (0.12 mmol) in acetonitrile (1 ml) was stirred in a 2-dram vial at 90° C. for 12 hours. After cooling, the solvent is removed and the residue dissolved in 1.8 mL of DMSO and filitered through 0.45 MM Nylon Acrodisc into 12×32 mm HPLC vials for purification.

In Examples 41–52 the title compounds were prepared using the general procedure of Example 40, Step 5, with Waters Symmetry (C18, 5 uM, 30×150 mm, Flow 20 mL/min, 0.1% TFA/CH$_3$CN). The starting material is indicated for each example:

EXAMPLE 41

(7R,9aS)-trans-[6-(2-Benzo[d]isoxazol-3-yl-octahydro-pyrido[1,2-a]pyrazin-7-ylmethoxy)-pyridin-2-ylmethyl]-thiazol-2-yl-amine.

Starting material: 2-amino-thiazole and the mesylate from Step 4. RT=8.50 min. MS m/z 476.2

EXAMPLE 42

(7R,9aS)-trans-[6-(2-Benzo[d]isoxazol-3-yl-octahydro-pyrido[1,2-a]pyrazin-7-ylmethoxy)-pyridin-2-ylmethyl]-(3-methyl-pyridin-4-yl)-amine.

Starting material: 4-amino-pyridine. RT=8.58 min. MS m/z 484.3

EXAMPLE 43

(7R,9aS)-trans-[6-(2-Benzo[d]isoxazol-3-yl-octahydro-pyrido[1,2-a]pyrazin-7-ylmethoxy)-pyridin-2-ylmethyl-(5-methyl-2H-pyrazol-3-yl)-amine.

Starting material: 5-methyl-2-amino-pyrazole. RT=8.56 min. MS m/z 473.3.

EXAMPLE 44

(7R,9aS)-trans-[6-(2-Benzo[d]isoxazol-3-yl-octahydro-pyrido[1,2-a]pyrazin-7-ylmethoxy)-pyridin-2-ylmethyl]-(5-methyl-pyridin-2-yl)-amine.

Starting material: 5-methyl-2-amino-pyridine. RT=8.66 min. MS m/z 484.3

EXAMPLE 45

(7R,9aS)-trans-[6-(2-Benzo[d]isoxazol-3-yl-octahydro-pyrido[1,2-a]pyrazin-7-ylmethoxy)-pyridin-2-ylmethyl]-(1H-pyrazol-3-yl)-amine.

Starting material: 3-amino-pyrazole. RT=8.60 min. MS m/z 459.2.

EXAMPLE 46

(7R,9aS)-trans-[6-(2-Benzo[d]isoxazol-3-yl-octahydro-pyrido[1,2-a]pyrazin-7-ylmethoxy)-pyridin-2-ylmethyl]-(6-methyl-pyridin-2-yl)-amine.

Starting material: 6-methyl-2-amino-pyridine. RT=8.75 min. S m/z 484.3.

EXAMPLE 47

(7R,9aS)-trans-[6-(2-Benzo[d]isoxazol-3-yl-octahydro-pyrido[1,2-a]pyrazin-7-ylmethoxy)-pyridin-2-ylmethyl]-pyridin-2-yl-amine.

Starting material: 2-amino-pyridine. RT=8.50 min. MS m/z 470.2.

EXAMPLE 48

(7R,9aS)-trans-[6-(2-Benzo[d]isoxazol-3-yl-octahydro-pyrido[1,2-a]pyrazin-7-ylmethoxy)-pyridin-2-ylmethyl]-cyclopropylmethyl-amine.

Starting material: aminomethyl-cyclcopropane. RT=8.65 min. MS m/z 447.3

EXAMPLE 49

(7R,9aS)-trans-[6-(2-Benzo[d]isoxazol-3-yl-octahydro-pyrido[1,2-a]pyrazin-7-ylmethoxy)-pyridin-2-ylmethyl]-(2-morpholin-4-yl-ethyl)-amine.

Starting material: 2-(4-morpholino)ethylamine. RT=8.17 min. MS m/z 506.3.

EXAMPLE 50

(7R,9aS)-trans-[6-(2-Benzo[d]isoxazol-3-yl-octahydro-pyrido[1,2-a]pyrazin-7-ylmethoxy)-pyridin-2-ylmethyl]-pyrimidin-4-yl-amine.

Starting material: 4-amino-pyrazine. RT=8.40 min. MS m/z 471.2.

EXAMPLE 51

(7R,9aS)-trans-[6-(2-Benzo[d]isoxazol-3-yl-octahydro-pyrido[1,2-a]pyrazin-7-ylmethoxy)-pyridin-2-ylmethyl]-(6-methoxy-pyridin-3-yl)-amine.

Starting material: 6-methoxy-3-amino-pyridine. RT=8.88 min. MS m/z 500.3.

EXAMPLE 52

(7R,9aS)-trans-[6-(2-Benzo[d]isoxazol-3-yl-octahydro-pyrido[1,2-a]pyrazin-7-ylmethoxy)-pyridin-2-ylmethyl]-(2-pyrrolidin-1-yl-ethyl)-amine.

Starting material: 2-pyrrolidino-ethylamine. RT=8.16 min. MS m/z 490.3

EXAMPLE 53

(7R,9aS)-trans-[6-(2-Benzo[d]isoxazol-3-yl-octahydro-pyrido[1,2-a]pyrazin-7-ylmethoxy)-pyridin-3-ylmethyl]-diethyl-amine Step 1

(Octahydro-quinazolin-3-yl)-methanol (5.42 g, 26.2 mmol), 1,8-diazobicyclo[5.4.0]-undec-7-ene (12.9 ml, 85 mmol), and 3-chloro-benzo[d]isoxazole (5.54 g, 32.3 mmol) were dissolved in pyridine (16 ml), and then heated (110° C.) with stirring for 18 hours. 10% aqueous sodium bicarbonate and methylene chloride (250 ml of each) were added, and the mixture was vigorously stirred. The aqueous phase was then re-extracted with three 100 ml portions of fresh methylene chloride. The combined organic extracts were dried (anhydrous sodium sulfate) and concentrated in vacuo to an amorphous solid (4.88 g). Flash chromatography of the entire sample (silica gel, 47–61 micron mesh; elution with methanol/methylene chloride=6.94 in volume) afforded (7R,9aS)-trans-[2-benzo[d]isoxazol-3-yl)-octahydro-pyrido-1,2-a]pyrazin-7-yl]-methanol: (3.46 g, 43% yield) as an amorphous solid. MS m/z 306 (M+1).

To a solution of 2-chloro-5-(chloromethyl)pyridine (0.28 g, 1.7 mmole) in 3 mL of dry acetonitrile is added 0.36 mL (3.46 mmol) of diethylamine followed by 240 mg (1.73 mmol) of potassium carbonate. The reaction is heated at 80° C. for 20 h. After cooling, the reaction mixture is quenched with 5 mL of water, extracted three-times with methylene chloride, and dried over sodium sulfate. Concentration of the solvent provided an oil which was purified by silica gel chromatography to provide 290 mg (85% yield) of 1-(6-Chloro-pyridin-3-ylmethyl)-diethylamine. Diagnostic $^1$H NMR (400 MHz, CDCl$_3$) 1.01–1.15 (m, 6H), 2.35–2.50 (m, 4H), 3.45–3.65 (m, 2H), 7.30 (d, 1H, J=8.3 Hz), 8.31 (d, 1H, J=2.1 Hz); MS 199.2 (M+H).

To (7R,9aS)-trans-[2-benzo[d]isoxazol-3-yl)-octahydro-pyrido-1,2-a]pyrazin-7-yl]-methanol (336 mg, 1.17 mmol) is added 6 mL of tetrahydrofuran followed by 1.46 mL of a 1.0 M solution of potassium tertbutoxide. The reaction is heated for 30 min. at 50° C. and 1-(6-Chloro-pyridin-3-ylmethyl)-diethylamine (290 mg, 1.46 mmol) is added. The solution is heated to reflux for 2 h and quenched with 5 mL of water, and extracted with methylene chloride. The organic layer is dried of sodium sulfate, concentrated, and the resultant solide purified by silica gel chromatography to provide the title compound 98 mg (22% yield). Diagnostic $C^{13}$ NMR (100 MHz, CDCl$_3$) 11.8, 27.2, 29.2, 36.3, 46.6, 48.5, 53.9, 54.2, 54.4, 59.0, 60.4, 68.9, 110.7, 110.9, 116.4, 122.4, 122.5, 127.7, 129.7, 140.0, 146.9, 161.3, 163.3, 164.2. MS m/z 405.4 (M+1).

EXAMPLE 54

(7R,9aS)-trans-1-[6-(2-Benzo[d]isoxazol-3-yl-octahydro-pyrido[1,2-a]pyrazin-7-ylmethoxy)-pyridin-3-ylmethyl]-pyrrolidin-3-ol To a solution of 2-chloro-5-(chloromethyl)pyridine (1.0 g, 6.2 mmole) in 10 mL of dry acetonitrile is added 1.03 mL (12.4 mmol) of (S)-3-hydroxy-pyrrolidine followed by 858 mg (6.2 mmol) of potassium carbonate. The reaction is heated at 80° C. for 2 h. After cooling, the reaction mixture is quenched with 20 mL of water, extracted three-times with methylene chloride, and dried over sodium sulfate. Concentration of the solvent provided an oil which was purified by silica gel chromatography to provide 900 mg (68% yield) of (S)-1-(6-Chloro-pyridin-3-ylmethyl)-pyrrolidin-3-ol. Diagnostic $C^{13}$ NMR (100 MHz, CDCl$_3$) 35.1, 52.5, 56.7, 63.0, 71.4, 124.2, 133.4, 139.6, 149.9, 150.4; MS 213.2 (M+H).

To (7R,9aS)-trans-[2-benzo[d]isoxazol-3-yl)-octahydro-pyrido-1,2-a]pyrazin-7-yl]-methanol (193 mg, 0.67 mmol) prepared as in Step 1, example 53 is added 2.5 mL of tetrahydrofuran followed by 0.66 mL of a 1.0 M solution of potassium tertbutoxide. The reaction is heated for 30 min. at 50° C. and (S)-1-(6-Chloro-pyridin-3-ylmethyl)-pyrrolidin-3-ol (140 mg, 0.66 mmol) is added. The solution is heated to reflux for 2 h and quenched with 5 mL of water, and extracted with methylene chloride. The organic layer is dried of sodium sulfate, concentrated, and the resultant solide purified by silica gel chromatography to provide the title compound 52 mg (17% yield). Diagnostic $C^{13}$ NMR (100 MHz, CDCl$_3$) 27.1, 29.1, 35.1, 48.4, 52.4, 53.9, 54.4, 56.9, 59.0, 60.3, 62.8, 68.9, 71.3, 110.7, 111.0, 116.3, 122.3, 122.5, 126.9, 129.7, 139.9, 146.8, 161.2, 163.4, 164.1. MS m/z 464.5 (M+1).

EXAMPLE 55

(7R,9aS)-trans-1-[6-(2-Benzo[d]isoxazol-3-yl-octahydro-pyrido[1,2-a]pyrazin-7-ylmethoxy)-pyridin-3-ylmethyl]-pyrrolidin-3-ol To a solution of 2-chloro-5-(chloromethyl)pyridine (1.0 g, 6.3 mmole) in 10 mL of dry acetonitrile is added 1.05 mL (12.6 mmol) of (R)-3-hydroxy-pyrrolidine followed by 858 mg (6.2 mmol) of potassium carbonate. The reaction is heated at 80° C. for 2 h. After cooling, the reaction mixture is quenched with 20 mL of water, extracted three-times with methylene chloride, and dried over sodium sulfate. Concentration of the solvent provided an oil which was purified by silica gel chromatography to provide 1.03 g (77% yield) of (R)-1-(6-Chloro-pyridin-3-ylmethyl)-pyrrolidin-3-ol. Diagnostic $C^{13}$ NMR (100 MHz, CDCl$_3$) 35.1, 52.5, 56.7, 63.0, 71.4, 124.2, 133.4, 139.6, 149.9, 150.4; MS 213.2 (M+H).

To (7R,9aS)-trans-[2-benzo[d]isoxazol-3-yl)-octahydro-pyrido-1,2-a]pyrazin-7-yl]-methanol (189 mg, 0.66 mmol) prepared as in Step 1, example 53 is added 2.5 mL of tetrahydrofuran followed by 0.65 mL of a 1.0 M solution of potassium tertbutoxide. The reaction is heated for 30 min. at 50° C. and (R)-1-(6-Chloro-pyridin-3-ylmethyl)-pyrrolidin-3-ol (138 mg, 0.65 mmol) is added. The solution is heated to reflux for 2 h and quenched with 5 mL of water, and extracted with methylene chloride. The organic layer is dried of sodium sulfate, concentrated, and the resultant solide purified by silica gel chromatography to provide the title compound 40 mg (13% yield). Diagnostic $C^{13}$ NMR (100 MHz, CDCl$_3$) 27.1, 29.1, 35.1, 48.4, 52.4, 53.9, 54.4, 56.9, 59.0, 60.3, 62.8, 68.9, 71.3, 110.7, 111.0, 116.3, 122.3, 122.5, 126.9, 129.7, 139.9, 146.8, 161.2, 163.4, 164.1. MS m/z 464.5 (M+1).

EXAMPLE 56

(7R,9aS)-trans-7-(5-Azetidin-1-ylmethyl-pyridin-2-yloxymethyl)-2-benzo[d]isoxazol-3-yl-octahydro-pyrido[1,2-a]pyrazine To a solution of 2-chloro-5-(chloromethyl)pyridine (0.34 g, 2.1 mmole) in 4 mL of dry acetonitrile is 389 mg (4.14 mmol) of azetidine-hydrochloride followed by 572 mg (4.14 mmol) of potassium carbonate. The reaction is heated at 80° C. for 3 h. After cooling, the reaction mixture is quenched with 5 mL of water, extracted three-times with methylene chloride, and dried over sodium sulfate. Concentration of the solvent provided an oil which was purified by silica gel chromatography to provide 200 mg (53% yield) of 1-(6-Chloro-pyridin-3-ylmethyl)-azetidine. Diagnostic $^1$H NMR (400 MHz, CDCl$_3$) 2.06–2.14 (m, 2H), 3.23 (t, 4H, J=7.0 Hz), 3.55 (s, 2H), 7.27 (d, 1H, J=7.9 Hz), 7.61 (dd, 1H, J=8.3 and 2.5 Hz), 8.26 (d, 1H, J=2.5 Hz); MS 183.2 (M+H).

To (7R,9aS)-trans-[2-benzo[d]isoxazol-3-yl)-octahydro-pyrido-1,2-a]pyrazin-7-yl]-methanol (255 mg, 0.88 mmol) prepared as in Step 1, example 53 is added 2.5 mL of tetrahydrofuran followed by 1.10 mL of a 1.0 M solution of potassium tertbutoxide. The reaction is heated for 30 min. at 50° C. and 1-(6-Chloro-pyridin-3-ylmethyl)-azetidine (200 mg, 1.10 mmol) is added. The solution is heated to reflux for 5 h and quenched with 5 mL of water, and extracted with methylene chloride. The organic layer is dried of sodium sulfate, concentrated, and the resultant solide purified by silica gel chromatography to provide the title compound 157 mg (41% yield). Diagnostic $C^{13}$ NMR (100 MHz, CDCl$_3$) 17.7, 25.0, 25.2, 33.5, 48.4, 53.8, 54.4, 55.1, 56.7, 60.6, 60.7, 66.9, 110.6, 110.9, 116.4, 122.4, 122.5, 126.4, 129.6, 139.5, 146.7, 161.3, 163.7, 164.1. MS m/z 434.5 (M+1).

EXAMPLE 57

(7R,9aS)-trans-[6-(2-Benzo[d]isoxazol-3-yl-octahydro-pyrido[1,2-a]pyrazin-7-ylmethoxy)-pyridin-3-ylmethyl]-(2-methoxy-ethyl)-methyl-amine To a solution of 2-chloro-5-(chloromethyl)pyridine (384 mg, 2.37 mmole) in 4 mL of dry acetonitrile is 0.51 mL (4.74 mmol) of 1-methyl-2-methoxyethylamine followed by 328 mg (2.37 mmol) of potassium carbonate. The reaction is heated at 80° C. for 3 h. After cooling, the reaction mixture is quenched with 5 mL of water, extracted three-times with methylene chloride, and dried over sodium sulfate. Concentration of the solvent provided an oil which was purified by silica gel chromatography to provide 395 mg (78% yield) of (6-Chloro-pyridin-3-ylmethyl)-(2-methoxy-ethyl)-methyl-amine. Diagnostic $^1$H NMR (400 MHz, CDCl$_3$) 2.25 (s, 3H), 2.59 (t, 2H, J=5.6 Hz), 3.32 (s, 3H), 3.49 (t, 2H, J=5.6 hz), 7.26 (d, 1H, J=8.5 Hz), 7.68 (dd, 1H, J=8.3 and 2.5 Hz), 8.27 9d, 1H, J=1.6 Hz); MS 215.2 (M+H).

To (7R,9aS)-trans-[2-benzo[d]isoxazol-3-yl)-octahydro-pyrido-1,2-a]pyrazin-7-yl]-methanol (344 mg, 1.20 mmol) prepared as in Step 1, example 53 is added 8 mL of tetrahydrofuran followed by 1.5 mL of a 1.0 M solution of potassium tertbutoxide. The reaction is heated for 30 min. at 50° C. and (6-Chloro-pyridin-3-ylmethyl)-(2-methoxy-ethyl)-methyl-amine (325 mg, 1.50 mmol) is added. The solution is heated to reflux for 12 h and quenched with 5 mL of water, and extracted with methylene chloride. The organic layer is dried of sodium sulfate, concentrated, and the resultant solide purified by silica gel chromatography to provide the title compound 308 mg (55% yield). Diagnostic $C^{13}$ NMR (100 MHz, $CDCl_3$) 27.2, 29.2, 36.3, 39.2, 42.6, 48.5, 53.9, 54.4, 56.2, 58.9, 59.0, 59.1, 59.3, 60.4, 68.9, 70.9, 110.7, 110.9, 116.4, 122.4, 122.5, 126.8, 129.7, 140.2, 147.2, 161.3, 163.5, 164.2. MS m/z 466.5 (M+1).

EXAMPLE 58

(7R,9aS)-trans-[6-(2-Benzo[d]isoxazol-3-yl-octahydro-pyrido[1,2-a]pyrazin-7-ylmethoxy)-pyridin-3-ylmethyl]-cyclopentyl-methyl-amine To a solution of 2-chloro-5-(chloromethyl)pyridine (318 mg, 1.96 mmole) in 4 mL of dry acetonitrile is 395 mg (3.92 mmol) of N-methylcyclopentylamine followed by 270 mg (1.96 mmol) of potassium carbonate. The reaction is heated at 80° C. for 20 h. After cooling, the reaction mixture is quenched with 5 mL of water, extracted three-times with methylene chloride, and dried over sodium sulfate. Concentration of the solvent provided an oil which was purified by silica gel chromatography to provide 340 mg (77% yield) of (6-Chloro-pyridin-3-ylmethyl)-cyclopentyl-methyl-amine. Diagnostic $^1$H NMR (400 MHz, $CDCl_3$) 1.40–1.90 (m, 4H), 2.15 (s, 3H), 2.78–2.89 (m, 1H), 3.56 (s, 2H), 7.29 (d, 1H, J=8.3 Hz), 7.70–7.80 (m, 1H), 8.28 (d, 1H, J=2.1 Hz); MS 225.3 (M+H).

To 7R,9aS)-trans-[2-benzo[d]isoxazol-3-yl)-octahydro-pyrido-1,2-a]pyrazin-7-yl]-methanol (350 mg, 1.21 mmol) prepared as in Step 1, example 53 is added 8 mL of tetrahydrofuran followed by 1.52 mL of a 1.0 M solution of potassium tertbutoxide. The reaction is heated for 30 min. at 50° C. and (6-Chloro-pyridin-3-ylmethyl)-cyclopentyl-methyl-amine (340 mg, 1.52 mmol) is added. The solution is heated to reflux for 5 h and quenched with 5 mL of water, and extracted with methylene chloride. The organic layer is dried of sodium sulfate, concentrated, and the resultant solide purified by silica gel chromatography to provide the title compound 271 mg (47% yield). Diagnostic $C^{13}$ NMR (100 MHz, $CDCl_3$) 24.5, 27.2, 29.2, 30.6, 36.6, 39.9, 48.5, 53.9, 54.4, 57.3, 59.0, 60.4, 66.6, 66.9, 110.7, 110.9, 116.4, 122.4, 122.5, 127.3, 129.7, 140.2, 147.1, 161.2, 153.3, 164.1. MS m/z 476.5 (M+1).

EXAMPLE 59

(7R,9aS)-trans-N-[6-(2-Benzo[d]isoxazol-3-yl-octahydro-pyrido[1,2-a]pyrazin-7-ylmethoxy)-pyridin-3-ylmethyl-N,N'-dimethyl-ethane-1,2-diamine To a solution of 2-chloro-5-(chloromethyl)pyridine (586 mg, 3.62 mmole) in 8 mL of dry acetonitrile is 756 mg (7.24 mmol) of N—N'-dimethylethylenediamine followed by 500 mg (3.62 mmol) of potassium carbonate. The reaction is heated at 80° C. for 1 h. After cooling, the reaction mixture is quenched with 5 mL of water, extracted three-times with methylene chloride, and dried over sodium sulfate. Concentration of the solvent provided an oil which was purified by silica gel chromatography to provide 400 mg (52% yield) of N-(6-Chloro-pyridin-3-ylmethyl)-N,N'-dimethyl-ethane-1, 2-diamine. Diagnostic $^1$H NMR (400 MHz, $CDCl_3$) 2.18 (s, 3H), 2.31 (brs, 1H), 2.48 (s, 3H), 2.61 (t, 2H, J=6.1 Hz), 2.76 (t, 2H, J=6.1 Hz), 3.47 (s, 2H), 7.28 (d, 1H, J=7.9 and 2.5 Hz), 8.31 (d, 1H, J=1.6 Hz); MS 214.2 (M+H).

To 7R,9aS)-trans-[2-benzo[d]isoxazol-3-yl)-octahydro-pyrido-1,2-a]pyrazin-7-yl]-methanol (273 mg, 0.95 mmol) prepared as in Step 1, example 53 is added 6 mL of tetrahydrofuran followed by 1.19 mL of a 1.0 M solution of potassium tertbutoxide. The reaction is heated for 30 min. at 50° C. and N-(6-Chloro-pyridin-3-ylmethyl)-N,N'-dimethyl-ethane-1,2-diamine (253 mg, 1.19 mmol) is added. The solution is heated to reflux for 12 h and quenched with 5 mL of water, and extracted with methylene chloride. The organic layer is dried of sodium sulfate, concentrated, and the resultant solide purified by silica gel chromatography to provide the title compound 25 mg (5% yield). Diagnostic $C^{13}$ NMR (100 MHz, $CDCl_3$) 2.8, 27.1, 29.2, 31.8, 35.3, 36.3, 41.7, 48.2, 48.5, 53.9, 54.4, 54.9, 59.0, 59.4, 60.4, 68.9, 110.7, 111.1, 116.4, 122.3, 122.4, 126.8, 129.7, 140.1, 147.0, 161.3, 163.5, 164.1. MS m/z 465.5 (M+1).

EXAMPLE 60

(7R,9aS)-trans-2-Benzo[d]isoxazol-3-yl-7-[5-(2-methyl-aziridin-1-ylmethyl)-pyridin-2-yloxymethyl]-octahydro-pyrido[1,2-a]pyrazine To a solution of 2-chloro-5-(chloromethyl)pyridine (352 mg, 2.17 mmole) in 4 mL of dry acetonitrile is 0.4 mL (4.34 mmol) of 2-methyl-aziridine followed by 300 mg (2.17 mmol) of potassium carbonate. The reaction is heated at 60° C. for 20 h. After cooling, the reaction mixture is quenched with 5 mL of water, extracted three-times with methylene chloride, and dried over sodium sulfate. Concentration of the solvent provided an oil which was purified by silica gel chromatography to provide 66 mg (17% yield) of 2-Chloro-5-(2-methyl-aziridin-1-ylmethyl)-pyridine. Diagnostic $^1$H NMR (400 MHz, $CDCl_3$) 1.15 (d, 3H, J=5.4 Hz), 1.34 (d, 1H, J=6.6 Hz), 1.47–1.55 (m, 2H), 3.35 (abq, 2H, J=5.8 Hz), 7.25 (d, 1H, J=6.3 Hz), 7.65 (dd, 1H, J=8.3 and 2.5 Hz), 8.27 (d, 1H, J=1.7 Hz); MS 183.2 (M+H).

To (7R,9aS)-trans-[2-benzo[d]isoxazol-3-yl)-octahydro-pyrido-1,2-a]pyrazin-7-yl]-methanol (83 mg, 0.29 mmol) prepared as in Step 1, example 53 is added 2 mL of tetrahydrofuran followed by 0.36 mL of a 1.0 M solution of potassium tertbutoxide. The reaction is heated for 30 min. at 50° C. and 2-Chloro-5-(2-methyl-aziridin-1-ylmethyl)-pyridine (66 mg, 0.36 mmol) is added. The solution is heated to reflux for 12 h and quenched with 5 mL of water, and extracted with methylene chloride. The organic layer is dried of sodium sulfate, concentrated, and the resultant solide purified by silica gel chromatography to provide the title compound 20 mg (16% yield). Diagnostic $C^{13}$ NMR (100 MHz, $CDCl_3$) 18.5, 27.1, 29.1, 35.0, 35.2, 36.3, 48.4, 53.9, 54.4, 59.0, 60.4, 61.6, 68.8, 110.7, 111.0, 116.3, 122.3, 122.4, 127.9, 139.0, 146.0, 161.2, 163.3, 164.1. MS m/z 434.4 (M+1).

EXAMPLE 61

(7R,9aS)-trans-7-(5-Azepan-1-ylmethyl-pyridin-2-yloxymethyl)-2-benzo[d]isoxazol-3-yl-octahydro-pyrido[1,2-a]pyrazine To a solution of 2-chloro-5-(chloromethyl)pyridine (419 mg, 2.59 mmole) in 5 mL of dry acetonitrile is 512 mg (5.18 mmol) of azacycloheptane followed by 358 mg (2.59 mmol) of potassium carbonate. The reaction is heated at 80° C. for 20 h. After cooling, the reaction mixture is quenched with 5 mL of water, extracted three-times with methylene chloride, and dried over sodium sulfate. Concentration of the solvent provided an oil which was purified by silica gel chromatography to provide 340 mg (59% yield) of 1-(6-Chloro-pyridin-3-ylmethyl)-azepane. Diagnostic $^1$H NMR (400 MHz, CDCl$_3$) 1.40–1.70 (m, 8H), 2.50–2.65 (m, 4H), 3.65 (s, 2H), 7.28 (d, 1H, J=8.3 Hz), 7.65–7.70 (m, 1H), 8.30 (d, 1H, J=2.1 Hz); MS 225.3 (M+H).

To (7R,9aS)-trans-[2-benzo[d]isoxazol-3-yl)-octahydro-pyrido-1,2-a]pyrazin-7-yl]-methanol (284 mg, 0.99 mmol) prepared as in Step 1, example 53 is added 6 mL of tetrahydrofuran followed by 1.24 mL of a 1.0 M solution of potassium tertbutoxide. The reaction is heated for 30 min. at 50° C. and 1-(6-Chloro-pyridin-3-ylmethyl)-azepane (278 mg, 1.24 mmol) is added. The solution is heated to reflux for 12 h and quenched with 5 mL of water, and extracted with methylene chloride. The organic layer is dried of sodium sulfate, concentrated, and the resultant solide purified by silica gel chromatography to provide the title compound 37 mg (8% yield). Diagnostic C$^{13}$ NMR (100 MHz, CDCl$_3$) 27.1, 27.2, 28.1, 29.2, 36.3, 48.5, 53.9, 54.4, 55.5, 59.0, 59.4, 60.3, 68.9, 110.6, 110.9, 116.3, 122.4, 122.5, 127.8, 129.7, 139.9, 146.8, 161.3, 163.3, 164.2. MS m/z 476.5 (M+1).

EXAMPLE 62

(7R,9aS)-trans-2-Benzo[d]isoxazol-3-yl-7-[5-(2-methoxymethyl-pyrrolidin-1-ylmethyl)-pyridin-2-yloxymethyl]-octahydro-pyrido[1,2-a]pyrazine To a solution of 2-chloro-5-(chloromethyl)pyridine (369 mg, 2.28 mmole) in 5 mL of dry acetonitrile is 521 mg (4.52 mmol) of (S)-(+)-2-(methoxymethyl)pyrrolidinone followed by 314 mg (2.28 mmol) of potassium carbonate. The reaction is heated at 55° C. for 20 h. After cooling, the reaction mixture is quenched with 5 mL of water, extracted three-times with methylene chloride, and dried over sodium sulfate. Concentration of the solvent provided an oil which was purified by silica gel chromatography to provide 450 mg (82% yield) of 2-Chloro-5-(2-methoxymethyl-pyrrolidin-1-ylmethyl)-pyridine. Diagnostic $^1$H NMR (400 MHz, CDCl$_3$) 3.35 (s, 2h), 7.28 (d, 1H<J=7.9 Hz), 7.40–7.50 (m, 1H), 8.31 (d, 1H, J=2.1 Hz); MS 241.3 (M+H).

To (7R,9aS)-trans-[2-benzo[d]isoxazol-3-yl)-octahydro-pyrido-1,2-a]pyrazin-7-yl]-methanol (287 mg, 1.00 mmol) prepared as in Step 1, example 53 is added 6 mL of tetrahydrofuran followed by 1.25 mL of a 1.0 M solution of potassium tertbutoxide. The reaction is heated for 30 min. at 50° C. and 2-Chloro-5-(2-methoxymethyl-pyrrolidin-1-ylmethyl)-pyridine (300 mg, 1.25 mmol) is added. The solution is heated to reflux for 5 h and quenched with 5 mL of water, and extracted with methylene chloride. The organic layer is dried of sodium sulfate, concentrated, and the resultant solide purified by silica gel chromatography to provide the title compound 177 mg (36% yield). Diagnostic C$^{13}$ NMR (100 MHz, CDCl$_3$) 22.8, 27.1, 28.5, 29.2, 36.3, 48.5, 53.9, 54.4, 56.1, 59.0, 59.3, 60.3, 62.9, 68.8, 76.6, 110.6, 110.8, 116.3, 122.3, 122.4, 129.7, 140.2, 146.9, 161.2, 163.3, 164.2. MS m/z 492.5 (M+1).

EXAMPLE 63

(7R,9aS)-trans-[6-(2-Benzo[d]isoxazol-3-yl-octahydro-pyrido[1,2-a]pyrazin-7-ylmethoxy)-pyridin-3-ylmethyl]-tert-butyl-amine To a solution of 2-chloro-5-(chloromethyl)pyridine (537 mg, 3.31 mmole) in 7 mL of dry acetonitrile is 0.7 mL (6.62 mmol) of tert-butylamine followed by 457 mg (3.31 mmol) of potassium carbonate. The reaction is heated at 80° C. for 12 h. After cooling, the reaction mixture is quenched with 5 mL of water, extracted three-times with methylene chloride, and dried over sodium sulfate. Concentration of the solvent provided an oil which was purified by silica gel chromatography to provide 387 mg (59% yield) of tert-Butyl-(6-chloro-pyridin-3-ylmethyl)-amine. Diagnostic $^1$H NMR (400 MHz, CDCl$_3$) 1.16 (s, 9H), 1.60–1.80 (brs, 1H0, 3.72 (s, 2H), 7.26 (d, 1H, J=8.3 Hz), 7.71 (dd, 1H, J=8.3 and 2.5 Hz), 8.33 (d, 1H, J=2.0 Hz); MS 199.2 (M+H).

To (7R,9aS)-trans-[2-benzo[d]isoxazol-3-yl)-octahydro-pyrido-1,2-a]pyrazin-7-yl]-methanol (222 mg, 0.77 mmol) prepared as in Step 1, example 53 is added 4 mL of tetrahydrofuran followed by 0.96 mL of a 1.0 M solution of potassium tertbutoxide. The reaction is heated for 30 min. at 50° C. and of tert-Butyl-(6-chloro-pyridin-3-ylmethyl)-amine (190 mg, 0.96 mmol) is added. The solution is heated to reflux for 12 h and quenched with 5 mL of water, and extracted with methylene chloride. The organic layer is dried of sodium sulfate, concentrated, and the resultant solide purified by silica gel chromatography to provide the title compound 150 mg (43% yield). Diagnostic C$^{13}$ NMR (100 MHz, CDCl$_3$) 27.2, 29.2, 29.3, 36.3, 44.1, 48.5, 51.1, 53.9, 54.4, 59.0, 60.3, 68.8, 110.6, 110.9, 116.3, 122.3, 122.4, 129.7, 139.5, 146.3, 161.2, 163.3, 164.2. MS m/z 450.5 (M+1).

EXAMPLE 64

(7R,9aS)-trans-[6-(2-Benzo[d]isoxazol-3-yl-octahydro-pyrido[1,2-a]pyrazin-7-ylmethoxy)-pyridin-3-ylmethyl]-tert-butyl-methyl-amine To a solution of 2-chloro-5-(chloromethyl)pyridine (570 mg, 3.52 mmole) in 7 mL of dry acetonitrile is 608 mg (7.04 mmol) of N-methyl-t-butylamine followed by 486 mg (3.52 mmol) of potassium carbonate. The reaction is heated at 80° C. for 12 h. After cooling, the reaction mixture is quenched with 5 mL of water, extracted three-times with methylene chloride, and dried over sodium sulfate. Concentration of the solvent provided an oil which was purified by silica gel chromatography to provide 420 mg (56% yield) of N-methyl-tert-Butyl-(6-chloro-pyridin-3-ylmethyl)-amine. Diagnostic $^1$H NMR (400 MHz, CDCl$_3$) 1.14 (s, 9H), 2.06 (s, 3H), 3.48 (s, 2H), 7.26 (d, 1H, J=6.2 Hz), 7.68 (d, 1 h, J=6.6 Hz), 8.28 (d, 1H, J=2.5 Hz); MS 213.3 (M+H).

To (7R,9aS)-trans-[2-benzo[d]isoxazol-3-yl)-octahydro-pyrido-1,2-a]pyrazin-7-yl]-methanol (226 mg, 0.79 mmol) prepared as in Step 1, example 53 is added 4 mL of tetrahydrofuran followed by 0.98 mL of a 1.0 M solution of potassium tertbutoxide. The reaction is heated for 30 min. at 50° C. and of of N-methyl-tert-Butyl-(6-chloro-pyridin-3-ylmethyl)-amine (206 mg, 0.98 mmol) is added. The solution is heated to reflux for 12 h and quenched with 5 mL of water, and extracted with methylene chloride. The organic layer is dried of sodium sulfate, concentrated, and the resultant solide purified by silica gel chromatography to provide the title compound 111 mg (30% yield). Diagnostic $C^{13}$ NMR (100 MHz, CDCl$_3$) 26.4, 27.1, 29.2, 34.5, 36.3, 48.5, 52.0, 53.9, 54.4, 59.0, 60.4, 68.8, 110.7, 110.9, 116.3, 122.3, 122.4, 129.7, 139.8, 146.6, 161.2, 163.2, 164.1. MS m/z 464.5 (M+1).

EXAMPLE 65

(7R,9aS)-trans-2-Benzo[d]isoxazol-3-yl-7-(5-thiazolidin-3-ylmethyl-pyridin-2-yloxymethyl)-octahydropyrido[1,2-a]pyrazine To a solution of 2-chloro-5-(chloromethyl)pyridine (500 mg, 3.08 mmole) in 4 mL of dry acetonitrile is added 0.42 mL (6.17 mmol) of thiazolidine followed by 852 mg (6.17 mmol) of potassium carbonate. The reaction is heated at 80° C. for 20 h. After cooling, the reaction mixture is quenched with 5 mL of water, extracted three-times with methylene chloride, and dried over sodium sulfate. Concentration of the solvent provided an oil which was purified by silica gel chromatography to provide 275 mg (42% yield) of 2-Chloro-5-thiazolidin-3-ylmethyl-pyridine. Diagnostic $C^{13}$ NMR (100 MHz, CDCl$_3$) 29.8, 53.6, 57.7, 60.3, 112.4, 124.4, 133.3, 139.6, 150.1; MS 215.2 (M+H).

To (7R,9aS)-trans-[2-benzo[d]isoxazol-3-yl)-octahydropyrido-1,2-a]pyrazin-7-yl]-methanol (134 mg, 0.47 mmol) prepared as in Step 1, example 53 is added 2 mL of tetrahydrofuran followed by 0.58 mL of a 1.0 M solution of potassium tertbutoxide. The reaction is heated for 30 min. at 50° C. and of of 2-Chloro-5-thiazolidin-3-ylmethyl-pyridine (124 mg, 0.58 mmol) is added. The solution is heated to relux for 12 h and quenched with 5 mL of water, and extracted with methylene chloride. The organic layer is dried of sodium sulfate, concentrated, and the resultant solide purified by silica gel chromatography to provide the title compound 184 mg (84% yield). Diagnostic $C^{13}$ NMR (100 MHz, CDCl$_3$) 27.1, 29.1, 29.7, 36.2, 48.4, 53.6, 53.9, 54.4, 57.5, 58.9, 60.1, 60.3, 68.9, 110.6, 111.2, 116.3, 122.3, 122.4, 126.9, 129.7, 139.9, 147.0, 161.2, 163.6, 164.1. MS m/z 466.5 (M+1).

EXAMPLE 66

(7R,9aS)-trans-2-Benzo[d]isoxazol-3-yl-7-(5-imidazol-1-ylmethyl-pyridin-2-yloxymethyl)-octahydropyrido[1,2-a]pyrazine To a solution of 2-chloro-5-(chloromethyl)pyridine (500 mg, 3.08 mmole) in 4 mL of dry acetonitrile is added 420 mL (6.17 mmol) of imidazole followed by 852 mg (6.17 mmol) of potassium carbonate. The reaction is heated at 80° C. for 20 h. After cooling, the reaction mixture is quenched with 5 mL of water, extracted three-times with methylene chloride, and dried over sodium sulfate. Concentration of the solvent provided an oil which was purified by silica gel chromatography to provide 410 mg (69% yield) of 2-Chloro-5-imidazol-1-ylmethyl-pyridine. Diagnostic $C^{13}$ NMR (100 MHz, CDCl$_3$) 47.7, 119.2, 124.9, 130.6, 131.1, 137.5, 137.8, 148.6, 151.8; MS 194.2 (M+H).

To (7R,9aS)-trans-[2-benzo[d]isoxazol-3-yl)-octahydropyrido-1,2-a]pyrazin-7-yl]-methanol (237 mg, 0.83 mmol) prepared as in Step 1, example 53 is added 4 mL of tetrahydrofuran followed by 1.03 mL of a 1.0 M solution of potassium tertbutoxide. The reaction is heated for 30 min. at 50° C. and of of 2-Chloro-5-imidazol-1-ylmethyl-pyridine (200 mg, 1.03 mmol) is added. The solution is heated to relux for 12 h and quenched with 5 mL of water, and extracted with methylene chloride. The organic layer is dried of sodium sulfate, concentrated, and the resultant solide purified by silica gel chromatography to provide the title compound 229 mg (62% yield). Diagnostic $C^{13}$ NMR (100 MHz, CDCl$_3$) 27.1, 29.0, 36.2, 48.0, 48.4, 53.8, 54.3, 58.9, 60.3, 69.1, 110.7, 111.8, 116.3, 119.0, 122.3, 122.5, 124.6, 129.7, 130.3, 137.3, 138.3, 146.1, 161.2, 164.1, 164.1. MS m/z 445.5 (M+1).

EXAMPLE 67

(7R,9aS)-trans-[6-(2-Benzo[d]isoxazol-3-yl-octahydro-pyrido[1,2-a]pyrazin-7-ylmethoxy)-pyridin-3-ylmethyl]-cyclohexyl-methyl-amine To a solution of 2-chloro-5-(chloromethyl)pyridine (500 mg, 3.08 mmole) in 8 mL of dry acetonitrile is 384 mg (3.39 mmol) of N-methylcyclohexylamine followed by 468 mg (3.39 mmol) of potassium carbonate. The reaction is heated at 80° C. for 20 h. After cooling, the reaction mixture is quenched with 5 mL of water, extracted three-times with methylene chloride, and dried over sodium sulfate. Concentration of the solvent provided an oil which was purified by silica gel chromatography to provide 700 mg (95% yield) of (6-Chloro-pyridin-3-ylmethyl)-cyclohexyl-methyl-amine. $C^{13}$ NMR 26.1, 26.6, 28.9, 37.7, 54.5, 62.8, 124.1, 135.1, 139.5, 149.9; MS 239.3 (M+H).

To (7R,9aS)-trans-[2-benzo[d]isoxazol-3-yl)-octahydropyrido-1,2-a]pyrazin-7-yl]-methanol (263 mg, 0.92 mmol) prepared as in Step 1, example 53 is added 4 mL of tetrahydrofuran followed by 1.15 mL of a 1.0 M solution of potassium tertbutoxide. The reaction is heated for 30 min. at 50° C. and of (6-Chloro-pyridin-3-ylmethyl)-cyclohexyl-methyl-amine (274 mg, 1.15 mmol) is added. The solution is heated to relux for 12 h and quenched with 5 mL of water, and extracted with methylene chloride. The organic layer is dried of sodium sulfate, concentrated, and the resultant solide purified by silica gel chromatography to provide the title compound 203 mg (45% yield). Diagnostic $C^{13}$ NMR (100 MHz, CDCl$_3$) 26.1, 26.5, 27.1, 28.7, 29.2, 36.3, 37.5, 48.5, 53.9, 54.4, 54.6, 59.0, 60.4, 62.5, 68.8, 110.7, 111.0, 116.3, 122.3, 122.4, 129.7, 139.9, 146.7, 161.3, 163.3, 164.1. MS m/z 490.6 (M+1).

EXAMPLE 68

(7R,9aS)-trans-[6-(2-Benzo[d]isoxazol-3-yl-octahydro-pyrido[1,2-a]pyrazin-7-ylmethoxy)-pyridin-3-ylmethyl]-dimethyl-amine To a solution of 2-chloro-5-(chloromethyl)pyridine (509 mg, 3.14 mmole) in 7 mL of dry acetonitrile is added 3.14 mL (6.28 mmol) of a 2M solution of dimethylamine in THF followed by 434 mg (3.14 mmol) of potassium carbonate. The reaction is heated at 55° C. for 20 h. After cooling, the reaction mixture is quenched with 5 mL of water, extracted three-times with methylene chloride, and dried over sodium sulfate. Concentration of the solvent provided an oil which was purified by silica gel chromatography to provide 194 mg (36% yield) of 1-(6-Chloro-pyridin-3-ylmethyl)-dimethylamine. Diagnostic $C^{13}$ NMR (100 MHz, CDCl$_3$) 45.5, 60.7, 124.2, 133.6, 139.7, 150.2, 150.4; MS 173.2 (M+H).

To (7R,9aS)-trans-[2-benzo[d]isoxazol-3-yl)-octahydropyrido-1,2-a]pyrazin-7-yl]-methanol (430 mg, 1.50 mmol)

prepared as in Step 1, example 53 is added 10 mL of tetrahydrofuran followed by 1.87 mL of a 1.0 M solution of potassium tertbutoxide. The reaction is heated for 30 min. at 50° C. and of 1-(6-Chloro-pyridin-3-ylmethyl)-dimethylamine (320 mg, 1.87 mmol) is added. The solution is heated to reflux for 3 h and quenched with 5 mL of water, and extracted with methylene chloride. The organic layer is dried of sodium sulfate, concentrated, and the resultant solide purified by silica gel chromatography to provide the title compound 270 mg (43% yield). Diagnostic $C^{13}$ NMR (100 MHz, $CDCl_3$) 27.2, 29.2, 36.3, 45.2, 48.5, 53.9, 54.4, 59.0, 60.3, 60.9, 68.9, 110.7, 111.0, 116.4, 122.3, 122.5, 126.8, 128.7, 140.1, 147.2, 161.3, 163.5, 164.2. MS m/z 422.4 (M+1).

EXAMPLE 69

(7R,9aS)-trans-[6-(2-Benzo[d]isoxazol-3-yl-octahydro-pyrido[1,2-a]pyrazin-7-ylmethoxy)-pyridin-3-ylmethyl]-ethyl-methyl-amine To a solution of 2-chloro-5-(chloromethyl)pyridine (1.0 g, 6.17 mmole) in 11 mL of dry acetonitrile is added 1.06 mL (12.3 mmol) of methylethylamine followed by 850 mg (6.17 mmol) of potassium carbonate. The reaction is heated at 80° C. for 5 h. After cooling, the reaction mixture is quenched with 5 mL of water, extracted three-times with methylene chloride, and dried over sodium sulfate. Concentration of the solvent provided an oil which was purified by silica gel chromatography to provide 1.0 g (87% yield) of 1-(6-Chloro-pyridin-3-ylmethyl)-methylethylamine. Diagnostic $^1$H NMR (400 MHz, $CDCl_3$) 1.06 (t, 3H, J=7.1 Hz), 2.14 (s, 3H), 2.40 (q, 2H, J=7.1 Hz), 3.43 (s, 2H), 7.25 (d, 1H, J=8.2 Hz), 7.62 (dd, 1H, J=8.2 and 5.8 Hz); MS (187.2 (M+H).

To (7R,9aS)-trans-[2-benzo[d]isoxazol-3-yl)-octahydro-pyrido-1,2-a]pyrazin-7-yl]-methanol (460 mg, 1.60 mmol) prepared as in Step 1, example 53 is added 10 mL of tetrahydrofuran followed by 2.0 mL of a 1.0 M solution of potassium tertbutoxide. The reaction is heated for 30 min. at 50° C. and 1-(6-Chloro-pyridin-3-ylmethyl)-methylethylamine (370 mg, 2.00 mmol) is added. The solution is heated to reflux for 3 h and quenched with 5 mL of water, and extracted with methylene chloride. The organic layer is dried of sodium sulfate, concentrated, and the resultant solide purified by silica gel chromatography to provide the title compound 400 mg (57% yield). Diagnostic $C^{13}$ NMR (100 MHz, $CDCl_3$) 12.5, 27.2, 29.2, 36.3, 41.5, 48.5, 51.1, 53.9, 54.4, 58.6, 59.0, 60.4, 68.9, 110.7, 110.9, 116.4, 122.4, 122.5, 127.0, 129.7, 140.1, 147.1, 161.3, 163.4, 164.2. MS m/z 436.5 (M+1).

EXAMPLE 70

(7R,9aS)-trans-[6-(2-Benzo[d]isoxazol-3-yl-octahydro-pyrido[1,2-a]pyrazin-7-ylmethoxy)-pyridin-3-ylmethyl]-(2-methoxy-1-methyl-ethyl)-amine To a solution of 2-chloro-5-(chloromethyl)pyridine (1.0 g, 6.17 mmole) in 11 mL of dry acetonitrile is added 1.30 mL (12.3 mmol) of 2-amino-1-methoxypropane followed by 850 mg (6.17 mmol) of potassium carbonate. The reaction is heated at 80° C. for 5 h. After cooling, the reaction mixture is quenched with 5 mL of water, extracted three-times with methylene chloride, and dried over sodium sulfate. Concentration of the solvent provided an oil which was purified by silica gel chromatography to provide 640 mg (48% yield) of (6-Chloro-pyridin-3-ylmethyl)-(2-methoxy-1-methyl-ethyl)-amine. Diagnostic $C^{13}$ NMR (100 MHz, $CDCl_3$) 17.2, 48.0, 52.3, 59.1, 77.2, 124.1, 135.3, 138.9, 149.5, 150.1 MS (217.2 (M+H).

To (7R,9aS)-trans-[2-benzo[d]isoxazol-3-yl)-octahydro-pyrido-1,2-a]pyrazin-7-yl]-methanol (279 mg, 0.98 mmol) prepared as in Step 1, example 53 is added 7 mL of tetrahydrofuran followed by 1.22 mL of a 1.0 M solution of potassium tertbutoxide. The reaction is heated for 30 min. at 50° C. and (6-Chloro-pyridin-3-ylmethyl)-(2-methoxy-1-methyl-ethyl)-amine (263 mg, 1.22 mmol) is added. The solution is heated to reflux for 3 h and quenched with 5 mL of water, and extracted with methylene chloride. The organic layer is dried of sodium sulfate, concentrated, and the resultant solide purified by silica gel chromatography to provide the title compound 210 mg (46% yield). Diagnostic $C^{13}$ NMR (100 MHz, $CDCl_3$) 17.1, 27.2, 29.2, 36.3, 48.1, 48.5, 52.0, 53.9, 54.4, 59.0, 59.1, 60.4, 68.9, 110.7, 111.1, 116.4, 122.4, 122.5, 128.5, 129.7, 139.4, 146.5, 161.3, 163.4, 164.2. MS m/z 466.5 (M+1).

EXAMPLE 71

(7R,9aS)-trans-2-Benzo[d]isoxazol-3-yl-7-[5-(2-methyl-pyrrolidin-1-ylmethyl)-pyridin-2-yloxymethyl]-octahydro-pyrido[1,2-a]pyrazine To a solution of 2-chloro-5-(chloromethyl)pyridine (498 mg, 3.07 mmole) in 6 mL of dry acetonitrile is added 0.63 mL (6.14 mmol) of 2-methyl-pyrrolidinone followed by 424 mg (3.07 mmol) of potassium carbonate. The reaction is heated at 80° C. for 2 h. After cooling, the reaction mixture is quenched with 5 mL of water, extracted three-times with methylene chloride, and dried over sodium sulfate. Concentration of the solvent provided an oil which was purified by silica gel chromatography to provide 500 mg (78% yield) 2-Chloro-5-(2-methyl-pyrrolidin-1-ylmethyl)-pyridine. Diagnostic $^1$H NMR (400 MHz, $CDCl_3$) 1.15 (d, 3H, J=5.8 Hz), 1.41–1.78 (m, 3h), 1.91–2.13 (m, 2H), 2.41–2.45 9m, 1H), 2.86 (t, 1H, J=6.0 Hz), 3.16 (d, 1H, J=13.3 Hz), 3.96 (d, 1H, J=13.3 Hz), 7.27 (d, 1H, J=8.3 Hz), 7.67 (d, 1H, J=7.1 Hz), 8.29 (d, 1H, J=2.1 Hz); MS 211.3 (M+H).

To (7R,9aS)-trans-[2-benzo[d]isoxazol-3-yl)-octahydro-pyrido-1,2-a]pyrazin-7-yl]-methanol (177 mg, 0.62 mmol) prepared as in Step 1, example 53 is added 3 mL of tetrahydrofuran followed by 0.77 mL of a 1.0 M solution of potassium tertbutoxide. The reaction is heated for 30 min. at 50° C. and 2-Chloro-5-(2-methyl-pyrrolidin-1-ylmethyl)-pyridine (162 mg, 0.77 mmol) is added. The solution is heated to reflux for 3 h and quenched with 5 mL of water, and extracted with methylene chloride. The organic layer is dried of sodium sulfate, concentrated, and the resultant solide purified by silica gel chromatography to provide the title compound 235 mg (82% yield). Diagnostic $C^{13}$ NMR (100 MHz, $CDCl_3$) 19.3, 21.6, 27.1, 29.2, 32.9, 36.3, 48.5, 53.9, 53.9, 54.4, 54.9, 59.0, 59.6, 60.3, 68.8, 110.7, 110.8, 116.3, 122.3, 122.4, 127.6, 129.7, 140.1, 146.8, 161.3, 163.2, 164.1. MS mz 462.4 (M+1).

EXAMPLE 72

(7S,9aS)-cis-2-Benzo[d]isoxazol-3-yl-7-(5-piperidin-1-ylmethyl-pyridin-2-yloxymethyl)-octahydro-pyrido[1,2-a]pyrazine Step 1

(Octahydro-quinazolin-3-yl)-methanol (18.8 g, 90.7 mmol), 1,8-diazobicyclo[5.4.0]-undec-7-ene (43.4 ml, 290.2 mmol), and 3-chloro-benzo[d]isoxazole (13.9 g, 90.7 mmol) were dissolved in pyridine (60 ml), and then heated (95° C.) with stirring for 18 hours. Water (300 mL) and methylene chloride (250 ml of each) were added, and the mixture was vigorously stirred. The aqueous phase was then re-extracted with three 100 ml portions of fresh methylene chloride. The combined organic extracts were dried (anhydrous sodium sulfate) and concentrated in vacuo to an amorphous solid. Flash chromatography of the reaction mixture afford (7S,9aS)-cis-[2-benzo[d]isoxazol-3-yl)-octahydro-pyrido-1,2-a]pyrazin-7-yl]-methanol (7.08 g, 27% yield) as an white solid. Diagnostic $C^{13}$ NMR (100 MHz, $CDCl_3$) 26.5, 27.1, 34.5, 48.5, 53.9, 54.4, 58.4, 60.3, 67.8, 110.7, 116.3, 122.3, 122.5, 129.7, 161.2, 164.1; MS m/z 288.4 (M+1).

To a solution of 2-chloro-5-(chloromethyl)pyridine (578 mg, 3.57 mmole) in 7 mL of dry acetonitrile is added 0.71 mL (7.14 mmol) of piperdine followed by 493 mg (3.57 mmol) of potassium carbonate. The reaction is heated at 80° C. for 20 h. After cooling, the reaction mixture is quenched with 5 mL of water, extracted three-times with methylene chloride, and dried over sodium sulfate. Concentration of the solvent provided an oil which was purified by silica gel chromatography to provide 581 mg (77% yield) of 2-Chloro-5-piperidin-1-ylmethyl-pyridine. Diagnostic $^1H$ NMR (400 MHz, $CDCl_3$) 1.40–1.65 (m, 6H), 2.20–2.39 (s, 4H), 3.47 (s, 2H), 7.28 (d, 1H, J=7.9 Hz), 8.60–8.69 (m, 1H), 8.28 (d, 1H, J=2.1 Hz); MS 211.3 (M+H).

To (7S,9aS)-cis-[2-benzo[d]isoxazol-3-yl)-octahydro-pyrido-1,2-a]pyrazin-7-yl]-methanol (170 mg, 0.59 mmol) prepared above is added 2 mL of tetrahydrofuran followed by 0.74 mL of a 1.0 M solution of potassium tertbutoxide. The reaction is heated for 30 min. at 50° C. and 2-Chloro-5-piperidin-1-ylmethyl-pyridine (155 mg, 0.74 mmol) is added. The solution is heated to reflux for 3 h and quenched with 5 mL of water, and extracted with methylene chloride. The organic layer is dried of sodium sulfate, concentrated, and the resultant solide purified by silica gel chromatography to provide the title compound 176 mg (65% yield). Diagnostic $C^{13}$ NMR (100 MHz, $CDCl_3$) 24.5, 25.0, 25.3, 26.1, 33.5, 48.4, 53.9, 54.4, 56.7, 60.5, 60.6, 66.9, 110.6, 110.7, 116.4, 122.4, 122.5, 126.5, 129.7, 140.1, 147.3, 161.3, 163.6, 164.1. MS m/z 462.5 (M+1).

EXAMPLE 73

(7S,9aS)-cis-[6-(2-Benzo[d]isoxazol-3-yl-octahydropyrido[1,2-a]pyrazin-7-ylmethoxy)-pyridin-3-ylmethyl]-dimethyl-amine Following the general procedure described in Step 2 of Example 72 and using 2-chloro-5-(chloromethyl)pyridine. The reaction provided 194 mg (36% yield) of 1-(6-Chloro-pyridin-3-ylmethyl)-dimethylamine. Diagnostic $C^{13}$ NMR (100 MHz, $CDCl_3$) 45.5, 60.7, 124.2, 133.6, 139.7, 150.2, 150.4; MS 173.2 (M+H).

To (7S,9aS)-cis-[2-benzo[d]isoxazol-3-yl)-octahydro-pyrido-1,2-a]pyrazin-7-yl]-methanol (155 mg, 0.54 mmol) prepared as in Step 1, example 72 is added 2 mL of tetrahydrofuran followed by 0.68 mL of a 1.0 M solution of potassium tertbutoxide. The reaction is heated for 30 min. at 50° C. and of 1-(6-Chloro-pyridin-3-ylmethyl)-dimethylamine (115 mg, 0.68 mmol) is added. The solution is heated to reflux for 3 h and quenched with 5 mL of water, and extracted with methylene chloride. The organic layer is dried of sodium sulfate, concentrated, and the resultant solide purified by silica gel chromatography to provide the title compound 151 mg (66% yield). Diagnostic $C^{13}$ NMR (100 MHz, $CDCl_3$) 25.0, 25.3, 33.5, 45.2, 48.5, 53.9, 54.4, 56.7, 60.6, 60.9, 67.0, 110.6, 110.9, 116.4, 122.4, 126.6, 129.6, 140.0, 147.3, 161.3, 163.8, 164.1. MS m/z 422.5 (M+1).

EXAMPLE 74

(7S,9aS)-cis-[6-(2-Benzo[d]isoxazol-3-yl-octahydropyrido[1,2-a]pyrazin-7-ylmethoxy)-pyridin-3-ylmethyl]-ethyl-methyl-amine Following the general procedure described in Step 2 of Example 72 and using 2-chloro-5-piperidin-1-ylmethyl-pyridine. The reaction provided 1.0 g (87% yield) of 1-(6-Chloro-pyridin-3-ylmethyl)-methylethylamine. Diagnostic $^1H$ NMR (400 MHz, $CDCl_3$) 1.06 (t, 3H, J=7.1 Hz), 2.14 (s, 3H), 2.40 (q, 2H, J=7.1 Hz), 3.43 (s, 2H), 7.25 (d, 1H, J=8.2 Hz), 7.62 (dd, 1H, J=8.2 and 5.8 Hz); MS (187.2 (M+H).

To (7S,9aS)-cis-[2-benzo[d]isoxazol-3-yl)-octahydro-pyrido-1,2-a]pyrazin-7-yl]-methanol (146 mg, 0.51 mmol) prepared as in Step 1, example 72 is added 2 mL of tetrahydrofuran followed by 0.64 mL of a 1.0 M solution of potassium tertbutoxide. The reaction is heated for 30 min. at 50° C. and 1-(6-Chloro-pyridin-3-ylmethyl)-methylethylamine (118 mg, 0.64 mmol) is added. The solution is heated to reflux for 4 h and quenched with 5 mL of water, and extracted with methylene chloride. The organic layer is dried of sodium sulfate, concentrated, and the resultant solide purified by silica gel chromatography to provide the title compound 112 mg (50% yield). Diagnostic $C^{13}$ NMR (100 MHz, $CDCl_3$) 12.5, 25.0, 25.3, 33.5, 41.5, 48.5, 51.1, 53.9, 54.4, 56.7, 58.6, 60.6, 67.0, 110.6, 110.9, 116.4, 122.4, 122.5, 126.9, 129.6, 140.0, 147.2, 161.3, 163.7, 164.1. MS m/z 436.5 (M+1).

EXAMPLE 75

(7S,9aS)-cis-[6-(2-Benzo[d]isoxazol-3-yl-octahydropyrido[1,2-a]pyrazin-7-ylmethoxy)-pyridin-3-ylmethyl]-cyclopentyl-methyl-amine Following the general procedure described in Step 2 of Example 72 and using N-methylcyclopentylamine. The reaction provided 340 mg (77% yield) of (6-Chloro-pyridin-3-ylmethyl)-cyclopentyl-methyl-amine. Diagnostic $^1H$ NMR (400 MHz, $CDCl_3$) 1.40–1.90 (m, 4H), 2.15 (s, 3H), 2.78–2.89 (m, 1H), 3.56 (s, 2H), 7.29 (d, 1H, J=8.3 Hz), 7.70–7.80 (m, 1H), 8.28 (d, 1H, J=2.1 Hz); MS 225.3 (M+H).

To (7S,9aS)-cis-[2-benzo[d]isoxazol-3-yl)-octahydro-pyrido-1,2-a]pyrazin-7-yl]-methanol (147 mg, 0.51 mmol) prepared as in Step 1, example 72 is added 2 mL of tetrahydrofuran followed by 0.64 mL of a 1.0 M solution of potassium tertbutoxide. The reaction is heated for 30 min. at 50° C. and (6-Chloro-pyridin-3-ylmethyl)-cyclopentyl-methyl-amine (143 mg, 0.64 mmol) is added. The solution is heated to reflux for 5 h and quenched with 5 mL of water, and extracted with methylene chloride. The organic layer is dried of sodium sulfate, concentrated, and the resultant solide purified by silica gel chromatography to provide the title compound 150 mg (62% yield). Diagnostic $C^{13}$ NMR (100 MHz, $CDCl_3$) 24.5, 25.0, 25.3, 30.6, 33.5, 39.9, 48.4, 53.8, 54.4, 56.7, 57.3, 60.6, 66.6, 67.0, 110.6, 110.8, 116.4, 122.4, 122.5, 127.1, 129.6, 140.1, 147.2, 161.2, 163.5, 164.1. MS m/z 476.5 (M+1)

EXAMPLE 76

(7S,9aS)-cis-[6-(2-Benzo[d]isoxazol-3-yl-octahydro-pyrido[1,2-a]pyrazin-7-ylmethoxy)-pyridin-3-ylmethyl]-(2-methoxy-ethyl)-methyl-amine Following the general procedure described in Step 2 of Example 72 and using 1-methyl-2-methoxyethylamine. The reaction provided 395 mg (78% yield) of (6-Chloro-pyridin-3-ylmethyl)-(2-methoxy-ethyl)-methyl-amine. Diagnostic $^1$H NMR (400 MHz, CDCl$_3$) 2.25 (s, 3H), 2.59 (t, 2H, J=5.6 Hz), 3.32 (s, 3H), 3.49 (t, 2H, J=5.6 hz), 7.26 (d, 1H, J=8.5 Hz), 7.68 (dd, 1H, J=8.3 and 2.5 Hz), 8.27 9d, 1H, J=1.6 Hz); MS 215.2 (M+H).

To (7S,9aS)-cis-[2-benzo[d]isoxazol-3-yl)-octahydro-pyrido-1,2-a]pyrazin-7-yl]-methanol (152 mg, 0.53 mmol) prepared as in Step 1, example 72 is added 2 mL of tetrahydrofuran followed by 0.66 mL of a 1.0 M solution of potassium tertbutoxide. The reaction is heated for 30 min. at 50° C. and (6-Chloro-pyridin-3-ylmethyl)-(2-methoxy-ethyl)-methyl-amine (141 mg, 0.66 mmol) is added. The solution is heated to reflux for 12 h and quenched with 5 mL of water, and extracted with methylene chloride. The organic layer is dried of sodium sulfate, concentrated, and the resultant solide purified by silica gel chromatography to provide the title compound 20 mg (5% yield). Diagnostic $C^{13}$ NMR (100 MHz, CDCl$_3$) 25.0, 25.3, 33.5, 42.5, 48.4, 53.8, 54.4, 56.2, 56.7, 59.0, 59.3, 60.6, 67.0, 70.8, 110.6, 110.9, 116.4, 129.6, 140.1, 147.3, 161.3, 163.8, 164.1. MS m/z 466.5 (M+1)

EXAMPLE 77

(7S,9aS)-cis-7-(5-Azetidin-1-ylmethyl-pyridin-2-yloxymethyl)-2-benzo[d]isoxazol-3-yl-octahydro-pyrido[1,2-a]pyrazine Following the general procedure described in Step 2 of Example 72 and using azetidine-hydrochloride. The reaction provided 200 mg (53% yield) of 1-(6-Chloro-pyridin-3-ylmethyl)-azetidine. Diagnostic $^1$H NMR (400 MHz, CDCl$_3$) 2.06–2.14 (m, 2H), 3.23 (t, 4H, J=7.0 Hz), 3.55 (s, 2H), 7.27 (d, 1H, J=7.9 Hz), 7.61 (dd, 1H, J=8.3 and 2.5 Hz), 8.26 (d, 1H, J=2.5 Hz); MS 183.2 (M+H).

To (7S,9aS)-cis-[2-benzo[d]isoxazol-3-yl)-octahydro-pyrido-1,2-a]pyrazin-7-yl]-methanol (151 mg, 0.53 mmol) prepared as in Step 1, example 72 is added 2 mL of tetrahydrofuran followed by 0.66 mL of a 1.0 M solution of potassium tertbutoxide. The reaction is heated for 30 min. at 50° C. and 1-(6-Chloro-pyridin-3-ylmethyl)-azetidine (120 mg, 0.66 mmol) is added. The solution is heated to reflux for 5 h and quenched with 5 mL of water, and extracted with methylene chloride. The organic layer is dried of sodium sulfate, concentrated, and the resultant solide purified by silica gel chromatography to provide the title compound 162 mg (71% yield). Diagnostic $C^{13}$ NMR (100 MHz, CDCl$_3$) 17.7, 25.0, 25.2, 33.5, 48.4, 53.8, 54.4, 55.1, 56.7, 60.6, 60.7, 66.9, 110.6, 110.9, 116.4, 122.4, 122.5, 126.4, 129.6, 139.5, 146.7, 161.3, 163.7, 164.1. MS m/z 434.5 (M+1).

EXAMPLE 78

(7S,9aS)-cis-2-Benzo[d]isoxazol-3-yl-7-[5-(2-methyl-aziridin-1-ylmethyl)-pyridin-2-yloxymethyl]-octahydro-pyrido[1,2-a]pyrazine Following the general procedure described in Step 2 of Example 72 and using 2-methyl-aziridine. The reaction provided 66 mg (17% yield) of 2-Chloro-5-(2-methyl-aziridin-1-ylmethyl)-pyridine. Diagnostic $^1$H NMR (400 MHz, CDCl$_3$) 1.15 (d, 3H, J=5.4 Hz), 1.34 (d, 1H, J=6.6 Hz), 1.47–1.55 (m, 2H), 3.35 (abq, 2H, J=5.8 Hz), 7.25 (d, 1H, J=6.3 Hz), 7.65 (dd, 1H, J=8.3 and 2.5 hz), 8.27 (d, 1H, J=1.7 Hz); MS 183.2 (M+H).

To (7S,9aS)-cis-[2-benzo[d]isoxazol-3-yl)-octahydro-pyrido-1,2-a]pyrazin-7-yl]-methanol (179 mg, 0.62 mmol) prepared as in Step 1, example 72 is added 2 mL of tetrahydrofuran followed by 0.78 mL of a 1.0 M solution of potassium tertbutoxide. The reaction is heated for 30 min. at 50° C. and 2-Chloro-5-(2-methyl-aziridin-1-ylmethyl)-pyridine (142 mg, 0.78 mmol) is added. The solution is heated to reflux for 12 h and quenched with 5 mL of water, and extracted with methylene chloride. The organic layer is dried of sodium sulfate, concentrated, and the resultant solide purified by silica gel chromatography to provide the title compound 96 mg (36% yield). Diagnostic $C^{13}$ NMR (100 MHz, CDCl$_3$) 18.5, 25.0, 25.3, 33.5, 35.0, 35.2, 48.4, 53.8, 54.4, 56.7, 60.6, 61.7, 67.0, 110.6, 110.9, 116.4, 1222.4, 122.5, 127.7, 129.6, 139.0, 146.1, 161.2, 163.6, 164.1. MS m/z 434.5 (M+1).

EXAMPLE 79

(7R,9aS)-trans-[6-(2-Benzo[d]isoxazol-3-yl-octahydro-pyrido[1,2-a]pyrazin-7-ylmethoxy)-pyridin-2-ylmethyl]-(2-methoxy-ethyl)-methyl-amine Step 1: To a solution of 2-chloro-6-(bromomethyl)pyridine (490 mg, 2.37 mmole) in 5 mL of dry acetonitrile is added 0.51 mL (4.74 mmol) of 2-methoxy-N-methylethylamine and 328 mg (2.37 mmol) of potassium carbonate. The reaction is heated at 80° C. for 2 h. After cooling, the reaction mixture is quenched with 5 mL of water, extracted three-times with methylene chloride, and dried over sodium sulfate. Concentration of the solvent provided an oil which was purified by silica gel chromatography to provide 478 mg (94% yield) of (6-Chloro-pyridin-2-ylmethyl)-(2-methoxy-ethyl)-methyl-amine. Diagnostic $^1$H NMR (400 MHz, CDCl$_3$) 2.34 (s, 3h), 2.67 (t, 2H, J=5.9 Hz), 3.34 (s, 3H), 3.52 (t, 2H, J=5.8 Hz), 3.71 (s, 3H), 7.19 (d, 1H, J=7.9 Hz), 7.54 (d, 1H, J=7.9 Hz), 7.60–7.64 (m, 1H); MS 215.2 (M+H).

Step 2: To (7R,9aS)-trans-[2-benzo[d]isoxazol-3-yl)-octahydro-pyrido-1,2-a]pyrazin-7-yl]-methanol (171 mg, 0.60 mmol) prepared as in Step 1, example 53 is added 3 mL of tetrahydrofuran followed by 0.74 mL of a 1.0 M solution of potassium tertbutoxide. The reaction is heated for 30 min. at 50° C. and (6-Chloro-pyridin-2-ylmethyl)-(2-methoxy-ethyl)-methyl-amine (158 mg, 0.74 mmol) is added. The solution is heated at 50° C. for 12 h and quenched with 5 mL of water, and extracted with methylene chloride. The organic layer is dried of sodium sulfate, concentrated, and the resultant solide purified by silica gel chromatography to provide the title compound 194 mg (70% yield). Diagnostic $C^{13}$ NMR (100 MHz, CDCl$_3$) 27.2, 29.2, 36.4, 43.2, 48.5, 53.9, 54.4, 56.6, 59.0, 60.3, 63.7, 68.6, 70.9, 108.8, 110.6, 115.9, 116.3, 122.3, 122.4, 129.7, 139.0, 156.8, 161.2, 163.4, 164.1. MS m/z 466.5 (M+1).

EXAMPLE 80

(7R,9aS)-trans-1-[6-(2-Benzo[d]isoxazol-3-yl-octahydro-pyrido[1,2-a]pyrazin-7-ylmethoxy)-pyridin-2-ylmethyl]-pyrrolidin-3-ol Following the general procedure described in Step 1 of Example 79 and using 3-hydroxy-pyrrolidine. The reaction provided 584 mg (90% yield) of 1-(6-Chloro-pyridin-2-ylmethyl)-pyrrolidin-3-ol. Diagnostic $^1$H NMR (400 MHz, CDCl$_3$) 1.76–1.84 (m, 1H), 2.17–2.24 (m, 1H), 2.41–2.47 (m, 2H), 2.65 (dd, 1H, J=10.1 and 5.4 Hz), 2.78 (d, 1H, J=10.4 Hz), 2.96–3.00 (m, 1H), 3.80 (s, 2H), 4.36–4.38 (m, 1H), 7.24 (d, 1H, J=12.9 Hz), 7.38 (d, 1H, J=7.9 Hz), 7.69 (m, 1H); MS 213.2 (M+H).

To (7R,9aS)-trans-[2-benzo[d]isoxazol-3-yl)-octahydro-pyrido-1,2-a]pyrazin-7-yl]-methanol (194 mg, 0.68 mmol) prepared as in Step 1, example 53 is added 3 mL of tetrahydrofuran followed by 0.85 mL of a 1.0 M solution of potassium tertbutoxide. The reaction is heated for 30 min. at 50° C. and 1-(6-Chloro-pyridin-2-ylmethyl)-pyrrolidin-3-ol (180 mg, 0.85 mmol) is added. The solution is heated at 50° C. for 12 h and quenched with 5 mL of water, and extracted with methylene chloride. The organic layer is dried of sodium sulfate, concentrated, and the resultant solide purified by silica gel chromatography to provide the title compound 38 mg (11% yield). MS m/z 464.5 (M+1).

EXAMPLE 81

(7R,9aS)-trans-[6-(2-Benzo[d]isoxazol-3-yl-octahydro-pyrido[1,2-a]pyrazin-7-ylmethoxy)-pyridin-2-ylmethyl]-dimethyl-amine Following the general procedure described in Step 1 of Example 79 and using dimethylamine. The reaction provided 356 mg (81% yield) of 1-(6-Chloro-pyridin-2-ylmethyl)-dimethylamine. Diagnostic $^1$H NMR (400 MHz, CDCl$_3$) 2.30 (s, 6H), 3.58 (s, 2H), 7.20 (d, 1H, J=7.9 Hz), 7.37 (d, 1H, J=11.9 Hz), and 7.61–7.65 (m, 1H); MS 171.2 (M+H).

To (7R,9aS)-trans-[2-benzo[d]isoxazol-3-yl)-octahydro-pyrido-1,2-a]pyrazin-7-yl]-methanol (207 mg, 0.72 mmol) prepared as in Step 1, example 53 is added 3 mL of tetrahydrofuran followed by 0.90 mL of a 1.0 M solution of potassium tertbutoxide. The reaction is heated for 30 min. at 50° C. and 1-(6-Chloro-pyridin-2-ylmethyl)-dimethylamine (153 mg, 0.90 mmol) is added. The solution is heated at 50° C. for 12 h and quenched with 5 mL of water, and extracted with methylene chloride. The organic layer is dried of sodium sulfate, concentrated, and the resultant solide purified by silica gel chromatography to provide the title compound 258 mg (85% yield). Diagnostic C$^{13}$ NMR (100 MHz, CDCl$_3$) 27.2, 29.3, 36.4, 45.8, 48.5, 53.9, 54.4, 59.0, 60.4, 65.6, 68.7, 108.9, 110.6, 115.8, 116.3, 12.3, 122.4, 129.7, 139.0, 156.7, 161.3, 163.5, 164.1. MS m/z 422.4 (M+1).

EXAMPLE 82

(7R,9aS)-trans-[6-(2-Benzo[d]isoxazol-3-yl-octahydro-pyrido[1,2-a]pyrazin-7-ylmethoxy)-pyridin-2-ylmethyl]-cyclohexyl-methyl-amine Following the general procedure described in Step 1 of Example 79 and using N-methylcyclohexylamine. The reaction provided 598 mg (99% yield) of (6-Chloro-pyridin-2-ylmethyl)-cyclohexyl-methyl-amine. Diagnostic $^1$H NMR (400 MHz, CDCl$_3$) 1.06–1.32 (m, 6H), 1.60–1.89 (m, 4H), 2.26 (s, 3H), 2.42–2.47 (m, 1H), 3.71 (s, 2H), 7.17 (d, 1H, J=7.9 Hz), 7.46 (d, 1H, J=7.9 Hz), 7.59–7.63 (m, 1H); MS 239.3 (M+H).

To (7R,9aS)-trans-[2-benzo[d]isoxazol-3-yl)-octahydro-pyrido-[1,2-a]pyrazin-7-yl]-methanol (122 mg, 0.43 mmol) prepared as in Step 1, example 53 is added 3 mL of tetrahydrofuran followed by 0.53 mL of a 1.0 M solution of potassium tertbutoxide. The reaction is heated for 30 min. at 50° C. and (6-Chloro-pyridin-2-ylmethyl)-cyclohexyl-methyl-amine (126 mg, 0.53 mmol) is added. The solution is heated at 50° C. for 12 h and quenched with 5 mL of water, and extracted with methylene chloride. The organic layer is dried of sodium sulfate, concentrated, and the resultant solide purified by silica gel chromatography to provide the title compound 72 mg (34% yield). Diagnostic C$^{13}$ NMR (100 MHz, CDCl$_3$) 26.2, 26.5, 27.2, 29.0, 29.2, 36.4, 38.5, 48.5, 53.9, 54.4, 59.0, 59.4, 60.4, 62.9, 68.7, 108.5, 110.7, 115.4, 116.3, 122.3, 122.4, 129.7, 139.1, 161.3, 163.4, 164.1. MS m/z 490.5 (M+1).

EXAMPLE 83

(7S,9aS)-cis-[6-(2-Benzo[d]isoxazol-3-yl-octahydro-pyrido[1,2-a]pyrazin-7-ylmethoxy)-pyridin-2-ylmethyl]-cyclohexyl-methyl-amine Following the general procedure described in Step 1 of Example 79 and using N-methylcyclohexylamine. The reaction provided 598 mg (99% yield) of (6-Chloro-pyridin-2-ylmethyl)-cyclohexyl-methyl-amine. Diagnostic $^1$H NMR (400 MHz, CDCl$_3$) 1.06–1.32 (m, 6H), 1.60–1.89 (m, 4H), 2.26 (s, 3H), 2.42–2.47 (m, 1H), 3.71 (s, 2H), 7.17 (d, 1H, J=7.9 Hz), 7.46 (d, 1H, J=7.9 Hz), 7.59–7.63 (m, 1H); MS 239.3 (M+H).

To (7S,9aS)-cis-[2-benzo[d]isoxazol-3-yl)-octahydro-pyrido-1,2-a]pyrazin-7-yl]-methanol (122 mg, 0.43 mmol) prepared as in Step 1, example 72 is added 2 mL of tetrahydrofuran followed by 0.53 mL of a 1.0 M solution of potassium tertbutoxide. The reaction is heated for 30 min. at 50° C. and (6-Chloro-pyridin-2-ylmethyl)-cyclohexyl-methyl-amine (126 mg, 0.53 mmol) is added. The solution is heated at 50° C. for 12 h and quenched with 5 mL of water, and extracted with methylene chloride. The organic layer is dried of sodium sulfate, concentrated, and the resultant solide purified by silica gel chromatography to provide the title compound 80 mg (38% yield). Diagnostic C$^{13}$ NMR (100 MHz, CDCl$_3$) 14.3, 22.8, 25.0, 25.3, 26.1, 26.5, 29.0, 33.6, 38.4, 48.5, 53.9, 54.4, 56.8, 59.3, 60.6, 62.8, 66.9, 108.4, 110.6, 115.5, 116.4, 122.4, 129.6, 139.1, 161.3, 163.7, 164.1. MS m/z 490.5 (M+1)

EXAMPLE 84

(7S,9aS)-cis-[6-(2-Benzo[d]isoxazol-3-yl-octahydro-pyrido[1,2-a]pyrazin-7-ylmethoxy)-pyridin-2-ylmethyl]-dimethyl-amine Following the general procedure described in Step 1 of Example 79 and using dimethylamine. The reaction provided 356 mg (81% yield) of 1-(6-Chloro-pyridin-2-ylmethyl)-dimethylamine. Diagnostic $^1$H NMR (400 MHz, CDCl$_3$) 2.30 (s, 6H), 3.58 (s, 2H), 7.20 (d, 1H, J=7.9 Hz), 7.37 (d, 1H, J=11.9 Hz), and 7.61–7.65 (m, 1H); MS 171.2 (M+H).

To (7S,9aS)-cis-[2-benzo[d]isoxazol-3-yl)-octahydro-pyrido-1,2-a]pyrazin-7-yl]-methanol (116 mg, 0.40 mmol) prepared as in Step 1, example 72 is added 2 mL of tetrahydrofuran followed by 0.50 mL of a 1.0 M solution of potassium tertbutoxide. The reaction is heated for 30 min. at 50° C. and 1-(6-Chloro-pyridin-2-ylmethyl)-dimethylamine (85 mg, 0.50 mmol) is added. The solution is heated at 50° C. for 12 h and quenched with 5 mL of water, and extracted with methylene chloride. The organic layer is dried of sodium sulfate, concentrated, and the resultant solide purified by silica gel chromatography to provide the title compound 67 mg (40% yield). Diagnostic $C^{13}$ NMR (100 MHz, CDCl$_3$) 25.0, 25.3, 33.6, 45.8, 48.4, 53.8, 54.4, 56.8, 60.7, 65.5, 66.9, 108.6, 110.7, 115.8, 116.4, 122.4, 129.6, 139.0, 156.9, 161.3, 163.8, 164.1. MS m/z 422.5 (M+1).

EXAMPLE 85

(7S,9aS)-cis-[6-(2-Benzo[d]isoxazol-3-yl-octahydro-pyrido[1,2-a]pyrazin-7-ylmethoxy)-pyridin-2-ylmethyl]-(2-methoxy-ethyl)-methyl-amine Following the general procedure described in Step 1 of Example 79 and using 2-methoxy-N-methylethylamine. The reaction provided 478 mg (94% yield) of (6-Chloro-pyridin-2-ylmethyl)-(2-methoxy-ethyl)-methyl-amine. Diagnostic $^1$H NMR (400 MHz, CDCl$_3$) 2.34 (s, 3h), 2.67 (t, 2H, J=5.9 Hz), 3.34 (s, 3H), 3.52 (t, 2H, J=5.8 Hz), 3.71 (s, 3H), 7.19 (d, 1H, J=7.9 Hz), 7.54 (d, 1H, J=7.9 Hz), 7.60–7.64 (m, 1H); MS 215.2 (M+H).

To (7S,9aS)-cis-[2-benzo[d]isoxazol-3-yl)-octahydro-pyrido-1,2-a]pyrazin-7-yl]-methanol (115 mg, 0.40 mmol) prepared as in Step 1, example 72 is added 2 mL of tetrahydrofuran followed by 0.50 mL of a 1.0 M solution of potassium tertbutoxide. The reaction is heated for 30 min. at 50° C. and (6-Chloro-pyridin-2-ylmethyl)-(2-methoxy-ethyl)-methyl-amine (107 mg, 0.50 mmol) is added. The solution is heated at 50° C. for 12 h and quenched with 5 mL of water, and extracted with methylene chloride. The organic layer is dried of sodium sulfate, concentrated, and the resultant solide purified by silica gel chromatography to provide the title compound 124 mg (67% yield). Diagnostic $C^{13}$ NMR (100 MHz, CDCl$_3$) 25.0, 25.3, 33.6, 43.2, 48.5, 53.8, 54.4, 56.6, 56.8, 59.1, 60.6, 63.7, 66.8, 70.9, 108.6, 110.6, 115.8, 116.4, 122.4, 129.6, 139.0, 156.9, 161.3, 163.7, 164.1. MS m/z 466.5 (M+1).

EXAMPLE 86

(7R,9aS)-trans-1-[6-(2-Benzo[d]isoxazol-3-yl-octahydro-pyrido[1,2-a]pyrazin-7-ylmethoxy)-pyridin-2-ylmethyl]-(R)-pyrrolidin-3-ol Following the general procedure described in Step 1 of Example 79 and using (R)-3-hydroxy-pyrrolidine. The reaction provided 612 mg (93% yield) of (R)-1-(6-Chloro-pyridin-2-ylmethyl)-pyrrolidin-3-ol. Diagnostic $^1$H NMR (400 MHz) 1.76–1.84 (m, 1H), 2.17–2.24 (m, 1H), 2.41–2.47 (m, 2H), 2.65 (dd, 1H, J=10.1 and 5.4 Hz), 2.78 (d, 1H, J=10.4 Hz), 2.96–3.00 (m, 1H), 3.80 (s, 2H), 4.36–4.38 (m, 1H), 7.24 (d, 1H, J=12.9 Hz), 7.38 (d, 1H, J=7.9 Hz), 7.69 (m, 1H; MS 213.2 (M+H).

To (7R,9aS)-trans-[2-benzo[d]isoxazol-3-yl)-octahydro-pyrido-1,2-a]pyrazin-7-yl]-methanol (182 mg, 0.63 mmol) prepared as in Step 1, example 53 is added 3 mL of tetrahydrofuran followed by 0.79 mL of a 1.0 M solution of potassium tertbutoxide. The reaction is heated for 30 min. at 50° C. and (R)-1-(6-Chloro-pyridin-2-ylmethyl)-pyrrolidin-3-ol (168 mg, 0.79 mmol) is added. The solution is heated at 50° C. for 12 h and quenched with 5 mL of water, and extracted with methylene chloride. The organic layer is dried of sodium sulfate, concentrated, and the resultant solide purified by silica gel chromatography to provide the title compound 43 mg (15% yield). Diagnostic $^{13}$C NMR (100 MHz, CDCl$_3$) 27.2, 29.2, 35.1, 36.3, 48.5, 52.8, 53.9, 54.4, 58.9, 60.4, 61.1, 62.9, 68.8, 71.3, 109.5, 110.7, 115.9, 116.3, 122.4, 122.5, 129.8, 139.2, 155.4, 161.2, 163.5, 164.2, MS 464.4 (M+H).

EXAMPLE 87

(7R,9aS)-trans-1-[6-(2-Benzo[d]isoxazol-3-yl-octahydro-pyrido[1,2-a]pyrazin-7-ylmethoxy)-pyridin-2-ylmethyl]-(S)-pyrrolidin-3-ol Following the general procedure described in Step 1 of Example 79 and using (S)-3-hydroxy-pyrrolidine. The reaction provided 584 mg (90% yield) of (S)-1-(6-Chloro-pyridin-2-ylmethyl)-pyrrolidin-3-ol. Diagnostic $^1$H NMR (400 MHz) 1.76–1.84 (m, 1H), 2.17–2.24 (m, 1H), 2.41–2.47 (m, 2H), 2.65 (dd, 1H, J=10.1 and 5.4 Hz), 2.78 (d, 1H, J=10.4 Hz), 2.96–3.00 (m, 1H), 3.80 (s, 2H), 4.36–4.38 (m, 1H), 7.24 (d, 1H, J=12.9 Hz), 7.38 (d, 1H, J=7.9 Hz), 7.69 (m, 1H); MS 213.2 (M+H).

To (7R,9aS)-trans-[2-benzo[d]isoxazol-3-yl)-octahydro-pyrido-1,2-a]pyrazin-7-yl]-methanol (186 mg, 0.65 mmol) prepared as in Step 1, example 53 is added 3 mL of tetrahydrofuran followed by 0.81 mL of a 1.0 M solution of potassium tertbutoxide. The reaction is heated for 30 min. at 50° C. and (S)-1-(6-Chloro-pyridin-2-ylmethyl)-pyrrolidin-3-ol (172 mg, 0.81 mmol) is added. The solution is heated at 50° C. for 12 h and quenched with 5 mL of water, and extracted with methylene chloride. The organic layer is dried of sodium sulfate, concentrated, and the resultant solide purified by silica gel chromatography to provide the title compound 38 mg (13% yield). Diagnostic $^{13}$C NMR (1400 MHz, CDCl$_3$) 27.2, 29.2, 35.1, 36.3, 48.5, 52.7, 53.9, 54.4, 59.0, 60.4, 61.2, 63.1, 68.7, 71.4, 109.1, 110.7, 115.7, 116.3, 122.3, 122.5, 129.7, 139.1, 156.9, 161.2, 163.5, 164.1. MS 464.4 (M+H).

EXAMPLE 88

(7S,9aS)-cis-[6-(2-Benzo[d]isoxazol-3-yl-octahydro-pyrido[1,2-a]pyrazin-7-ylmethoxy)-pyridin-3-ylmethyl]-cyclohexyl-methyl-amine Following the general procedure described in Step 2 of Example 72 and using N-methylcyclohexylamine. The reaction provided 700 mg (95% yield) of (6-Chloro-pyridin-3-ylmethyl)-cyclohexyl-methyl-amine. Diagnostic $C^{13}$ NMR (100 MHz, CDCl$_3$) 26.1, 26.6, 28.9, 37.7, 54.5, 62.8, 124.1, 135.1, 139.5, 149.9; MS 239.3 (M+H).

To (7S,9aS)-cis-[2-benzo[d]isoxazol-3-yl)-octahydro-pyrido-1,2-a]pyrazin-7-yl]-methanol (129 mg, 0.45 mmol) prepared as in Step 1, example 72 is added 2 mL of tetrahydrofuran followed by 0.56 mL of a 1.0 M solution of potassium tertbutoxide. The reaction is heated for 30 min. at 50° C. and (6-Chloro-pyridin-3-ylmethyl)-cyclohexyl-methyl-amine (133 mg, 0.56 mmol) is added. The solution is heated to relux for 12 h and quenched with 5 mL of water, and extracted with methylene chloride. The organic layer is dried of sodium sulfate, concentrated, and the resultant solide purified by silica gel chromatography to provide the title compound 115 mg (52% yield). Diagnostic $C^{13}$ NMR (100 MHz, CDCl$_3$) 25.0, 25.3, 26.1, 26.5, 28.7, 33.5, 37.5, 48.4, 53.8, 54.4, 54.6, 56.7, 60.6, 62.4, 67.0, 110.6, 110.9, 116.4, 122.4, 122.5, 127.9, 129.6, 139.9, 146.9, 161.3, 163.6, 164.1. MS m/z 490.5 (M+1).

EXAMPLE 89

(7S,9aS)-cis-1-[6-(2-Benzo[d]isoxazol-3-yl-octahydro-pyrido[1,2-a]pyrazin-7-ylmethoxy)-pyridin-3-ylmethyl]-pyrrolidin-(S)-3-ol Following the general procedure described in Step 2 of Example 72 and using (S)-3-hydroxy-pyrrolidine. The reaction gave 900 mg (68% yield) of (S)-1-(6-Chloro-pyridin-3-ylmethyl)-pyrrolidin-3-ol. Diagnostic $C^{13}$ NMR (100 MHz, $CDCl_3$) 35.1, 52.5, 56.7, 63.0, 71.4, 124.2, 133.4, 139.6, 149.9, 150.4; MS 213.2 (M+H).

To (7S,9aS)-cis-[2-benzo[d]isoxazol-3-yl)-octahydro-pyrido-1,2-a]pyrazin-7-yl]-methanol (196 mg, 0.68 mmol) prepared as in Step 1, example 2 is added 2.5 mL of tetrahydrofuran followed by 0.85 mL of a 1.0 M solution of potassium tertbutoxide. The reaction is heated for 30 min. at 50° C. and (S)-1-(6-Chloro-pyridin-3-ylmethyl)-pyrrolidin-3-ol (180 mg, 0.85 mmol) is added. The solution is heated to relux for 2 h and quenched with 5 mL of water, and extracted with methylene chloride. The organic layer is dried of sodium sulfate, concentrated, and the resultant solide purified by silica gel chromatography to provide the title compound 37 mg (12% yield). Diagnostic $C^{13}$ NMR (100 MHz, $CDCl_3$) 25.0, 25.2, 33.4, 34.9, 48.4, 52.4, 53.8, 54.4, 56.7, 56.8, 60.6, 62.6, 67.1, 71.2, 110.6, 111.1, 116.4, 122.4, 125.8, 129.7, 140.0, 147.2, 161.3, 163.9, 164.1. MS m/z 464.4 (M+1).

EXAMPLE 90

(7R,9aS)-trans-2-Benzo[d]isoxazol-3-yl-7-(5-pyrrolidin-1-ylmethyl-pyridin-2-yloxymethyl)-octahydropyrido[1,2-a]pyrazine Following the general procedure described in Step 2 of Example 72 and using pyrrolidine. The reaction gave 900 mg (68% yield) of 1-(6-Chloro-pyridin-3-ylmethyl)-pyrrolidine. Diagnostic $^1$H NMR (400 MHz, $CDCl_3$) 1.75–1.78 (m, 4H), 2.45–2.49 (m, 4H), 3.57 (s, 3H), 7.25 (d, 1H, J=3.7 Hz), 7.64 (dd, 1H, J=8.3 and 2.5 Hz), 8.28 (d, 1H, J=2.1 Hz).

To (7R,9aS)-trans-[2-benzo[d]isoxazol-3-yl)-octahydropyrido-1,2-a]pyrazin-7-yl]-methanol (215 mg, 0.75 mmol) prepared as in Step 1, example 53 is added 2.5 mL of tetrahydrofuran followed by 0.94 mL of a 1.0 M solution of potassium tertbutoxide. The reaction is heated for 30 min. at 50° C. and 1-(6-Chloro-pyridin-3-ylmethyl)-pyrrolidine (184 mg, 0.94 mmol) is added. The solution is heated to relux for 2 h and quenched with 5 mL of water, and extracted with methylene chloride. The organic layer is dried of sodium sulfate, concentrated, and the resultant solide purified by silica gel chromatography to provide the title compound 223 mg (67% yield). Diagnostic $C^{13}$ NMR (100 MHz, $CDCl_3$) 23.6, 27.9, 29.2, 36.4, 48.5, 53.9, 54.2, 54.5, 57.4, 59.0, 60.4, 68.9, 110.7, 110.9, 116.4, 122.3, 122.5, 127.6, 129.7, 139.9, 146.9, 161.3, 163.4, and 164.2. MS m/z 448.1 (M+1).

EXAMPLE 91

(7R,9aS)-trans-2-(5-Fluoro-benzo[d]isoxazol-3-yl)-7-(5-pyrrolidin-1-ylmethyl-pyridin-2-yloxymethyl)-octahydro-pyrido[1,2-a]pyrazine Following the general procedure described in Step 2 of Example 72 and using pyrrolidine. The reaction provided 900 mg (68% yield) of 1-(6-Chloro-pyridin-3-ylmethyl)-pyrrolidine. Diagnostic $^1$H NMR (400 MHz, $CDCl_3$) 1.75–1.78 (m, 4H), 2.45–2.49 (m, 4H), 3.57 (s, 3H), 7.25 (d, 1H, J=3.7 Hz), 7.64 (dd, 1H, J=8.3 and 2.5 Hz), 8.28 (d, 1H, J=2.1 Hz).

To (7R,9aS)-trans-[2-(5-fluoro-benzo[d]isoxazol-3-yl)-octahydro-pyrido-1,2-a]pyrazin-7-yl]-methanol (215 mg, 0.75 mmol) prepared as in Step 4, example 1 is added 2.5 mL of tetrahydrofuran followed by 0.94 mL of a 1.0 M solution of potassium tertbutoxide. The reaction is heated for 30 min. at 50° C. and 1-(6-Chloro-pyridin-3-ylmethyl)-pyrrolidine (184 mg, 0.94 mmol) is added. The solution is heated to relux for 2 h and quenched with 5 mL of water, and extracted with methylene chloride. The organic layer is dried of sodium sulfate, concentrated, and the resultant solide purified by silica gel chromatography to provide the title compound 22 mg (5% yield). Diagnostic $^1$H NMR (400 MHz, $CDCl_3$) 1.19 (1H, dq, J=13.2 and 3.6 Hz), 1.39 (dq, 1H, J=13.2 and 3.6 Hz), 1.71–2.0 (m, 8H), 2.16–2.21 (m, 3H), 2.49 (dt, 1H, J=11.6 and 3.2 Hz), 2.61 (m, 2H), 2.85–2.90 (m, 2H), 3.10 (d, 1H, J=11.2 Hz), 3.29 (dt, 1H, J=12.0 and 2.8 Hz), 3.57–3.64 (m, 2H), 3.78 (d, 1H, J=12.0 Hz), 3.88 (d, 1H, J=11.6), 4.06 (dd, 1H, J=10.6 and 7.6 Hz), 4.22 (dd, 1H, J=10.8 and 5.2 Hz), 6.72 (d, 1H, J=8.4 Hz), 7.20–7.23 (m, 2H), 7.33 (dd, 1H, J=8.4 and 2.0 Hz), 7.39 (dd, 1H, J=9.2 and 3.6 Hz), and 8.03 (d, 1H, J=2.0 Hz); MS m/z 466.3 (M+1).

EXAMPLE 92

(7R,9aS)-trans-1-[6-(2-Benzo[d]isoxazol-3-yl-octahydro-pyrido[1,2-a]pyrazin-7-ylmethoxy)-pyridin-3-ylmethyl]-piperidin-4-ol To a well-stirred mixture of (7R,9aS)-trans-[5-(2-Benzo[d]isoxazol-3-yl-octahydro-pyrido[1,2-a]pyrazin-7-ylmethoxy)-pyridin-2-yl]-methanol (120 mg, 0.30 mmol) and triethylamine (0.5 mL, 0.35 mmol) in methylene chloride (5 ml), at ambient temperature, methanesulfonyl chloride (40 pl, 0.05 mmol) was added. The reaction was then stirred for 1 h before quenching with 10% aqueous sodium bicarbonate (with 20 ml of methylene chloride added). The reaction mixture was extracted with three 10 ml fresh portions of methylene chloride. The combined organic extracts were dried (anhydrous sodium sulfate) and concentrated in vacuo to afford the title compound. The product was used in the next step without further purification.

A reaction mixture consisting of (7R,9aS)-trans-methanesulfonic acid 5-(2-benzo[d]isoxazol-3-yl-octahydro-pyrido [1,2-a]pyrazin-7-ylmethoxy)-pyridin-2-yl methyl ester from the previous step and 4-hydroxypiperdine (15 mg, 0.15 mmol) in acetonitrile (1 ml) was stirred in a 2-dram vial at 50° C. for 12 hours. After cooling, the solvent is removed and the residue purified by flash chromatography to provide 20 mg (80%) of the title compound. Diagnostic $C^{13}$ NMR (100 MHz, $CDCl_3$) 27.2, 29.2, 34.6, 36.3, 48.5, 50.9, 53.9, 54.4, 59.0, 59.6, 60.4, 68.9, 110.7, 110.9, 116.4, 122.4, 122.5, 129.7, 140.1, 147.2, 161.3, 163.4, 164.2. MS m/z 478.5 (M+1).

EXAMPLE 93

(7S,9aS)-cis-1-[6-(2-Benzo[d]isoxazol-3-yl-octahydro-pyrido[1,2-a]pyrazin-7-ylmethoxy)-pyridin-3-ylmethyl]-pyrrolidin-(R)-3-ol Following the general procedure described in Step 2 of Example 72 and using (R)-3-hydroxy-pyrrolidine. The reaction gave 900 mg (68% yield) of (R)-1-(6-Chloro-pyridin-3-ylmethyl)-pyrrolidin-3-ol. Diagnostic $C^{13}$ NMR (100 MHz, $CDCl_3$) 35.1, 52.5, 56.7, 63.0, 71.4, 124.2, 133.4, 139.6, 149.9, 150.4; MS 213.2 (M+H).

To (7S,9aS)-cis-[2-benzo[d]isoxazol-3-yl)-octahydro-pyrido-1,2-a]pyrazin-7-yl]-methanol (176 mg, 0.61 mmol) prepared as in Step 1, example 72 is added 2.5 mL of tetrahydrofuran followed by 0.77 mL of a 1.0 M solution of potassium tertbutoxide. The reaction is heated for 30 min. at 50° C. and (R)-1-(6-Chloro-pyridin-3-ylmethyl)-pyrrolidin-3-ol (163 mg, 0.77 mmol) is added. The solution is heated to reflux for 2 h and quenched with 5 mL of water, and extracted with methylene chloride. The organic layer is dried of sodium sulfate, concentrated, and the resultant solide purified by silica gel chromatography to provide the title compound 27 mg (10% yield). Diagnostic $C^{13}$ NMR (100 MHz, $CDCl_3$) 25.0, 25.2, 33.4, 34.9, 48.4, 52.4, 53.8, 54.4, 56.7, 56.8, 60.6, 62.6, 67.1, 71.2, 110.6, 111.1, 116.4, 122.4, 125.8, 129.7, 140.0, 147.2, 161.3, 163.9, 164.1. MS m/z 464.4 (M+1).

EXAMPLE 94

(7R,9aS)-trans-7-(5-Azetidin-1-ylmethyl-pyridin-2-yloxymethyl)-2-(5-fluoro-benzo[d]isoxazol-3-yl)-octahydro-pyrido[1,2-a]pyrazine Following the general procedure described in Step 2 of Example 72 and using azetidine-hydrochloride. The reaction gave 200 mg (53% yield) of 1-(6-Chloro-pyridin-3-ylmethyl)-azetidine. Diagnostic $^1H$ NMR (400 MHz, $CDCl_3$) 2.06–2.14 (m, 2H), 3.23 (t, 4H, J=7.0 Hz), 3.55 (s, 2H), 7.27 (d, 1H, J=7.9 Hz), 7.61 (dd, 1H, J=8.3 and 2.5 Hz), 8.26 (d, 1H, J=2.5 Hz); MS 183.2 (M+H).

To (7R,9aS)-trans-[2-(5-fluoro)-benzo[d]isoxazol-3-yl)-octahydro-pyrido-1,2-a]pyrazin-7-yl]-methanol (95 mg, 0.31 mmol) prepared as in Step 4, example 1 is added 2.5 mL of tetrahydrofuran followed by 0.39 mL of a 1.0 M solution of potassium tertbutoxide. The reaction is heated for 30 min. at 50° C. and 1-(6-Chloro-pyridin-3-ylmethyl)-azetidine (71 mg, 0.39 mmol) is added. The solution is heated to reflux for 5 h and quenched with 5 mL of water, and extracted with methylene chloride. The organic layer is dried of sodium sulfate, concentrated, and the resultant solide purified by silica gel chromatography to provide the title compound 68 mg (49% yield). Diagnostic $C^{13}$ NMR (100 MHz, $CDCl_3$) 17.7, 27.1, 29.2, 36.3, 48.4, 53.9, 54.3, 55.0, 58.9, 60.3, 60.6, 68.8, 107.4, 107.7, 111.0, 111.4, 111.5, 116.6, 118.0, 118.3, 126.5, 139.6, 146.6, 157.1, 159.5, 160.6, 161.3, 163.3. MS m/z 452.4 (M+1).

EXAMPLE 95

(7R,9aS)-trans-{6-[2-(5-Fluoro-benzo[d]isoxazol-3-yl)-octahydro-pyrido[1,2-a]pyrazin-7-ylmethoxy]-pyridin-3-ylmethyl}-dimethyl-amine Following the general procedure described in Step 2 of Example 72 and using dimethylamine. The reaction provided 194 mg (36% yield) of 1-(6-Chloro-pyridin-3-ylmethyl)-dimethylamine. Diagnostic $C^{13}$ NMR (100 MHz, $CDCl_3$) 45.5, 60.7, 124.2, 133.6, 139.7, 150.2, 150.4; MS 173.2 (M+H).

To (7R,9aS)-trans-[2-(5-fluoro)-benzo[d]isoxazol-3-yl)-octahydro-pyrido-1,2-a]pyrazin-7-yl]-methanol (78 mg, 0.25 mmol) prepared as in Step 4, example 1 is added 1.5 mL of tetrahydrofuran followed by 0.32 mL of a 1.0 M solution of potassium tertbutoxide. The reaction is heated for 30 min. at 50° C. and of 1-(6-Chloro-pyridin-3-ylmethyl)-dimethylamine (54 mg, 0.32 mmol) is added. The solution is heated to reflux for 3 h and quenched with 5 mL of water, and extracted with methylene chloride. The organic layer is dried of sodium sulfate, concentrated, and the resultant solide purified by silica gel chromatography to provide the title compound 35 mg (32% yield). Diagnostic $C^{13}$ NMR (100 MHz, $CDCl_3$) 27.1, 29.1, 36.3, 45.3, 48.4, 53.8, 54.3, 58.9, 60.3, 60.9, 68.9, 107.4, 107.7, 111.0, 111.4, 111.5, 116.5, 116.6, 118.1, 118.3, 126.9, 140.0, 147.1, 157.1, 159.5, 160.6, 161.3, 163.5. MS m/z 440.4 (M+1).

EXAMPLE 96

(7R,9aS)-trans-Ethyl-{6-[2-(5-fluoro-benzo[d]isoxazol-3-yl)-octahydro-pyrido[1,2-a]pyrazin-7-ylmethoxy]-pyridin-3-ylmethyl}-methyl-amine Following the general procedure described in Step 2 of Example 72 and using methylethylamine. The reaction gave 1.0 g (87% yield) of 1-(6-Chloro-pyridin-3-ylmethyl)-methylethylamine. Diagnostic $^1H$ NMR (400 MHz, $CDCl_3$) 1.06 (t, 3H, J=7.1 Hz), 2.14 (s, 3H), 2.40 (q, 2H, J=7.1 Hz), 3.43 (s, 2H), 7.25 (d, 1H, J=8.2 Hz), 7.62 (dd, 1H, J=8.2 and 5.8 Hz); MS (187.2 (M+H).

To (7R,9aS)-trans-[2-(5-fluoro)-benzo[d]isoxazol-3-yl)-octahydro-pyrido-1,2-a]pyrazin-7-yl]-methanol (82 mg, 0.27 mmol) prepared as in Step 4, example 1 is added 1.5 mL of tetrahydrofuran followed by 0.34 mL of a 1.0 M solution of potassium tertbutoxide. The reaction is heated for 30 min. at 50° C. and 1-(6-Chloro-pyridin-3-ylmethyl)-methylethylamine (62 mg, 0.34 mmol) is added. The solution is heated to reflux for 3 h and quenched with 5 mL of water, and extracted with methylene chloride. The organic layer is dried of sodium sulfate, concentrated, and the resultant solide purified by silica gel chromatography to provide the title compound 46 mg (38% yield). Diagnostic $C^{13}$ NMR (100 MHz, $CDCl_3$) 12.4, 27.1, 29.1, 36.3, 41.4, 48.4, 50.7, 51.0, 53.8, 54.3, 58.5, 58.9, 60.3, 68.8, 107.3, 107.7, 111.0, 111.4, 111.5, 116.5, 116.6, 118.1, 118.3, 126.9, 140.1, 147.1, 157.1, 159.5, 160.6, 161.3, 163.4. MS m/z 454.5 (M+1).

EXAMPLE 97

(7R,9aS)-trans-2-Benzo[d]isoxazol-3-yl-7-(6-pyrrolidin-1-ylmethyl-pyridin-2-yloxymethyl)-octahydro-pyrido[1,2-a]pyrazine To a solution of (7R,9aS)-trans-methanesulfonic acid 6-(2-benzo[d]isoxazol-3-yl-octahydro-pyrido[1,2-a] pyrazin-7-ylmethoxy)-pyridin-2-ylmethyl ester (59 mg, 0.13 mmol) prepared as in example 40, step 4 and pyrrolidinone (36 mg, 0.5 mmol) in acetonitrile (3 ml) was stirred at 50° C. for 8 hours. After cooling, the solvent is removed and the residue purified by flash chromatography to afford the title compound (35 mg, 64%). Diagnostic $^1H$ NMR (400 MHz, $CDCl_3$) 1.16–1.23 (m, 1H), 1.32–1.42 (m, 1H), 1.69–1.72 (m, 1H), 1.86–1.95 (m, 4H), 2.14–2.20 (m, 2H), 2.45–2.51 (m, 1H), 2.79–3.06 (m, 5H), 3.08–3.10 (m, 1H), 3.25–3.32 (m, 1H), 3.79–3.87 (m, 4H), 3.96 (d, 1H, J=12.8 Hz), 4.04 (dd, 1H, J=10.8 and 7.5 Hz), 4.20 (dd, 1H, J=10.8 and 5.4 Hz), 6.59 (d, 1H, J=7.3 Hz), 7.01 (d, 1H, J=6.6 Hz), 7.16–7.21 (m, 2H), 7.41–7.52 (m, 2H), and 7.66 (d, 1H, J=8.3 Hz). MS m/z 448.3 (M+1).

EXAMPLE 98

(7R,9aS)-trans-[6-(2-Benzo[d]isoxazol-3-yl-octahydro-pyrido[1,2-a]pyrazin-7-ylmethoxy)-pyridin-2-ylmethyl]-benzyl-amine To a solution of (7R,9aS)-trans-methanesulfonic acid 6-(2-benzo[d]isoxazol-3-yl-octahydro-pyrido[1,2-a]pyrazin-7-ylmethoxy)-pyridin-2-ylmethyl ester (55 mmol, 0.14 mmol) prepared as in example 40, step 4 and benzylamine (54 mg, 0.5 mmol) in acetonitrile (3 ml) was stirred at 90° C. for 12 hours. After cooling, the solvent is removed and the residue purified by flash chromatography to afford the title compound (16 mg, 24%). Diagnostic $C^{13}$ NMR (100 MHz, $CDCl_3$) 27.2, 29.1, 36.3, 48.5, 53.3, 53.8, 54.3, 59.0, 60.4, 68.7, 109.2, 110.7, 115.0, 122.3, 122.5, 127.3, 128.5, 128.6, 129.7, 139.2; MS m/z 484.3 (M+1).

EXAMPLE 99

(7R,9aS)-trans-2-Benzo[d]isoxazol-3-yl-7-(6-morpholin-4-ylmethyl-pyridin-2-yloxymethyl)-octahydro-pyrido[1,2-a]pyrazine To a solution of (7R,9aS)-trans-methanesulfonic acid 6-(2-benzo[d]isoxazol-3-yl-octahydro-pyrido[1,2-a]pyrazin-7-ylmethoxy)-pyridin-2-ylmethyl ester (0.13 mmol, 59 mg) prepared as in example 40, step 4 and morpholine (44 mg, 0.5 mmol) in acetonitrile (3 ml) was stirred at 50° C. for 12 hours. After cooling, the solvent is removed and the residue purified by flash chromatography to afford the title compound (29 mg, 51%). Diagnostic $^1H$ NMR (400 MHz, $CDCl_3$) 1.61–1.25 (m, 1H), 1.30–1.39 (m, 1H), 1.65–1.78 (m, 1H), 1.81-1.95 (m, 1H), 1.98–2.15 (m, 1H), 2.20–2.40 (m, 2H), 2.50–2.60 (m, 4H), 2.81–3.01 (m, 2H), 3.01–3.17 (m, 1H), 3.20–3.41 (m, 1H), 3.59 (s, 2H), 3.71–3.74 (m, 4H), 3.87 (d, 1H, J=12.5 Hz), 3.98 (d, 1H, J=12.9 Hz), 4.04 (dd, 1H, J=10.4 and 8.1 Hz), 4.19 (dd, 1H, J=10.8 and 5.4 Hz), 6.56 (d, 1H, J=7.9 Hz), 6.96 (d, 1H, J=6.5 Hz), 7.18–7.21 (m, 2H), 7.42–7.52 (m, 3H), 7.65 (d, 1H, J=6.9 Hz); MS m/z 464.3 (M+1).

EXAMPLE 100

(7R,9aS)-trans-2-Benzo[d]isoxazol-3-yl-7-(5-morpholin-4-ylmethyl-pyridin-2-yloxymethyl)-octahydro-pyrido[1,2-a]pyrazine To a solution of (7R,9aS)-trans-methanesulfonic acid 5-(2-benzo[d]isoxazol-3-yl-octahydro-pyrido[1,2-a]pyrazin-7-ylmethoxy)-pyridin-2-ylmethyl ester (0.25 mmol, 50 mg) prepared as in example 19, step 4 and morpholine (63 mg, 0.75 mmol) in acetonitrile (4 ml) was stirred at 50° C. for 12 hours. After cooling, the solvent is removed and the residue purified by flash chromatography to afford the title compound (31 mg, 26%). Diagnostic $^1H$ NMR (400 MHz, $CDCl_3$) 1.16–1.19 (m, 1H), 1.23–1.28 (m, 1H), 1.70–1.80 (m, 1H), 1.93–2.05 (m, 3H), 2.20–2.39 (m, 2H), 2.39–2.45 (m, 4h), 2.50–2.60 (m, 1H), 2.79–3.02 (m, 2H), 3.05–3.10 (m, 1H), 3.20–3.45 (m, 2H), 3.68–3.72 (m, 4H), 3.89 (d, 1H, J=12.2 Hz), 3.98 (d, 1H, J=12.4 Hz), 4.05 (dd, 1H, J=10.4 and 5.5 Hz), 4.22 (dd, 1H, J=10.3 and 5.4 Hz), 6.15 (d, 1H, J=8.3 Hz), 7.21–7.24 (m, 1H), 7.44–7.52 (m, 2H), 7.57 (dd, 1H, J=8.7 and 2.1 Hz), 7.68 (d, 1H, J=7.9 Hz), 8.00 (d, 1H, J=2.1 Hz) MS m/z 464.3 (M+1).

EXAMPLE 101

(7R,9aS)-trans-2-Benzo[d]isoxazol-3-yl-7-(5-piperidin-1-ylmethyl-pyridin-2-yloxymethyl)-octahydro-pyrido[1,2-a]pyrazine To a solution of (7R,9aS)-trans-methanesulfonic acid 5-(2-benzo[d]isoxazol-3-yl-octahydro-pyrido[1,2-a]pyrazin-7-ylmethoxy)-pyridin-2-ylmethyl ester (0.49 mmol, 249 mg) prepared as in example 19, step 4 and piperdine (125 mg, 1.47 mmol) in acetonitrile (2 ml) was stirred at 50° C. for 12 hours. After cooling, the solvent is removed and the residue purified by flash chromatography to afford the title compound (35 mg, 16%). Diagnostic $C^{13}$ NMR (100 MHz, $CDCl_3$) 27.1, 29.2, 36.6, 48.5, 53.9, 54.3, 54.4, 59.0, 60.4, 68.9, 110.7, 122.3, 129.7; MS m/z 462.4 (M+1).

EXAMPLE 102

(7R,9aS)-trans-[6-(2-Benzo[d]isoxazol-3-yl-octahydro-pyrido[1,2-a]pyrazin-7-ylmethoxy)-pyridin-3-ylmethyl]-diisopropyl-amine To a solution of (7R,9aS)-trans-methanesulfonic acid 5-(2-benzo[d]isoxazol-3-yl-octahydro-pyrido[1,2-a]pyrazin-7-ylmethoxy)-pyridin-2-ylmethyl ester (0.13 mmol, 59 mg) prepared as in example 19, step 4 and diisopropylamine (50 mg, 0.5 mmol) in acetonitrile (2 ml) was stirred at 80° C. for 8 hours. After cooling, the solvent is removed and the residue purified by flash chromatography to afford the title compound (13 mg, 22%). Diagnostic $^1H$ NMR (400 MHz, $CDCl_3$) 0.97 (d, 12H, J=6.6 Hz), 1.15–1.21 (m, 1H), 1.25–1.60 (m, 3H), 1.65–1.75 (m, 1H), 1.85–1.97 (m, 2H), 2.10–2.21 (m, 2H), 2.40–2.51 (m, 1H), 2.85–2.98 (m, 4H), 3.07–3.39 (m, 1H), 3.50 (s, 2H), 3.85 (d, 1H, J=12.1 Hz), 3.94–4.04 (m, 2H), 4.18 (dd, 1H, J=10.4 and 5.4 Hz), 6.63 (d, 1H, J=8.3 Hz), 7.17–7.21 (m, 2H), 7.41–7.47 (m, 2H), 7.56 (d, 1H, J=7.9 Hz), 8.01 (s, 1H); MS m/z 478.4 (M+1).

EXAMPLE 103

(7R,9aS)-trans-2-Benzo[d]isoxazol-3-yl-7-[5-(4-methyl-piperazin-1-ylmethyl)-pyridin-2-yloxymethyl]-octahydro-pyrido[1,2a]pyrazine To a solution of (7R,9aS)-trans-methanesulfonic acid 5-(2-benzo[d]isoxazol-3-yl-octahydro-pyrido[1,2-a]pyrazin-7-ylmethoxy)-pyridin-2-ylmethyl ester (0.13 mmol, 57 mg) prepared as in example 19, step 4 and N-methylpiperazine (60 mg, 0.5 mmol) in acetonitrile (3 ml) was stirred at 90° C. for 12 hours. After cooling, the solvent is removed and the residue purified by flash chromatography to afford the title compound (3 g, 5%). Diagnostic $^1H$ NMR (400 MHz, $CDCl_3$) 3.86 (d, 1H, J=12.4 Hz), 3.92 (d, 1H, J=13.2 Hz), 4.03 (dd, 1H, J=10.4 and 7.5 Hz), 4.21 (dd, 1H, J=10.8 and 5.4 Hz), 6.67 (d, 1H, J=8.3 Hz), 7.17–7.21 (m, 2H), 7.42–7.53 (m, 2H), 7.66 (d, 1H, J=8.3 Hz), 7.97 (d, 1H, J=2.1 Hz); MS m/z 477.4 (M+1).

EXAMPLE 104

(7S,9aS)-cis-2-Benzo[d]isoxazol-3-yl-7-(5-pyrrolidin-1-ylmethyl-pyridin-2-yloxymethyl)-octahydro-pyrido[1,2-a]pyrazine Following the general procedure described in Step 2 of Example 72 and using pyrrolidine. The reaction provided 900 mg (68% yield) of 1-(6-Chloro-pyridin-3-ylmethyl)-pyrrolidine. Diagnostic $^1$H NMR (400 MHz, CDCl$_3$) 1.75–1.78 (m, 4H), 2.45–2.49 (m, 4H), 3.57 (s, 3H), 7.25 (d, 1H, J=3.7 Hz), 7.64 (dd, 1H, J=8.3 and 2.5 Hz), 8.28 (d, 1H, J=2.1 Hz).

To (7S,9aS)-cis-[2-benzo[d]isoxazol-3-yl)-octahydro-pyrido-1,2-a]pyrazin-7-yl]-methanol (574 mg, 2.0 mmol) prepared as in Step 1, example 72 is added 5 mL of tetrahydrofuran followed by 2.2 mL of a 1.0 M solution of potassium tertbutoxide. The reaction is heated for 30 min. at 50° C. and 1-(6-Chloro-pyridin-3-ylmethyl)-pyrrolidine (184 mg, 0.94 mmol) is added. The solution is heated to reflux for 2 h and quenched with 5 mL of water, and extracted with methylene chloride. The organic layer is dried of sodium sulfate, concentrated, and the resultant solide purified by silica gel chromatography to provide the title compound 143 mg (16% yield). Diagnostic C$^{13}$ NMR (100 MHz, CDCl$_3$) 23.6, 25.0, 25.2, 33.5, 48.4, 53.8, 54.1, 54.4, 56.7, 57.3, 60.6, 67.0, 110.7, 110.8, 122.3, 122.4, 129.6, 139.9, 147.0; MS m/z 448.3 (M+1).

EXAMPLE 105

(7S,9aS)-cis-2-Benzo[d]isoxazol-3-yl-7-(6-morpholin-4-yl methyl-pyridin-2-yloxymethyl)-octahydro-pyrido[1,2-a]pyrazine To a solution of (7S,9aS)-cis-methanesulfonic acid 6-(2-benzo[d]isoxazol-3-yl-octahydro-pyrido[1,2-a]pyrazin-7-ylmethoxy)-pyridin-2-ylmethyl ester (0.07 mmol, 35 mg) prepared in a similar manner to the trans-mesylate Example 40, step 4 and morpholine (50 mg, 0.5 mmol) in acetonitrile (2 ml) was stirred at 90° C. for 12 hours. After cooling, the solvent is removed and the residue purified by flash chromatography to afford the title compound (10 mg, 31%). MS m/z 464.3(M+1).

EXAMPLE 106

(7S,9aS)-cis-2-Benzo[d]isoxazol-3-yl-7-(6-pyrrolidin-1-ylmethyl-pyridin-2-yloxymethyl)-octahydro-pyrido[1,2-a]pyrazine To a solution of (7S,9aS)-cis-methanesulfonic acid 6-(2-benzo[d]isoxazol-3-yl-octahydro-pyrido[1,2-a]pyrazin-7-ylmethoxy)-pyridin-2-ylmethyl ester (0.22 mmol, 104 mg) prepared in a similar manner to the trans-mesylate Example 40, step 4 and pyrrolidine (71 mg, 1.0 mmol) in acetonitrile (3 ml) was stirred at 90° C. for 4 hours. After cooling, the solvent is removed and the residue purified by flash chromatography to afford the title compound (34 mg, 35%). Diagnostic $^1$H NMR (400 MHz, CDCl$_3$) 1.42–1.48 (m, 3H), 1.58–1.61 (m, 1H), 1.86–1.91 (m, 5H), 2.01–2.20 (m, 2H), 2.76 (dd, 1H, J=11.6 and 4.7 Hz), 2.35–2.42 (m, 1H), 2.72–2.93 (m, 6H), 3.20–3.27 (m, 1H), 3.76–3.81 (m, 3H), 3.91 (d, 1H, J=12.0 Hz), 4.40–4.49 (m, 2H), 6.62 (d, 1H, J=6.3 Hz), 7.03 (d, 1H, J=7.5 Hz), 7.16–7.20 (m, 2H), 7.45–7.47 (m, 2H), 7.51–7.55 (m, 1H), 7.66 (d, 1H, J=7.9 Hz); MS m/z 448.3 (M+1).

EXAMPLE 107

(7R,9aS)-trans-2-(5-Fluoro-benzo[d]isoxazol-3-yl)-7-(6-pyrrolidin-1-ylmethyl-pyridin-2-yloxymethyl)-octahydro-pyrido[1,2-a]pyrazine To a solution of (7S,9aS)-cis-methanesulfonic acid 6-(2-(5-fluoro)-benzo[d]isoxazol-3-yl-octahydro-pyrido[1,2-a] pyrazin-7-ylmethoxy)-pyridin-2-ylmethyl ester (58 mg, 0.12 mmol) prepared as in example 1, step 4 and pyrrolidine (50 mg, 0.5 mmol) in acetonitrile (3 ml) was stirred at 80° C. for 12 hours. After cooling, the solvent is removed and the residue purified by flash chromatography to afford the title compound (24 mg, 43%). Diagnostic $^1$H NMR (400 MHz, CDCl$_3$) 1.17–1.23 (m, 1H), 1.35–1.42 (m, 1H), 1.72 (d, 1H, J=13.0 Hz), 1.89–1.98 (m, 5H), 2.13–2.21 (m, 2H), 2.46 (dt, 1H, J=11.5 and 2.2 Hz), 2.82–2.87 (m, 5H), 3.07 (d, 1H, J=10.2 Hz), 3.23–3.29 (m, 1H), 3.76 (dd, 1H, J=12.4 and 2.4 hz), 3.83–3.87 (m, 3H), 4.05 (dd, 1H, J=8.6 and 7.5 Hz), 4.21 (dd, 1H, J=10.8 and 5.4 Hz), 6.61 (d, 1H, J=8.3 Hz), 7.03 (d, 1H, J=7.1 Hz), 7.20 (dd, 1H, J=8.7 and 2.6 Hz), 7.29 (dd, 1H, J=8.3 and 2.6 Hz), 7.31 (dd, 1H, J=9.1 and 4.2 hz), 7.54 (dd, 1H, J=7.9 and 7.5 Hz); MS m/z 466.4 (M+1).

EXAMPLE 108

(7R,9aS)-trans-2-(5-Fluoro-benzo[d]isoxazol-3-yl)-7-(6-morpholin-4-ylmethyl-pyridin-2-yloxymethyl)-octahydro-pyrido[1,2-a]pyrazine To a solution of (7S,9aS)-cis-methanesulfonic acid 6-(2-(5-fluoro)-benzo[d]isoxazol-3-yl-octahydro-pyrido[1,2-a] pyrazin-7-ylmethoxy)-pyridin-2-ylmethyl ester (0.16 mmol, 80 mg) prepared as in example 1, step 4 and morpholine (75 mg, 0.5 mmol) in acetonitrile (5 ml) was stirred at 60° C. for 12 hours. After cooling, the solvent is removed and the residue purified by flash chromatography to afford the title compound (18 mg, 23%). Diagnostic $^1$H NMR (400 MHz, CDCl$_3$) 1.16–1.21 (m, 2H), 1.60–2.12 (m, 1H), 1.80–2.25 (m, 4H), 2.41–2.60 (m, 5H), 2.81–2.95 (m, 2H), 3.02–3.09 (m, 1H), 3.21–3.39 (m, 2H), 3.55 (s, 2H), 3.71 (3.88 (m, 4H), 3.86 (d, 1H, J=12.8 Hz), 4.01–4.09 (m, 2H), 4.19 (dd, 1H, J=10.3 and 5.4 Hz), 6.56 (d, 1H, J=8.3 Hz), 6.96 (d, 1H, J=7.1 Hz), 7.18–7.23 (m, 1H), 7.28–7.31 (m, 1H), 7.36 (dd, 1H, J=9.2 and 4.2 Hz), 7.51 (dd, 1H, J=8.3 and 7.5 Hz); MS m/z 482.3 (M+1).

EXAMPLE 109

(7R,9aS)-trans-{6-[2-(5-Fluoro-benzo[d]isoxazol-3-yl)-octahydro-pyrido[1,2-a]pyrazin-7-ylmethoxy]-pyridin-2-ylmethyl}-(2-morpholin-4-yl-ethyl)-amine To a solution of (7R,9aS)-trans-methanesulfonic acid 6-(2-benzo[d]isoxazol-3-yl-octahydro-pyrido[1,2-a] pyrazin-7-ylmethoxy)-pyridin-2-ylmethyl ester (0.16 mmol, 80 mg) prepared as in example 40, step 4 and 4-(2-aminotheyl)morpholine (75 mg, 0.5 mmol) in acetonitrile (3 ml) was stirred at 60° C. for 7 hours. After cooling, the solvent is removed and the residue purified by flash chromatography to afford the title compound (18 mg, 22%). Diagnostic $^1$H NMR (400 MHz, CDCl$_3$) 3.64–3.88 (m, 7H), 4.06 (dd, 1H, J=10.8 and 7.4 Hz), 4.18 (dd, 1H, J=10.8 and 5.4 Hz), 6.60 (d, 1H, J=8.3 Hz), 6.83 (d, 1H, J=7.0 hz), 7.18–7.23 (m, 1H), 7.30 (dd, 1H, J=8.3 and 2.5 Hz), 7.36 (dd, 1H, J=9.2 and 4.2 Hz), 7.51 (dd, 1H, J=7.9 and 7.1 Hz); MS m/z 525.4(M+1).

The following preferred compounds were representatively observed to exhibit a Ki value of about 20 nM or less for at least two of the following receptors: D2, 5HT1B and 5HT2A or an effective Ki value at about 10 nM or less for each of said receptors (7R,9aS)-trans-2-Benzo[d]isoxazol-3-yl-7-(6-morpholin-4-ylmethyl-pyridin-2-yloxymethyl)-octahydro-pyrido[1,2-a]pyrazine (7R,9aS)-trans-2-Benzo[d]isoxazol-3-yl-7-(5-piperidin-1-ylmethyl-pyridin-2-yloxymethyl)-octahydro-pyrido[1,2-a]pyrazine (7R,9aS)-trans-2-(5-Fluoro-benzo[d]isoxazol-3-yl)-7-(5-pyrrolidin-1-ylmethyl-pyridin-2-yloxymethyl)-octahydro-pyrido[1,2-a]pyrazine (7R,9aS)-trans-[6-(2-Benzo[d]isoxazol-3-yl-octahydro-pyrido[1,2-a]pyrazin-7-ylmethoxy)-pyridin-3-ylmethyl]-diethyl-amine (7R,9aS)-trans-[6-(2-Benzo[d]isoxazol-3-yl-octahydro-pyrido[1,2-a]pyrazin-7-ylmethoxy)-pyridin-3-ylmethyl]-dimethyl-amine (7R,9aS)-trans-[6-(2-Benzo[d]isoxazol-3-yl-octahydro-pyrido[1,2-a]pyrazin-7-ylmethoxy)-pyridin-3-ylmethyl]-ethyl-methyl-amine (7R,9aS)-trans-[6-(2-Benzo[d]isoxazol-3-yl-octahydro-pyrido[1,2-a]pyrazin-7-ylmethoxy)-pyridin-3-ylmethyl]-(2-methoxy-1-methyl-ethyl)-amine (7R,9aS)-trans-[6-(2-Benzo[d]isoxazol-3-yl-octahydro-pyrido[1,2-a]pyrazin-7-ylmethoxy)-pyridin-3-ylmethyl]-(2-methoxy-ethyl)-methyl-amine (7R,9aS)-trans-[6-(2-Benzo[d]isoxazol-3-yl-octahydro-pyrido[1,2-a]pyrazin-7-ylmethoxy)-pyridin-3-ylmethyl]-cyclopentyl-methyl-amine (7R,9aS)-trans-7-(5-Azetidin-1-ylmethyl-pyridin-2-yloxymethyl)-2-benzo[d]isoxazol-3-yl-octahydro-pyrido[1,2-a]pyrazine (7R,9aS)-trans-2-Benzo[d]isoxazol-3-yl-7-[5-(2-methyl-aziridin-1-ylmethyl)-pyridin-2-yloxymethyl]-octahydro-pyrido[1,2-a]pyrazine (7R,9aS)-trans-2-Benzo[d]isoxazol-3-yl-7-[5-(2-methoxymethyl-pyrrolidin-1-ylmethyl)-pyridin-2-yloxymethyl]-octahydro-pyrido[1,2-a]pyrazine (7R,9aS)-trans-[6-(2-Benzo[d]isoxazol-3-yl-octahydro-pyrido[1,2-a]pyrazin-7-ylmethoxy)-pyridin-3-ylmethyl]-tert-butyl-amine (7S,9aS)-cis-[6-(2-Benzo[d]isoxazol-3-yl-octahydro-pyrido[1,2-a]pyrazin-7-ylmethoxy)-pyridin-3-ylmethyl]-ethyl-methyl-amine (7S,9aS)-cis-7-(5-Azetidin-1-ylmethyl-pyridin-2-yloxymethyl)-2-benzo[d]isoxazol-3-yl-octahydro-pyrido[1,2-a]pyrazine (7R,9aS)-trans-[6-(2-Benzo[d]isoxazol-3-yl-octahydro-pyrido[1,2-a]pyrazin-7-ylmethoxy)-pyridin-2-ylmethyl]-dimethyl-amine (7R,9aS)-trans-[6-(2-Benzo[d]isoxazol-3-yl-octahydro-pyrido[1,2-a]pyrazin-7-ylmethoxy)-pyridin-2-ylmethyl]-(2-methoxy-ethyl)-methyl-amine (7R,9aS)-trans-1-[6-(2-Benzo[d]isoxazol-3-yl-octahydro-pyrido[1,2-a]pyrazin-7-ylmethoxy)-pyridin-3-ylmethyl]-(S)-pyrrolidin-3-ol (7R,9aS)-trans-1-[6-(2-Benzo[d]isoxazol-3-yl-octahydro-pyrido[1,2-a]pyrazin-7-ylmethoxy)-pyridin-3-ylmethyl]-(R)-pyrrolidin-3-ol (7R,9aS)-trans-2-Benzo[d]isoxazol-3-yl-7-[5-(2-methyl-pyrrolidin-1-ylmethyl)-pyridin-2-yloxymethyl]-octahydro-pyrido[1,2-a]pyrazine (7R,9aS)-trans-1-[6-(2-Benzo[d]isoxazol-3-yl-octahydro-pyrido[1,2-a]pyrazin-7-ylmethoxy)-pyridin-3-ylmethyl]-piperidin-4-ol (7S,9aS)-cis-[6-(2-Benzo[d]isoxazol-3-yl-octahydro-pyrido[1,2-a]pyrazin-7-ylmethoxy)-pyridin-3-ylmethyl]-cyclohexyl-methyl-amine (7R,9aS)-trans-1-[6-(2-Benzo[d]isoxazol-3-yl-octahydro-pyrido[1,2-a]pyrazin-7-ylmethoxy)-pyridin-2-ylmethyl]-(S)-pyrrolidin-3-ol (7R,9aS)-trans-1-[6-(2-Benzo[d]isoxazol-3-yl-octahydro-pyrido[1,2-a]pyrazin-7-ylmethoxy)-pyridin-2-ylmethyl]-(R)-pyrrolidin-3-ol (7R,9aS)-trans-2-Benzo[d]isoxazol-3-yl-7-(6-pyrrolidin-1-ylmethyl-pyridin-2-yloxymethyl)-octahydro-pyrido[1,2-a]pyrazine (7R,9aS)-trans-[6-(2-Benzo[d]isoxazol-3-yl-octahydro-pyrido[1,2-a]pyrazin-7-ylmethoxy)-pyridin-2-ylmethyl]-benzyl-amine (7R,9aS)-trans-2-Benzo[d]isoxazol-3-yl-7-(5-pyrrolidin-1-ylmethyl-pyridin-2-yloxymethyl)-octahydro-pyrido[1,2-a]pyrazine (7S,9aS)-cis-2-Benzo[d]isoxazol-3-yl-7-(5-pyrrolidin-1-yl methyl-pyridin-2-yloxymethyl)-octahydro-pyrido[1,2-a]pyrazine.

What is claimed is:
1. A compound having the formula

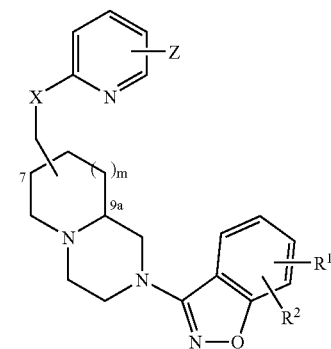

I the (R) or (S) enantiomer thereof, or the cis or trans isomer thereof or a pharmaceutically acceptable salt thereof or solvate of the compound or salt thereof, wherein Z is

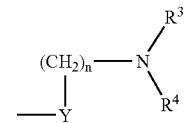

wherein Y is methylene; X is oxygen; n is 0; $R^1$ and $R^2$ are each hydrogen or halogen; and $R^3$ and $R^4$ together with the nitrogen atom to which they are attached form i) a saturated non-aromatic 3 to 7 membered monocyclic ring, said ring i) being unsubstituted or substituted with one or more $(C_1-C_4)$ alkyl, $(C_1-C_4)$alkoxy$(C_1-C_4)$alkyl, or hydroxy groups.

2. The compound of claim 1, wherein said compound is selected from the group consisting of:

(7R,9aS)-trans-7-[6-(2,6-Dimethyl-piperidin-1-ylmethyl)-pyridin-2-yloxymethyl]-2-(5-fluoro-benzo[d]isoxazol-3-yl)-octahydro-pyrido[1,2-a]pyrazine;

(7R,9aS)-trans-2-(5-Fluoro-benzo[d]isoxazol-3-yl)-7-(6-piperidin-1-ylmethyl-pyridin-2-yloxymethyl)-octahydro-pyrido[1,2-a]pyrazine;

(7R,9aS)-trans-7-[6-(2,5-Dimethyl-pyrrolidin-1-ylmethyl)-pyridin-2-yloxymethyl]-2-(5-fluoro-benzo[d]isoxazol-3-yl)-octahydro-pyrido[1,2-a]pyrazine;

(7R,9aS)-trans-7-(6-Azepan-1-ylmethyl-pyridin-2-yloxymethyl)-2-(5-fluoro-benzo[d]isoxazol-3-yl)-octahydro-pyrido[1,2-a]pyrazine;

(7R,9aS)-trans-1-[6-(2-Benzo[d]isoxazol-3-yl-octahydro-pyrido[1,2-a]pyrazin-7-ylmethoxy)-pyridin-3-yl-methyl]-pyrrolidin-3-ol;

(7S,9aS)-cis-7-(5-Azetidin-1-ylmethyl-pyridin-2-yloxymethyl)-2-benzo[d]isoxazol-3-yl-octahydro-pyrido[1,2-a]pyrazine;

(7R,9aS)-trans-2-Benzo[d]isoxazol-3-yl-7-[5-(2-methyl-aziridin-1-ylmethyl)-pyridin-2-yloxymethyl]-octahydro-pyrido[1,2-a]pyrazine;

(7R,9aS)-trans-7-(5-Azepan-1-ylmethyl-pyridin-2-yloxymethyl)-2-(benzo[d]isoxazol-3-yl-octahydro-pyrido[1,2-a]pyrazine;

(7R,9aS)-trans-2-Benzo[d]isoxazol-3-yl-7-[5-(2-methoxymethyl-pyrrolidin-1-ylmethyl)-pyridin-2-yloxymethyl]-octahydro-pyrido[1,2-a]pyrazine;

(7R,9aS)-trans-2-Benzo[d]isoxazol-3-yl-7-[5-(2-methyl-pyrrolidin-1-ylmethyl)-pyridin-2-yloxymethyl]-octahydro-pyrido[1,2-a]pyrazine;

(7S,9aS)-cis-2-Benzo[d]isoxazol-3-yl-7-(5-piperidin-1-ylmethyl-pyridin-2-yloxymethyl)-octahydro-pyrido[1,2-a]pyrazine;

(7S,9aS)-cis-7-(5-Azetidin-1-ylmethyl-pyridin-2-yloxymethyl)-2-benzo[d]isoxazol-3-yl-octahydro-pyrido[1,2-a]pyrazine;

(7S,9aS)-cis-2-Benzo[d]isoxazol-3-yl-7-[5-(2-methyl-aziridin-1-ylmethyl)-pyridin-2-yloxymethyl]-octahydro-pyrido[1,2-a]pyrazine;

(7R,9aS)-trans-1-[6-(2-Benzo[d]isoxazol-3-yl-octahydro-pyrido[1,2-a]pyrazin-7-ylmethoxy)-pyridin-2-yl-methyl]-pyrrolidin-3-ol;

(7R,9aS)-trans-1-[6-(2-Benzo[d]isoxazol-3-yl-octahydro-pyrido[1,2-a]pyrazin-7-ylmethoxy)-pyridin-2-yl-methyl]-(R)-pyrrolidin-3-ol;

(7R,9aS)-trans-1-[6-(2-Benzo[d]isoxazol-3-yl-octahydro-pyrido[1,2-a]pyrazin-7-ylmethoxy)-pyridin-2-yl-methyl]-(S)-pyrrolidin-3-ol;

(7S,9aS)-cis-1-[6-(2-Benzo[d]isoxazol-3-yl-octahydro-pyrido[1,2-a]pyrazin-7-ylmethoxy)-pyridin-3-ylmethyl]-pyrrolidin-(S)-3-ol;

(7R,9aS)-trans-2-Benzo[d]isoxazol-3-yl-7-(5-pyrrolidin-1-ylmethyl-pyridin-2-yloxymethyl)-octahydro-pyrido[1,2-a]pyrazine;

(7R,9aS)-trans-2-(5-Fluoro-benzo[d]isoxazol-3-yl)-7-(5-pyrrolidin-1-ylmethyl-pyridin-2-yloxymethyl)-octahydro-pyrido[1,2-a]pyrazine;

(7R,9aS)-trans-1-[6-(2-Benzo[d]isoxazol-3-yl-octahydro-pyrido[1,2-a]pyrazin-7-ylmethoxy)-pyridin-3-yl-methyl]-piperidin-4-ol;

(7S,9aS)-cis-1-[6-(2-Benzo[d]isoxazol-3-yl-octahydro-pyrido[1,2-a]pyrazin-7-ylmethoxy)-pyridin-3-ylmethyl]-pyrrolidin-(R)-3-ol;

(7R,9aS)-trans-7-(5-Azetidin-1-ylmethyl-pyridin-2-yloxymethyl)-2-(5-fluoro-benzo[d]isoxazol-3-yl)-octahydro-pyrido[1,2-a]pyrazine;

(7R,9aS)-trans-2-Benzo[d]isoxazol-3-yl-7-(6-pyrrolidin-1-ylmethyl-pyridin-2-yloxymethyl)-octahydro-pyrido[1,2-a]pyrazine;

(7R,9aS)-trans-2-Benzo[d]isoxazol-3-yl-7-(5-piperidin-1-ylmethyl-pyridin-2-yloxymethyl)-octahydro-pyrido[1,2-a]pyrazine;

(7S,9aS)-cis-2-Benzo[d]isoxazol-3-yl-7-(5-pyrrolidin-1-ylmethyl-pyridin-2-yloxymethyl)-octahydro-pyrido[1,2-a]pyrazine;

(7S,9aS)-cis-2-Benzo[d]isoxazol-3-yl-7-(6-pyrrolidin-1-ylmethyl-pyridin-2-yloxymethyl)-octahydro-pyrido[1,2-a]pyrazine; and (7R,9aS)-trans-2-(5-Fluoro-benzo[d]isoxazol-3-yl)-7-(6-pyrrolidin-1-ylmethyl-pyridin-2-yloxymethyl)-octahydro-pyrido[1,2-a]pyrazine;

or pharmaceutically acceptable salts thereof.

3. A compound selected from (7R, 9aS)-trans- 1-[6-(2-Benzo[d]isoxazol-3-yl-octahydro-pyrido[1,2-a]pyrazin-7- ylmethoxy)-pyridin-3-yl-methyl]-pyrrolidin-3-ol;

(7R, 9aS)-trans-2-Benzo[d]isoxazol-3-yl-7-[5-(2-methyl-pyrrolidin-1-ylmethyl)-pyridin-2-yloxymethyl]-octahydro-pyrido[1,2-a]pyrazine;

(7R, 9aS)-trans-2-Benzo[d]isoxazol-3-yl-7-(5-pyrrolidin-1-ylmethyl-pyridin-2-yloxymethyl)-octahydro-pyrido[1,2-a]pyrazine;

(7R, 9aS )-trans-2-(5-Fluoro-benzo[d]isoxazol-3-yl)-7-(5-pyrrolidin-1-ylmethyl-pyridin-2-yloxymethyl)-octahydro-pyrido[1,2-a]pyrazine;

(7R, 9aS)-trans-1-[6-(2-Benzo[d]isoxazol-3-yl octahydro-pyrido[1,2-a]pyrazin-7-ylmethoxy)-pyridin-3-yl-methyl]-piperidin-4-ol;

(7R, 9aS)-trans-7-(5-Azetidin-1-ylmethyl-pyridin-2-yloxymethyl)-2-(5-fluoro-benzo[d]isoxazol-3-yl)-octahydro-pyrido[1,2-a]pyrazine; and (7R, 9aS)-trans-2-Benzo[d]isoxazol-3-yl-7-(5-piperidin-1-ylmethyl-pyridin-2-yloxymethyl)-octahydro-pyrido[1,2-a]pyrazine, or pharmaceutically acceptable salts thereof or solvate of the compound or salt thereof.

4. The compound of claim 1 that is selected from (7R, 9aS)-trans-1-[6-(2-Benzo[d]isoxazol-3-yl-octahydro-pyrido[1,2-a]pyrazin-7-ylmethoxy)-pyridin-3-yl-methyl]-pyrrolidin-3-ol;

(7R, 9aS)-trans-2-Benzo[d]isoxazol-3-yl-7-[5-methyl-pyrrolidin-1 -ylmethyl)-pyridin-2-yloxymethyl]-octahydro-pyrido[1,2-a]pyrazine;

(7R, 9aS)-trans-2-Benzo[d]isoxazol-3-yl-7-(5-pyrrolidin-1-ylmethyl-pyridin-2-yloxymethyl)-octahydro-pyrido[1,2-a]pyrazine: and (7R, 9aS)-trans-2-(5-Fluoro-benzo[d]isoxazol-3-yl)-7-(5-pyrrolidin-1 -ylmethyl-pyridin-2-yloxymethyl)-octahydro-pyrido[1,2-a]pyrazine, or pharmaceutically acceptable salts thereof or solvate of the compound or salt thereof.

5. The compound of claim 1 that is selected from (7R, 9aS)-trans-1-[6-(2-Benzo[d]isoxazol-3-yl-octahydro-pyrido[1,2-a]pyrazin-7-ylmethoxy)-pyridin-3-yl-methyl]-pyrrolidin-3-ol;

(7R, 9aS)-trans-2-Benzo[d]isoxazol-3-7-[5-(2-methyl-pyrrolidin-1-ylmethyl)-pyridin-2-yloxymethyl]-octahydro-pyrido-[1,2-a]pyrazine; and (7R, 9aS)-trans-2-(5-Fluoro-benzo[d]isoxazol-3-yl-)-7-(5-pyrrolidin-1-ylmethyl-pyridin-2-yloxymethyl)-octahydro-pyrido[1,2-a]pyrazine, or pharmaceutically acceptable salts thereof or solvate of the compound or salt thereof.

6. The compound of claim 3 that is (7R, 9aS)-trans-2-Benzo[d]isoxazol-3-yl7-(5-pyrrolidin-1-ylmethyl-pyridin-2-yloxymethyl)-octahydro-pyrido[1,2-a]pyrazine, or pharmaceutically acceptable salts thereof or solvate of the compound or salt thereof.

7. The compound of claim 3 that is selected from (7R, 9aS)-trans-1-[6-(2-Benzo[d]isoxazol-3-yl-octahydro-pyrido[1,2-a]pyrazin-7-ylmethoxy)-pyridin-3-yl-methyl]-pyrrolidin-3-ol; and (7R, 9aS)-trans-1-[6-(2-Benzo[d]isoxazol-3-yl-octahydro-pyrido[1,2-a]pyrazin-7-ylmethoxy)-pyridin-3-yl-methyl]-piperidin-4-ol, or pharmaceutically acceptable salts thereof or solvate of the compound or salt thereof.

8. The compound of claim 3 that is (7R, 9aS)-trans-7-(5-Azetidin-1-ylmethyl-pyridin-2-yloxymethyl)-2-(5-fluoro-benzo[d]isoxazol-3-yl)-octahydro-pyrido[1,2-a]pyrazine, or pharmaceutically acceptable salts thereof or solvate of the compound or salt thereof.

9. The compound of claim 3 that is (7R, 9aS)-trans-2-(5-Fluoro-benzo[d]isoxazol-3-yl)-7-(5-pyrrolidin-1-ylmethyl-pyridin-2-yloxymethyl)-octahydro-pyrido[1,2-a]pyrazine, or pharmaceutically acceptable salts thereof or solvate of the compound or salt thereof.

10. A pharmaceutical composition comprising a compound having the formula

I the (R) or (S) enantiomer thereof, or the cis or trans isomer thereof or a pharmaceutically acceptable salt thereof or solvate of the compound or salt thereof, wherein Z is wherein Y is methylene; X is oxygen; n is 0; $R^1$ and $R^2$ are each hydrogen or halogen; and $R^3$ and $R^4$ together with the nitrogen atom to which they are attached form i) a saturated non-aromatic 3 to 7 membered monocyclic ring, said ring i) being unsubstituted or substituted with one or more $(C_1–C_4)$ alkyl, $(C_1–C_4)$alkoxy$(C_1–C_4)$alkyl, or hydroxy groups, in combination with a pharmaceutically acceptable carrier.

11. The composition of claim 10, wherein said compound is selected from the group consisting of (7R,9aS)-trans-7-[6-(2,6-Dimethyl-piperidin-1-ylmethyl)-pyridin-2-yloxymethyl]-2-(5-fluoro-benzo[d]isoxazol-3-yl)-octahydro-pyrido[1,2-a]pyrazine;

(7R,9aS)-trans-2-(5-Fluoro-benzo[d]isoxazol-3-yl)-7-(6-piperidin-1-ylmethyl-pyridin-2-yloxymethyl)-octahydro-pyrido[1,2-a]pyrazine;

(7R,9aS)-trans-7-[6-(2,5-Dimethyl-pyrrolidin-1-ylmethyl)-pyridin-2-yloxymethyl]-2-(5-fluoro-benzo[d]isoxazol-3-yl)-octahydro-pyrido[1,2-a]pyrazine;

(7R,9aS)-trans-7-(6-Azepan-1-ylmethyl-pyridin-2-yloxymethyl)-2-(5-fluoro-benzo[d]isoxazol-3-yl)-octahydro-pyrido[1,2-a]pyrazine;

(7R,9aS)-trans-1-[6-(2-Benzo[d]isoxazol-3-yl-octahydro-pyrido[1,2-a]pyrazin-7-ylmethoxy)-pyridin-3-ylmethyl]-pyrrolidin-3-ol;

(7S,9aS)-cis-7-(5-Azetidin-1-ylmethyl-pyridin-2-yloxymethyl)-2-benzo[d]isoxazol-3-yl-octahydro-pyrido[1,2-a]pyrazine;

(7R,9aS)-trans-2-Benzo[d]isoxazol-3-yl-7-[5-(2-methyl-aziridin-1-ylmethyl)-pyridin-2-yloxymethyl]-octahydro-pyrido[1,2-a]pyrazine;

(7R,9aS)-trans-7-(5-Azepan-1-ylmethyl-pyridin-2-yloxymethyl)-2-benzo[d]isoxazol-3-yl)-octahydro-pyrido[1,2-a]pyrazine;

(7R,9aS)-trans-2-Benzo[d]isoxazol-3-yl-7-[5-(2-methoxymethyl-pyrrolidin-1-ylmethyl)-pyridin-2-yloxymethyl]-octahydro-pyrido[1,2-a]pyrazine;

(7R,9aS)-trans-2-Benzo[d]isoxazol-3-yl-7-[5-(2-methyl-pyrrolidin-1-ylmethyl)-pyridin-2-yloxymethyl]-octahydro-pyrido[1,2-a]pyrazine;

(7S,9aS)-cis-2-Benzo[d]isoxazol-3-yl-7-(5-piperidin-1-ylmethyl-pyridin-2-yloxymethyl)-octahydro-pyrido[1,2-a]pyrazine;

(7S,9aS)-cis-7-(5-Azetidin-1-ylmethyl-pyridin-2-yloxymethyl)-2-benzo[d]isoxazol-3-yl-octahydro-pyrido[1,2-a]pyrazine;

(7S,9aS)-cis-2-Benzo[d]isoxazol-3-yl-7-[5-(2-methyl-aziridin-1-ylmethyl)-pyridin-2-yloxymethyl]-octahydro-pyrido[1,2-a]pyrazine;

(7R,9aS)-trans-1-[6-(2-Benzo[d]isoxazol-3-yl-octahydro-pyrido[1,2-a]pyrazin-7-ylmethoxy)-pyridin-2-yl-methyl]-pyrrolidin-3-ol;

(7R,9aS)-trans-1-[6-(2-Benzo[d]isoxazol-3-yl-octahydro-pyrido[1,2-a]pyrazin-7-ylmethoxy)-pyridin-2-yl-methyl]-(R)-pyrrolidin-3-ol;

(7R,9aS)-trans-1-[6-(2-Benzo[d]isoxazol-3-yl-octahydro-pyrido[1,2-a]pyrazin-7-ylmethoxy)-pyridin-2-yl-methyl]-(S)-pyrrolidin-3-ol;

(7S,9aS)-cis-1-[6-(2-Benzo[d]isoxazol-3-yl-octahydro-pyrido[1,2-a]pyrazin-7-ylmethoxy)-pyridin-3-ylmethyl]-pyrrolidin-(S)-3-ol;

(7R,9aS)-trans-2-Benzo[d]isoxazol-3-yl-7-(5-pyrrolidin-1-ylmethyl-pyridin-2-yloxymethyl)-octahydro-pyrido[1,2-a]pyrazine;

(7R,9aS)-trans-2-(5-Fluoro-benzo[d]isoxazol-3-yl)-7-(5-pyrrolidin-1-ylmethyl-pyridin-2-yloxymethyl)-octahydro-pyrido[1,2-a]pyrazine;

(7R,9aS)-trans-1-[6-(2-Benzo[d]isoxazol-3-yl-octahydro-pyrido[1,2-a]pyrazin-7-ylmethoxy)-pyridin-3-ylmethyl]-piperidin-4-ol;

(7S,9aS)-cis-1-[6-(2-Benzo[d]isoxazol-3-yl-octahydro-pyrido[1,2-a]pyrazin-7-ylmethoxy)-pyridin-3-ylmethyl]-pyrrolidin-(R)-3-ol;

(7R,9aS)-trans-7-(5-Azetidin-1-ylmethyl-pyridin-2-yloxymethyl)-2-(5-fluoro-benzo[d]isoxazol-3-yl)-octahydro-pyrido[1,2-a]pyrazine;

(7R,9aS)-trans-2-Benzo[d]isoxazol-3-yl-7-(6-pyrrolidin-1-ylmethyl-pyridin-2-yloxymethyl)-octahydro-pyrido[1,2-a]pyrazine;

(7R,9aS)-trans-2-Benzo[d]isoxazol-3-yl-7-(5-piperidin-1-ylmethyl-pyridin-2-yloxymethyl)-octahydro-pyrido[1,2-a]pyrazine;

(7S,9aS)-cis-2-Benzo[d]isoxazol-3-yl-7-(5-pyrrolidin-1-ylmethyl-pyridin-2-yloxymethyl)-octahydro-pyrido[1,2-a]pyrazine;

(7S,9aS)-cis-2-Benzo[d]isoxazol-3-yl-7-(6-pyrrolidin-1-ylmethyl-pyridin-2-yloxymethyl)-octahydro-pyrido[1,2-a]pyrazine; and (7R,9aS)-trans-2-(5-Fluoro-benzo[d]isoxazol-3-yl)-7-(6-pyrrolidin-1-ylmethyl-pyridin-2-yloxymethyl)-octahydro-pyrido[1,2-a]pyrazine;

or pharmaceutically acceptable salts thereof or solvate of the compound or salt thereof.

12. A pharmaceutically composition comprising the compound of claim 3, or the (R) or (S) enantiomer thereof, or the cis or trans isomer thereof, or a pharmaceutically acceptable salt thereof, or solvate of the compound or salt thereof; and a pharmaceutically acceptable carrier.

13. A method of treating a disorder selected from schizophrenia, schizophreniform disorder, schizoaffective disorder, delusional disorder, substance-induced psychotic disorder, personality disorder of the schizoid type, schizoaffective disorder of the delusional type or the depressive type; psychosis induced by alcohol, amphetamine, cannabis, cocaine, hallucinogens, inhalants, or phencyclidine; multi-infarct dementia, dementia associated with intracranial tumors or cerebral trauma, dementia associated with Huntington's disease or Parkinson's disease, or AIDS-related dementia; Alzheimer's related dementia; delirium; and Tourette's syndrome in a mammal, comprising administering to a mammal in need of such treatment a therapeutically effective amount of the compound of claim 3, or the (R) or (S) enantiomer thereof, or the cis or trans isomer thereof, or a pharmaceutically acceptable salt thereof, or solvate of the compound or salt thereof.

14. A method of treating a disorder selected from schizophrenia, schizophreniform disorder, schizoaffective disorder, delusional disorder, substance-induced psychotic disorder, personality disorder of the schizoid type, schizoaffective disorder of the delusional type or the depressive type; psychosis induced by alcohol, amphetamine, cannabis, cocaine, hallucinogens, inhalants, or phencyclidine; multi-infarct dementia, dementia associated with intracranial tumors or cerebral trauma, dementia associated with Huntington's disease or Parkinson's disease, or AIDS-related dementia; Alzheimer's related dementia; delirium; ant Tourette's syndrome in a mammal, comprising administering to a mammal in need of such treatment a therapeutically effective amount of the compound of claim 1, of the (R) or (S) enantiomer thereof, or the cis or trans isomer thereof, or a pharmaceutically acceptable salt thereof, or solvate of the compound or salt thereof.

* * * * *